US010672120B2

(12) United States Patent
Kang et al.

(10) Patent No.: US 10,672,120 B2
(45) Date of Patent: Jun. 2, 2020

(54) METHODS AND SYSTEM FOR LINKING GEOMETRY OBTAINED FROM IMAGES

(71) Applicant: Bio-Tree Systems, Inc., Framingham, MA (US)

(72) Inventors: Kongbin Kang, Providence, RI (US); Yanchun Wu, Sharon, MA (US); Raul A. Brauner, Framingham, MA (US)

(73) Assignee: Bio-Tree Systems, Inc., Framingham, MA (US)

(*) Notice: Subject to any disclaimer, the term of this patent is extended or adjusted under 35 U.S.C. 154(b) by 0 days.

(21) Appl. No.: 15/600,886

(22) Filed: May 22, 2017

(65) Prior Publication Data
US 2017/0278243 A1 Sep. 28, 2017

Related U.S. Application Data

(63) Continuation of application No. 14/853,940, filed on Sep. 14, 2015, which is a continuation of application No. PCT/US2014/028183, filed on Mar. 14, 2014.
(Continued)

(51) Int. Cl.
*G06T 7/00* (2017.01)
*G06T 17/00* (2006.01)
(Continued)

(52) U.S. Cl.
CPC ............ *G06T 7/0012* (2013.01); *A61B 6/032* (2013.01); *A61B 6/504* (2013.01); *A61B 6/5247* (2013.01);
(Continued)

(58) Field of Classification Search
CPC ....... A61B 6/032; A61B 6/504; A61B 6/5247; G06K 9/6202; G06K 9/6212;
(Continued)

(56) References Cited

U.S. PATENT DOCUMENTS 6,361,557 B1 * 3/2002 Gittings ............... A61F 2/07
606/151
2002/0136437 A1 9/2002 Gerard et al.
(Continued)

OTHER PUBLICATIONS

International Search Report and Written Opinion dated Aug. 14, 2014 in corresponding PCT application No. PCT/US2014/028183.
(Continued)

*Primary Examiner* — Manuchehr Rahmjoo
(74) *Attorney, Agent, or Firm* — Nields, Lemack & Frame, LLC

(57) ABSTRACT

Techniques for linking geometry extracted from one or more medical images, the geometry including a plurality of geometric objects each having parameter values including at least one value for location and at least one value for direction/orientation, the plurality of geometric objects comprising a target geometric object and at least two candidate geometric objects, the techniques include: (A) comparing parameter values of the target geometric object with parameter values of the at least two candidate geometric objects, (B) selecting one of the at least two candidate geometric objects to link to the target geometric object based, at least in part, on the comparison; and (C) linking the to target geometric object with the selected candidate geometric object.

14 Claims, 29 Drawing Sheets

Related U.S. Application Data

(60) Provisional application No. 61/791,870, filed on Mar. 15, 2013.

(51) Int. Cl.
*G06T 7/70* (2017.01)
*G06T 7/11* (2017.01)
*G06T 7/12* (2017.01)
*G06T 7/181* (2017.01)
*G06T 7/187* (2017.01)
*A61B 6/00* (2006.01)
*A61B 6/03* (2006.01)
*G06K 9/62* (2006.01)

(52) U.S. Cl.
CPC ......... *G06K 9/6202* (2013.01); *G06K 9/6212* (2013.01); *G06K 9/6214* (2013.01); *G06T 7/11* (2017.01); *G06T 7/12* (2017.01); *G06T 7/181* (2017.01); *G06T 7/187* (2017.01); *G06T 7/70* (2017.01); *G06T 17/005* (2013.01); *G06T 2207/10081* (2013.01); *G06T 2207/30101* (2013.01)

(58) Field of Classification Search
CPC ................ G06K 9/6214; G06T 17/005; G06T 2207/10081; G06T 2207/30101; G06T 7/0012; G06T 7/11; G06T 7/12; G06T 7/181; G06T 7/187
USPC ........................................................ 382/131
See application file for complete search history.

(56) References Cited

U.S. PATENT DOCUMENTS

| | | |
|---|---|---|
| 2005/0043637 A1 | 2/2005 | Caplan et al. |
| 2005/0259882 A1 | 11/2005 | Dewaele |
| 2006/0005139 A1 | 1/2006 | Comaniciu et al. |
| 2006/0280351 A1 | 12/2006 | Zhou et al. |
| 2007/0116342 A1* | 5/2007 | Zarkh .................... G06T 7/564 382/130 |
| 2008/0186311 A1 | 8/2008 | Claus |
| 2011/0103657 A1 | 5/2011 | Kang et al. |
| 2012/0150048 A1* | 6/2012 | Kang .................... A61B 6/508 600/481 |
| 2016/0239956 A1 | 8/2016 | Kang et al. |

OTHER PUBLICATIONS

Office action dated Feb. 22, 2017 in co-pending U.S. Appl. No. 14/853,940.

* cited by examiner

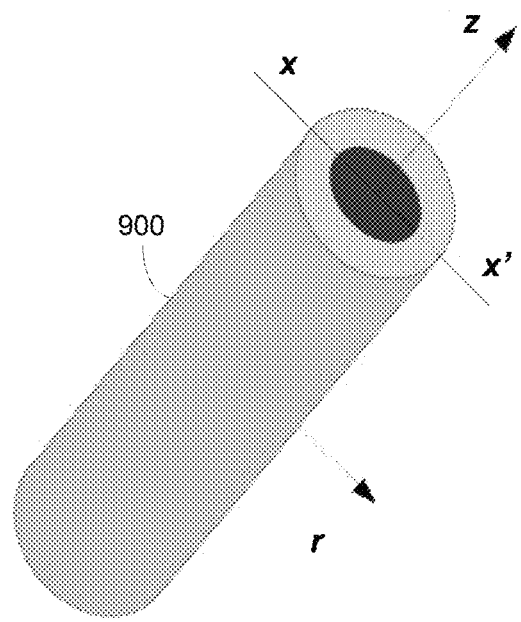
FIG. 10A
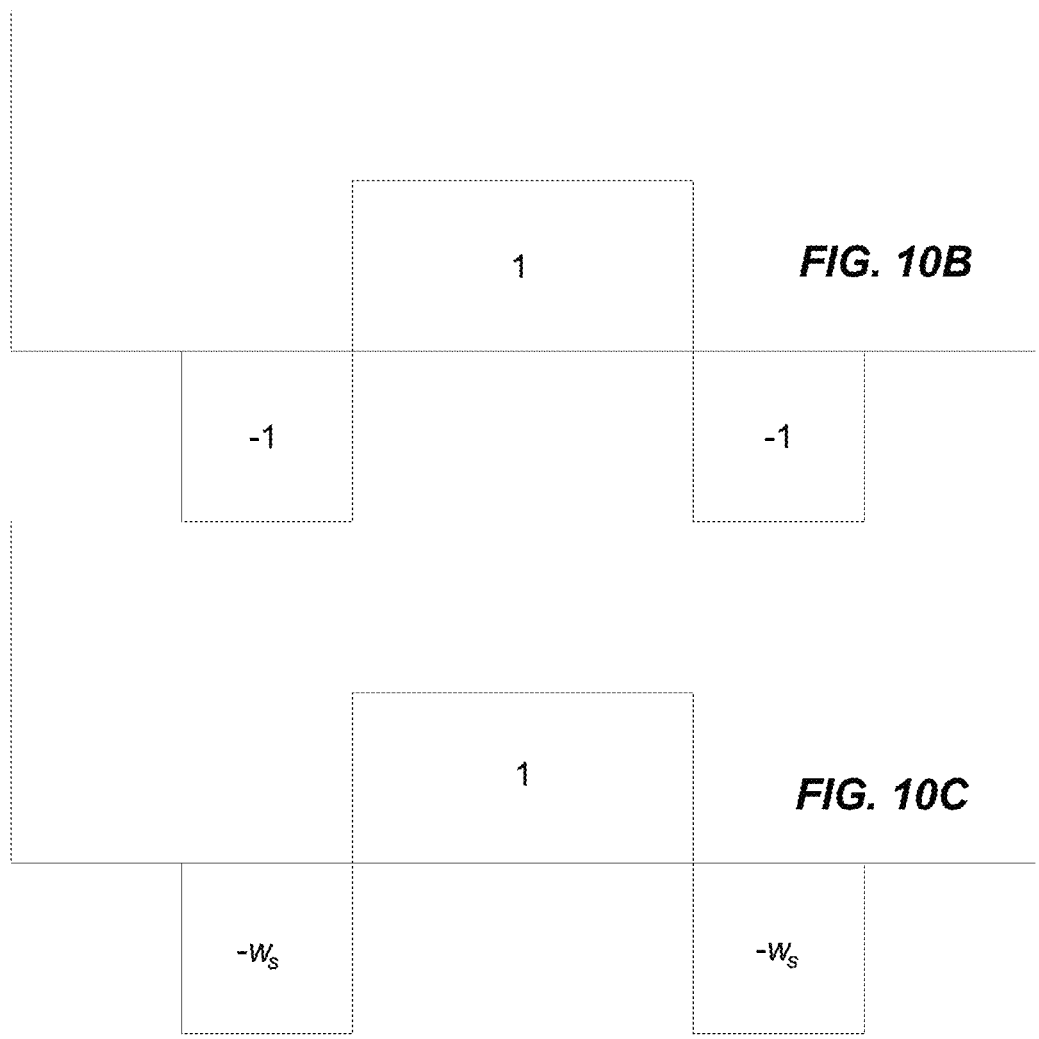
FIG. 10B
FIG. 10C

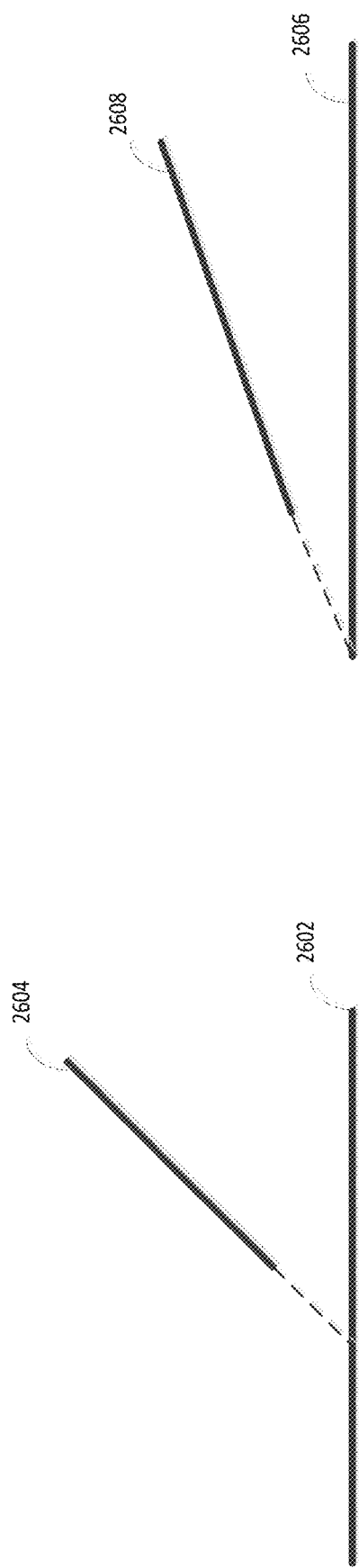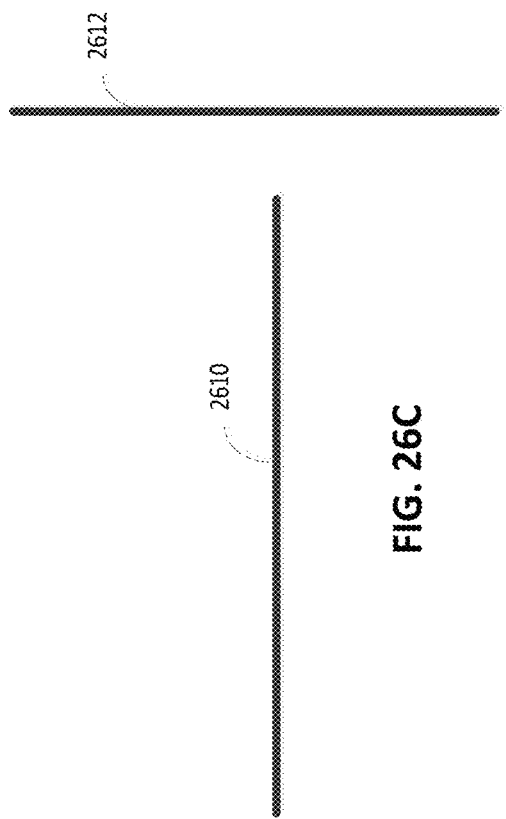
FIG. 26A
FIG. 26B
FIG. 26C

METHODS AND SYSTEM FOR LINKING GEOMETRY OBTAINED FROM IMAGES

BACKGROUND

A wide range of imaging methods and devices are commonly used to evaluate different anatomical and physiological conditions in a variety of medical and research environments. Tools have been developed to image body structures based on different physical properties. For example, X-rays, CT scans, MRIs, PET scans, IR analyses and other technologies have been developed to obtain images of various body structures. These tools are routinely used for diagnostic, therapeutic, and research applications. Combinations of two or more different imaging techniques are sometimes used to provide complementary information about a patient.

In conventional medical imaging, a human operator, such as a physician or diagnostician, may visually inspect one or more images to make an assessment, such as detection of a tumor or other pathology or to otherwise characterize the internal structures of a patient. However, this process may be difficult and time consuming. For example, it may be difficult to assess 3D biological structure by attempting to follow 2D structure through a series of stacked 2D images. In particular, it may be perceptually difficult and time consuming to understand how 2D structure is related to 3D structure as it appears, changes in size and shape, and/or disappears in successive 2D image slices. A physician may have to mentally arrange hundreds or more 2D slices into a 3D picture of the anatomy. To further frustrate this process, when anatomical structure of interest is small, the structure may be difficult to discern or it may be difficult to understand how numerous structures relate to a biological whole.

Furthermore, in addition to the time consuming nature of manual inspection, human visual interpretation of images has further shortcomings. While the human visual cortex processes image information to obtain qualitative information about structure in the image, it does not compute quantitative geometry from the image. However, the quantitative geometry of the structure represented in one or more images may contain valuable information about the structure that can be used to diagnose disease, assess the efficacy of treatment and/or perform other analyses of the structure. Such quantitative information about the structure is beyond the capability of conventional human visual image understanding alone.

Image processing techniques have been developed to automate or partially automate the task of understanding and partitioning the structure in an image and are employed in computer aided diagnosis (CAD) to assist a physician in identifying and locating structure of interest in a 2D or 3D image. CAD techniques often involve segmenting the image into groups of related pixels and identifying the various groups of pixels, for example, as those comprising a tumor or a vessel or some other structure of interest. However, conventional segmentation may produce unsatisfactory or incomplete results, particularly when the structure being detected appears in the image at arbitrary locations, sizes and orientations. As a result, the limited geometry that may be extracted from conventional image processing may be unsuitable for use in further analysis based on the extracted geometry.

SUMMARY

The inventors have developed methods and apparatus for extracting geometry from images, scan data, and/or representations of tubular body structures (e.g., blood vessels or other body vessels). Aspects of the technology described herein relate to obtaining vessel geometry, determining one or more structural features from the vessel geometry, and/or analyzing the one or more structural features for medical diagnostic, prognostic, and/or research applications.

The inventors have developed methods and apparatus for extracting geometry from images, scan data, and/or representations of tubular body structures (e.g., blood vessels or other body vessels). Aspects of the technology described herein are useful for obtaining a geometrical representation of a vascular tree that contains data relating to three-dimensional location, orientation and/or size at any point in the vascular tree of a subject. In some embodiments, a vascular tree may be represented by a series of disks or poker chips (e.g., circular or elliptical disks) that are linked together to form a three-dimensional structure containing information relating to the local size, shape, branching, and other structural features at any point in the vascular tree.

It should be appreciated that the entire vascular tree of a subject may be represented by a network of linked poker chips (e.g., circular or elliptical disks). However, in many embodiments, only a subset or a portion of a vascular tree may be represented or analyzed. In some embodiments, a portion of a vascular tree can be represented by a single disc or poker chip that contains information relating to the location of the center of the vessel, vessel size (diameter), and/or orientation (e.g., the direction of the centerline of the vessel). In some embodiments, a portion of a vascular tree may be represented by a dataset that describes one or more poker chips along with information relating to the linkage between the poker chips within a region of interest of the vascular tree.

Some embodiments are directed to an apparatus for linking geometry extracted from one or more medical images, the geometry including a plurality of geometric objects each having parameter values including at least one value for location and at least one value for direction/orientation, the plurality of geometric objects comprising a target geometric object and at least two candidate geometric objects. The apparatus comprises at least one processor configured to perform: (A) comparing parameter values of the target geometric object with parameter values of the at least two candidate geometric objects at least in part by: comparing at least one value for location of the target geometric object to respective values for location of the at least two candidate geometric objects, and comparing at least one value for direction/orientation of the target geometric object to respective values for direction/orientation of the at least two candidate geometric objects, (B) selecting one of the at least two candidate geometric objects to link to the target geometric object based, at least in part, on the comparison; and (C) linking the target geometric object with the selected candidate geometric object.

Some embodiments are directed to at least one non-transitory computer readable medium storing instructions that, when executed by at least one processor, perform a method of linking geometry extracted from one or more medical images, the geometry including a plurality of geometric objects each having parameter values including at least one value for location and at least one value for direction/orientation, the plurality of geometric objects comprising a target geometric object and at least two candidate geometric objects, the method comprising: (A) comparing parameter values of the target geometric object with parameter values of the at least two candidate geometric objects at least in part by: comparing at least one value for location of the target geometric object to respective values for location of the at least two candidate geometric objects, and comparing at least one value for direction/orientation of the target geometric object to respective values for direction/orientation of the at least two candidate geometric objects, (B) selecting one of the at least two candidate geometric objects to link to the target geometric object based, at least in part, on the comparison; and (C) linking the target geometric object with the selected candidate geometric object.

Some embodiments are directed to a method of linking geometry extracted from one or more medical images, the geometry including a plurality of geometric objects each having parameter values including at least one value for location and at least one value for direction/orientation, the plurality of geometric objects comprising a target geometric object and at least two candidate geometric objects, the method comprising: (A) comparing parameter values of the target geometric object with parameter values of the at least two candidate geometric objects at least in part by: comparing at least one value for location of the target geometric object to respective values for location of the at least two candidate geometric objects, and comparing at least one value for direction/orientation of the target geometric object to respective values for direction/orientation of the at least two candidate geometric objects, (B) selecting one of the at least two candidate geometric objects to link to the target geometric object based, at least in part, on the comparison; and (C) linking the target geometric object with the selected candidate geometric object.

In some embodiments, each of the plurality of geometric objects further has at least one value for scale, and (A) further comprises comparing at least one value for scale of the target geometric object to respective values for scale of the at least two candidate geometric objects.

In some embodiments, including any of the preceding embodiments, each of the plurality of geometric objects further has at least one value for response of a scale detection filter, and wherein (A) further comprises: comparing at least one value for response of the scale detection filter of the target geometric object to respective values for response of the scale detection filter of the at least two candidate geometric objects.

In some embodiments, including any of the preceding embodiments, the geometry represents a vessel network and the target geometric object represents a cross-section of a vessel structure in the vessel network, and wherein (A) is performed by using a statistical model that provides a likelihood that a candidate geometric object of the plurality of geometric objects follows the target geometric object as a geometric representation of another cross-section of the vessel structure based, at least in part, on the at least one location value and the at least direction/orientation value of the target object and at least one location value and at least one direction orientation value of the candidate geometric object.

In some embodiments, including any of the preceding embodiments, the statistical model provides the likelihood that the candidate geometric object of the plurality of geometric objects follows the target geometric object as a geometric representation of another cross-section of the vessel structure further based on at least one value for scale of the target geometric object and at least one value for scale of the candidate geometric object.

In some embodiments, including any of the preceding embodiments, the statistical model provides a probability for parameters of a candidate geometric object conditioned on parameters of the target geometric object.

In some embodiments, including any of the preceding embodiments, comparing the at least one value for direction/orientation of the target geometric object to respective values for direction/orientation of the at least two candidate geometric objects is performed by using a super-Gaussian probability model.

In some embodiments, including any of the preceding embodiments, the method further comprises calculating the at least one value for direction/orientation of the target object based, at least in part, on location information of voxels in at least one segmented image.

In some embodiments, including any of the preceding embodiments, the at least one segmented image includes at least one scale image.

In some embodiments, including any of the preceding embodiments, the calculating further comprises computing displacement vectors between at least one voxel location associated with the target geometric object and at least one voxel location in a neighborhood associated with the target geometric object.

In some embodiments, including any of the preceding embodiments, the method further comprises performing principal component analysis on a matrix formed from the computed displacement vectors.

In some embodiments, including any of the preceding embodiments, the at least one value for orientation is related to an eigenvector of the matrix.

Some embodiments include a method of computing direction/orientation of a geometric object extracted from CT information using at least one segmented image computed from the CT information, the method comprising determining at least one displacement vector from a voxel location associated with the geometric object and at least one other voxel location in a neighborhood associated with the geometric object, and determining a direction/orientation of the geometric object based, at least in part, on the at least one displacement vector. According to some embodiments, the at least one segmented image includes at least one scale image.

Some embodiments of methods for computing direction/orientation include performing principal component analysis on a matrix formed from the at least one displacement vector. According to some embodiments, the direction/orientation is related to an eigenvector of the matrix.

Some embodiments includes at least one computer readable medium storing instructions that, when executed by at least one processor, perform a method of computing direction/orientation of a geometric object extracted from CT information using at least one segmented image computed from the CT information, the method comprising determining at least one displacement vector from a voxel location associated with the geometric object and at least one other voxel location in a neighborhood associated with the geometric object, and determining a direction/orientation of the geometric object based, at least in part, on the at least one displacement vector.

Some embodiments include an apparatus for computing direction/orientation of a geometric object extracted from CT information using at least one segmented image computed from the CT information, the apparatus comprising at least one processor configured to determine at least one displacement vector from a voxel location associated with the geometric object and at least one other voxel location in a neighborhood associated with the geometric object, and determine a direction/orientation of the geometric object based, at least in part, on the at least one displacement vector.

Some embodiments include a method of determining a branch point candidate corresponding to a location where a vessel structure branches, the branch point determined from geometry extracted from CT information that comprises a plurality of geometric objects including a first geometric object, the method comprising determining at least one displacement vector from a voxel location associated with the first geometric object and at least one other voxel location in a neighborhood associated with the first geometric object, and determining at least one value indicative of an asymmetry at the first geometric object based, at least in part, on the at least one displacement vector.

According to some embodiments, the branch point is determined using at least one segmented image, and according to some embodiments, the at least one segmented image includes at least one scale image. Some embodiments of methods of determining a branch point candidate include performing principal component analysis on a matrix derived from the at least one displacement vector. According to some embodiments, the at least one value indicative of an asymmetry is related to an eigenvalue of one of the eigenvectors of the matrix.

Some embodiments include at least one computer readable medium storing instructions that, when executed by at least one processor, performs a method of determining a branch point candidate corresponding to a location where a vessel structure branches, the branch point determined from geometry extracted from CT information that comprises a plurality of geometric objects including a first geometric object, the method comprising determining at least one displacement vector from a voxel location associated with the first geometric object and at least one other voxel location in a neighborhood associated with the first geometric object, and determining at least one value indicative of an asymmetry at the first geometric object based, at least in part, on the at least one displacement vector.

Some embodiments include an apparatus for determining a branch point candidate corresponding to a location where a vessel structure branches, the branch point determined from geometry extracted from CT information that comprises a plurality of geometric objects including a first geometric object, the method comprising at least one processor configured to determine at least one displacement vector from a voxel location associated with the first geometric object and at least one other voxel location in a neighborhood associated with the first geometric object, and determine at least one value indicative of an asymmetry at the first geometric object based, at least in part, on the at least one displacement vector.

Some embodiments include methods for detecting and resolving loops in vessel so that the linked vessel structure (e.g., a directed or non-directed graph) accurately represents loops in the vessel structure (e.g., the graph structure may be cyclic). According to some embodiments, loops are detected in part by labeling Poker Chips™ as visited and/or linked such that when a Poker Chip™ that is labeled as visited and/or linked is identified as a link candidate for more than a single link structure, the Poker Chip™ can be evaluated from both directions to assess whether the vessel structure forms a loop.

Some embodiments include accelerating linking by dividing a geometric representation and associated image data (e.g., intensity, segmented, scale image(s), etc.) into smaller regions and processing them in parallel. The inventors have developed techniques for stitching the linked structures from the smaller regions together to form a larger linked structure representing the vessel network. According to some embodiments, location and direction of Poker Chips™ in a glue region at the juncture of adjacent regions are evaluated to determine how sub-structures should be stitched or glued together to form a larger linked structure.

According to aspects of the technology described herein, a poker chip representation of a vasculature may be mined for physiological, biological, and/or medical purposes. In some embodiments, geometrical information associated with a single poker chip may be mined. In some embodiments, geometrical information associated with a plurality of poker chips, optionally including local linkage information may be mined.

Accordingly, aspects of the technology described herein relate to obtaining vessel geometry, determining one or more structural features from the vessel geometry, and/or analyzing the one or more structural features for medical diagnostic, prognostic, and/or research applications.

Aspects of the technology described herein provide methods for analyzing structures such as blood vessels and evaluating their association with disease, responsiveness to therapeutic treatments, and/or other conditions. Aspects of the technology described herein provide quantitative and analytical methods for evaluating and/or comparing the vessels in different regions of the same body (e.g., a human body) or within ex vivo tissues or between different bodies (e.g., the same regions in different bodies) or different ex vivo tissues. Aspects of the technology described herein can be useful in assisting and/or automating the analysis of vascular patterns and their association with disease diagnosis, prognosis, response to therapy, toxicity evaluation, etc., or any combination thereof. Aspects of the technology described herein can be used in connection with vessel structural information that is obtained from vessel images (e.g., blood vessel images), scan data, vessel representations (e.g., a reconstructed vasculature, a representation that can be viewed as being similar in some ways to a stack of poker chips with varying diameters and is that is referred to herein as a Poker Chip representation, or any other useful representation, or any combination thereof).

Methods are provided for analyzing vessel structural features, and blood vessel structural features in particular. In some embodiments, a distribution of vessel parameters (e.g., structural features or morphological parameters) within a region of interest may be generated and evaluated. In some embodiments, the vessel parameters may relate to the size, shape, or number of vessels with a region of interest. A distribution may be generated based on quantitative measurements related to one or more parameters. In some embodiments, a distribution of blood vessels may be a population distribution of blood vessels as a function of quantitative measures of one or more parameters. For example, a distribution may represent the number of blood vessels (or the percentage of the blood vessel population) as a function of their diameter, branching frequency, distance between branches, degree of tortuousity, curvature, or any other quantitative structural feature or morphological parameter, e.g., as described herein, or any combination of two or more thereof. In some embodiments, a distribution may be divided into groups or bins representing different value ranges of the quantitative measurements (e.g., ranges of vessel diameters such as 0-30 microns, 30-60 microns, 60-90 microns, 90-120 microns, 120-150 microns, 150-180 microns, etc., or any combination thereof). It should be appreciated that a distribution may be represented in any suitable form, for example graphically (e.g., a graph or histogram), in the form of a table, as a database, in a computer-readable or computer storage medium, etc., or any combination thereof.

BRIEF DESCRIPTION OF THE DRAWINGS

FIG. 10A illustrates a centerline filter, in accordance with some embodiments of the technology described herein;

FIG. 10B illustrates a profile of the centerline filter illustrated in FIG. 9A along the line x-x', in accordance with some embodiments of the technology described herein;

FIG. 10C illustrates another profile of the centerline filter illustrated in FIG. 9A along the line x-x', in accordance with some embodiments of the technology described herein;

FIGS. 26A, 26B, and 26C illustrate Y, V, and T structures of vessel branch points, respectively, in accordance with some embodiments of the technology described herein;

DETAILED DESCRIPTION

Figure 1:
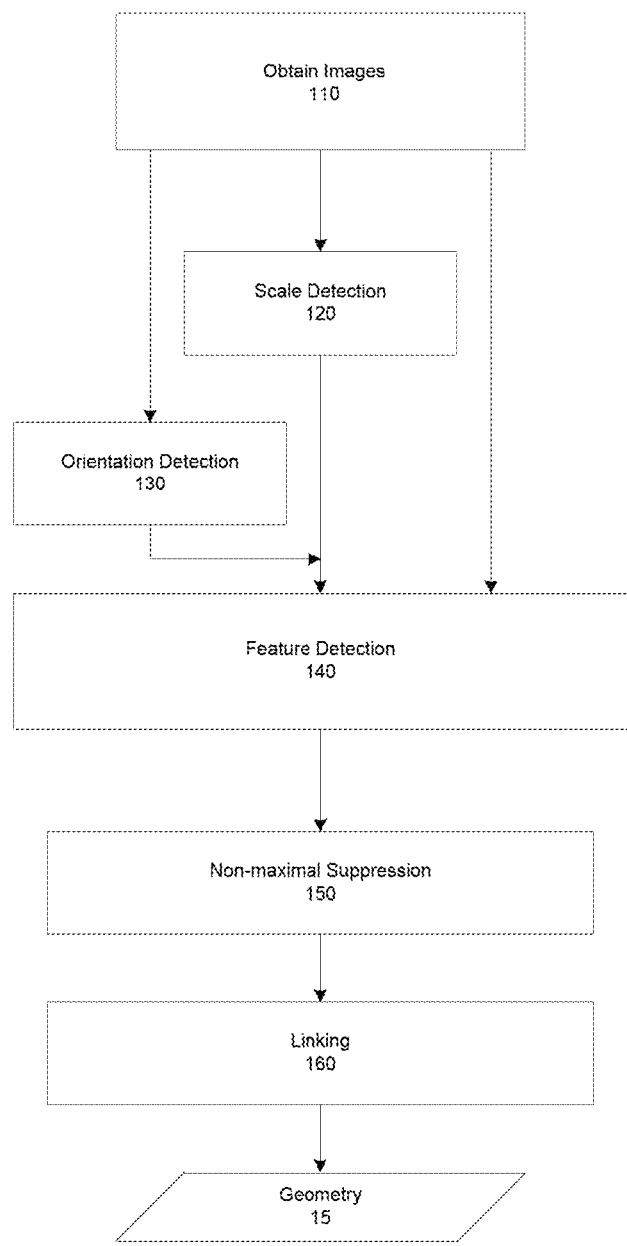
FIG. 1 illustrates a flow chart of extracting geometry from an image, in accordance with some embodiments of the technology described herein.

As discussed above, analyzing vessel structures (e.g., blood vessel structures) and identifying structural profiles that are characteristic of one or more physiological conditions or responses (e.g., positive responses to pharmaceutical compounds) may be of interest in many areas of diagnostics, therapeutics and/or treatment. However, the amount of information that can be directly obtained or ascertained from image data (e.g., x-ray, CT, MRI, etc.) may be prohibitively limited in this respect. Accordingly, the inventors have recognized the benefit of developing methods of extracting geometry from images to facilitate the above described analysis.

To extract geometrical properties of vessel structures in one or more images, the vessels must first be detected in the image and represented in a meaningful fashion. Various methods have been proposed for detecting one or more features of a blood vessel using a filter adapted to respond to the one or more features. For example, filters have been designed to respond to the intensity profile of a vessel to locate voxels that exhibit this intensity profile. However, conventional filtering techniques may be unsatisfactory at accurately and robustly detecting vessel structures in one or more images. Filtering techniques typically require some additional preprocessing to obtain information about the image to improve the filtering process. For example, the scale of the structure at a particular location in the image may be obtained to determine what size filter should be used at that location. That is, not only should the filter match the feature being detected, in order to respond correctly, the filter should also match the scale of the feature. Moreover, because the orientation of the feature being detected is not known a priori, filtering techniques often include some preprocessing to determine the orientation of the feature at a particular location so that the filter can be applied to the image in general alignment with the feature.

Conventionally, scale detection and orientation detection are performed simultaneously. The inventors have appreciated that simultaneous scale and orientation detection may result in sub-optimal detection of either scale, orientation or both. As a result, subsequent filtering to detect one or more features applied using sub-optimal scale and orientation parameters may be substantially degraded. The inventors have developed a method for detecting vessel features that includes a scale detection operation and an orientation detection operation that are performed separately. In some embodiments, scale detection is performed prior to orientation detection, and orientation detection is performed using the scale determined by the scale detection. The scale and orientation values determined from the separate scale and orientation detection operations may then be used to apply the feature detection filter, for example, a centerline filter adapted to respond to the centerline voxels of blood vessels.

According to some embodiments, scale detection employs an orientation independent scale detector such that scale detection may be performed independent of orientation detection. According to some embodiments, an orientation independent scale filter is used having a filter kernel that is symmetric with respect to orientation such that the filter does not rely on orientation for accurate scale detection. According to some embodiments, the orientation independent scale filter includes a filter size defined by a radius. At each of a plurality of selected voxels in an image, the orientation independent scale filter is applied at increasing radii until the filter response fails to meet a predetermined criteria. The largest radius at which the filter response meets the predetermined criteria is used to represent the scale. According to some embodiments, the diameter of vessel structures in the images is determined based on this largest radius. That is, according to some embodiments, at least some geometry of vessel structures may be determined by the scale detection operation.

The inventors have appreciated that performing scale detection, orientation detection and centerline detection provides, at each detected centerline voxel, the location, the direction of the centerline and the radius of the vessel. This geometry can be used to analyze vascular structure and these geometrical parameters have been used to develop a mathematical representation of the detected vessel structure. In some embodiments, each centerline location may be represented as a circular or elliptical disk having a center at the centerline location, a radius corresponding to the associated scale, and a normal vector to the disk (e.g., circular disk) corresponding to the direction of the centerline as determined during orientation detection. This representation resembles a poker chip and is referred to herein as the Poker Chip™ representation, as described in further detail below.

While the Poker Chip™ representation provides much useful information about the geometry of the vessel, without further processing, there is no notion of adjacency or vessel membership, which may be useful information in performing analysis on the vasculature. Accordingly, in some embodiments, each of the detected centerline voxels (e.g., center locations of a poker chip) are linked together to capture adjacency information as well as vessel membership. In some embodiments, the centerline voxels are linked according to a criteria that includes one or any combination of minimizing a distance, a direction change, a radius change, and/or a filter response change from a centerline voxel to an adjacent centerline voxel. That is, when selecting between a number of candidate centerline voxels to link to a target centerline voxel, the centerline voxel candidate that creates the smallest change in one or more of the above parameters may be preferred over candidate centerline voxels having larger changes. The linked centerline voxels can then be used to compute various structural characteristics of the vasculature formed by the detected vessels as represented by the stacked and linked poker chips.

To generate more comprehensive linked structures, points at which vessels branch may be detected so that vessel centerlines from branched vessels can be appropriately linked together. The inventors have appreciated that branch points may often exhibit an asymmetric property associated with the detected centerline points. In view of this insight, the inventors have developed techniques to detect at least one indication of asymmetry to identify branch point candidates. According to some embodiments, detecting the at least one indication of asymmetry comprises performing principal component analysis on a neighborhood of respective target centerline voxels detected from an image (e.g., a 3D image) of vasculature. According to some embodiments, the principal directions of variation and/or their respective significance may be evaluated to assess the symmetry/asymmetry of the neighborhood of a target centerline voxel to determine the likelihood that a branch point is present. For example, the eigenvectors and/or associated eigenvalues computed from a matrix formed from the neighborhood of a centerline voxel may be evaluated to detect at least one indication of asymmetry at a location associated with the centerline voxel. However, other measures of asymmetry may be computed in other ways to identify branch point candidates, as the aspects are not limited in this respect.

Following below are more detailed descriptions of various concepts related to, and embodiments of, methods and apparatus according to the present invention. It should be appreciated that various aspects of the invention described herein may be implemented in any of numerous ways. Examples of specific implementations are provided herein for illustrative purposes only. In addition, the various aspects of the invention described in the embodiments below may be used alone or in any combination, and are not limited to the combinations explicitly described herein.

FIG. 1 illustrates a method of extracting vessel geometry from one or more images of vasculature, in accordance with some embodiments of the technology described herein. Act 110 includes obtaining image information of at least a portion of a vasculature structure. For example, the image information may be a two-dimensional (2D), three-dimensional (3D) or other dimensional image obtained from scanning an object using x-ray CT, MRI, PET, SPECT, etc. The scanned object may be a live specimen such as a human or other animal (i.e., an in-vivo scan), or obtained from a cast of a specimen's vasculature.

The method of FIG. 1 may be performed on any image of any dimension independent of how the image was obtained, as the aspects of the invention are not limited in this respect. In 2D images, each 2D location having an associated intensity is conventionally referred to as a pixel. In 3D images, each volume location having an associated intensity is conventionally referred to as a voxel. The term voxel is used herein to refer to both 2D and 3D image locations to eliminate the need to specify the dimensionality of the images, as the methods described herein are generic to dimensionality.

Many techniques for extracting information from images use various filtering techniques. For example, filters are often designed such that when applied to a portion of an image (e.g., convolved with a portion of the image) the filter response is relatively large when the filter is applied to an image portion having a feature or characteristic indicative of structure being detected in the image, and relatively small otherwise. The filter detection described below in connection with act 140 is one example of matched filtering. However, other filtering techniques may be used, as the aspects of the technology described herein are not limited in this respect.

When the feature or structure being detected appears in an image at different sizes or scales, the size of the filter kernel should be adjusted to the appropriate scale in order for the filter response to accurately indicate the presence of the desired feature. For example, in an image containing biological vasculature, and in particular, tumor vasculature, the constituent vessels will typically vary greatly in diameter. Accordingly, a filter designed to detect relatively large vessels will not respond accordingly to small vessels, even when applied on the correct location. However, it is not known a priori where large and small vessels are located. Accordingly, successful detection may require determining the scale of the structure in the image prior to applying the filter. This technique is herein referred to as "scale detection." Scale detection may be performed on predetermined portions of an image, or may be determined on a voxel by voxel basis, as described in further detail below.

In addition to detecting the appropriate scale, it may be beneficial to detect the orientation in which the filter should be applied. In particular, the feature(s) being detected may appear in the image at arbitrary orientations. For example, in the case of vasculature, the vessel properties being detected may be oriented in any arbitrary direction. Accordingly, even if a filter at the appropriate scale is applied at an image region corresponding to the feature being detected, the filter response may be relatively low if it is not oriented in general alignment with the direction of the feature for which the filter was designed to detect. Accordingly, determining the orientation of the features or properties being detected may benefit filter detection techniques. This technique is herein referred to as "orientation detection."

Conventional filtering techniques combine scale and orientation detection in a single operation. That is, the combination of possible scales and orientations are tested simultaneously and the scale and orientation are selected when the response is maximum. However, the inventors have appreciated that maximum responses may not correspond to optimal scale and optimal orientation simultaneously. Because the response is a combination of scale and orientation, one or both may be sub-optimal while together providing a strong response. The inventors have developed a scale detection operation that is orientation independent. As a result, the operations of scale detection and orientation detection may be separated into two separate operations. In addition, the detected scale may then be used to improve subsequent orientation detection processes.

In act 120, scale detection is performed independently of orientation detection. In some embodiments, scale detection 120 is performed using a filter that is independent of orientation. Scale detection 120 may provide the scale in the image at different regions in the image. In some embodiments, scale detection 120 determines scale at each voxel in the image. Alternatively, a preprocessing operation may be performed to roughly determine which voxels in the image correspond to subject matter of interest (e.g., vessels) and which voxels correspond to background. Scale detection may then be performed only on pixels determined to correspond to subject matter of interest, thus reducing the amount of computations. The result of scale detection is a scale associated with each location at which the filter was applied (e.g., a scale at each selected voxel in the image). An orientation independent scale detection algorithm according to some embodiments is described in further detail below.

In act 130, orientation detection may be performed. To assist in more accurate orientation detection, the scale at the selected regions of the image determined during scale detection 120 may be provided to the orientation detection operation. As discussed above, determining the orientation of subject matter of interest in one or more images may be important for accurate filter detection of the subject matter of interest (e.g., structure, feature, property or characteristic). For example, in embodiments where the subject matter of interest is vasculature, it may be important to detect the direction of the center or longitudinal axis of the vessels before applying a filter that detects the centerline of the vessel. In some embodiments, the scale determined from scale detection 120 may be used to improve orientation detection accuracy. The result of orientation detection is an orientation or direction at each selected voxel indicating the direction of the centerline at the respective location. An orientation detection algorithm according to some embodiments is described in further detail below.

In act 140, filter detection may be performed. In filter detection 140, a filter designed to respond to the subject matter of interest in the image may be applied. In some embodiments, the filter is applied at the scale and/or orientation determined from scale detection and/or orientation detection, respectively. The magnitude of the filter response at selected locations in the image indicates the likelihood that the location includes the subject matter of interest. In some embodiments, the subject matter of interest is vasculature and the filter is designed to respond to the center of a vessel. That is, the filter may be designed to respond to the intensity profile across a vessel and thus respond most strongly when centered on a centerline voxel in the direction of the intensity profile. Because the scale and direction of the subject matter of interest has been determined at selected locations in the image, filter detection may appropriately accurate in detecting the subject matter of interest. Several methods of centerline filtering are discussed in detail below, in accordance with some embodiments of the technology described herein.

In act 150, non-maximal suppression may be performed on the output of the filter detection operation performed in act 140. As discussed above, the result of a filtering operation (e.g., centerline filtering) generally includes the filter response at each voxel at which the filter was applied. The magnitude of the response is typically proportional to the likelihood that the feature being detected is present at the corresponding voxel location. However, it should be appreciated that many voxel locations will have associated non-zero filter responses. In addition, some voxel locations will have associated local maximum filter responses even though the true location of the feature is elsewhere. However, accurate detection may require discriminating between local maximum and the true maximum location, which corresponds to the most likely location of the structure being detected. Non-maximal suppression 150 attempts to eliminate or suppress all but the true maximum filter responses to accurately detect the subject matter of interest. A detailed description of non-maximum suppression in the context of centerline filtering for vessel detection is described below.

In act 160, linking may be performed. Linking may include various operations that associate voxel locations with each other to form related structures so that geometric properties may be obtained from the linked voxels. For example, in the context of vessel detection, the voxel locations that were determined as centerline voxels after centerline detection and non-maximum suppression may be linked together to form the associated centerline of vessels. That is, analysis may be performed to link together centerline voxels that are likely to have arisen from the same vessel structure. In such a way, the geometry of the vessels may be obtained (e.g., geometry 15). Methods for linking voxels in the context of vessel detection are described in further detail below.

As discussed above, some embodiments are directed to detecting vasculature and extracting the geometry of the vasculature to facilitate various analysis such as diagnosis, therapeutics, drug efficacy, etc. The inventors have developed methods for extracting geometrical information from 3D volumetric images using a match filter based system to segment a vessel network and extract a mathematical (geometry) vessel representation. Some embodiments of a vessel representation are referred to herein as the Poker Chip™ representation due to the similarity to a stack of poker chips. The Poker Chip™ representation treats a vessel as an aggregation of infinitesimal cylinder cross-sections with continuously varying diameters. While in theory the "thickness" of each poker chip is infinitesimal, in practice the thickness of each poker chip may be related to the resolution of the image(s) from which the geometry was extracted. Thus, each poker chip may have associated geometry including, for example, center location, radius and orientation, as discussed in further detail below.

Figure 2:
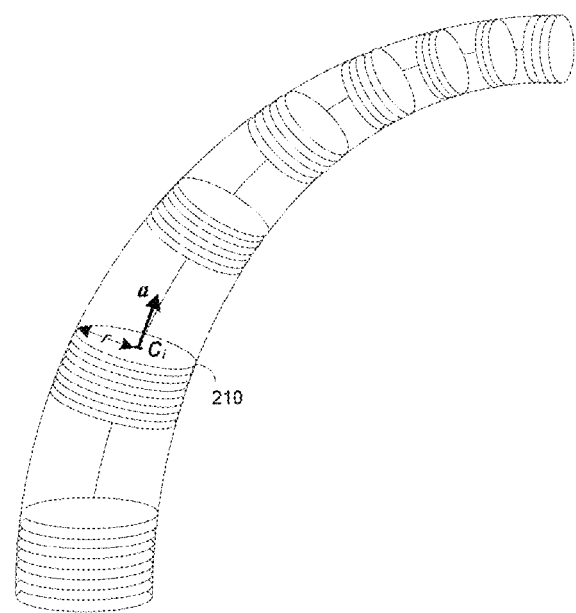
FIG. 2 illustrates a geometrical representation of vessel structure, referred to as the Poker Chip™ representation, in accordance with some embodiments of the technology described herein.

FIG. 2 illustrates a schematic of the Poker Chip™ representation. According to some embodiments, each poker chip 210 is defined by a center location, a radius and an orientation. The center location $c_i$ represents the center of the vessel, for example, determined by centerline filtering, as discussed in further detail below. The radius r represents the radius of the vessel at location $c_i$ and the orientation is the angle of the normal of the poker chip at location $c_i$, and represents the tangent of the centerline of the vessel at location $c_i$. It should be appreciated that the Poker Chip™ representation may include additional parameters, as the aspects of the technology described herein are not limited in this respect.

The inventors have appreciated that the above Poker Chip™ representation may be used to determine characteristics of the vasculature that may help in diagnosing disease, providing information on appropriate treatment, and/or assessing the effectiveness of treatment. For example, since the orientation is known at each location, higher level information such as curvature and tortuosity may be computed, as well as vessel density and distribution measures, as discussed in further detail below. Additionally, since vessel diameter may be determined, vessel size and the change in vessel sizes may be computed as well. Various analyses that can be performed using the Poker Chip™ representation are discussed in further detail below.

To compute some of the higher order information, it may be beneficial to also include in the Poker Chip™ representation information about neighboring poker chips. For example, information about how the poker chips link together may be valuable in understanding the vessel structure as a whole. As discussed above, the inventors have developed algorithms that facilitate linking poker chips together to provide membership information with respect to which poker chips belong to which vessel and information regarding which poker chips are adjacent to one another. After linking has been achieved, more sophisticated vessel analysis may be performed.

Following below is a more detailed description of algorithms capable of extracting geometry from 3D images to obtain a Poker Chip™ representation of vasculature present in the images, in accordance with some embodiments of the technology described herein. While the various algorithms are discussed in connection with detecting and extracting vessel information, the concepts disclosed herein may be applied to detect and associate other structure, as the aspects of the technology described herein are not limited in this respect. In addition, it should be appreciated that distribution analyses according to various aspects of the technology described herein may be applied to information obtained from any vessel image, representation, or combination thereof.

Figure 3A:
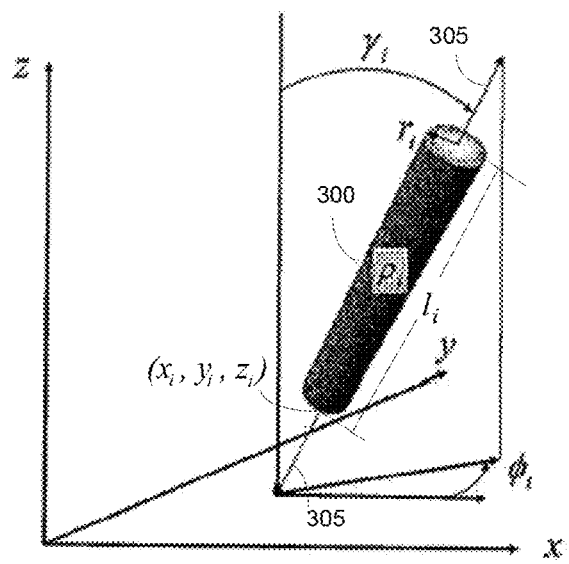
FIG. 3A illustrates a cylindrical segment used to model vessel structure, in accordance with some embodiments of the technology described herein.

FIG. 3A illustrates one example of a cylindrical segment 300 that may be used to generally model a vessel segment. A configuration of cylindrical segment 300 may be described by a number of parameters in a particular coordinate frame. The position of cylindrical segment 300 may be described by a location of the cylindrical axis 305 at a point $(x_i, y_i, z_i)$ in space, for example, the origin or termination of the cylindrical segment. The orientation of cylindrical segment 300 may be specified by the angle $\theta_i$ from the x-axis and the angle $\gamma_i$ from the y-axis. Since cylindrical segment 300 is axially symmetric, its rotation about the z-axis may not need to be specified. The length of the cylindrical segment may be specified by $l_i$ and the radius of the cylindrical segment 300 may be specified by $r_i$.

Figure 3B:
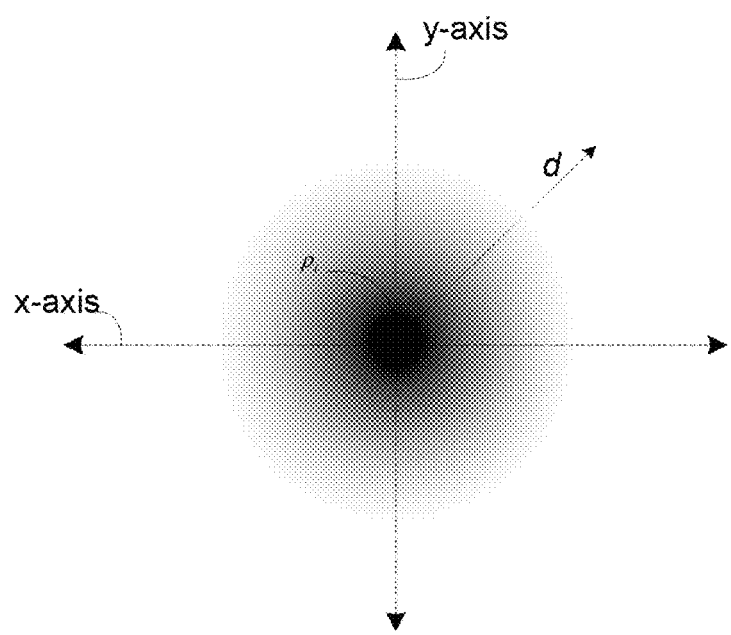
FIG. 3B illustrates a grey scale representation of a characteristic function of a model used to detect vessel structures, in accordance with some embodiments of the technology described herein.
Figure 3C:
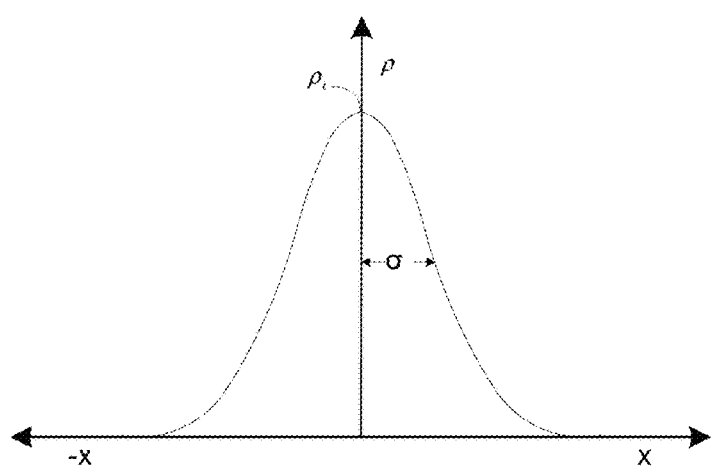
FIG. 3C illustrates a plot of the intensity values along the x-axis at the center of the grey scale Gaussian distribution in FIG. 3B.
Figure 3D:
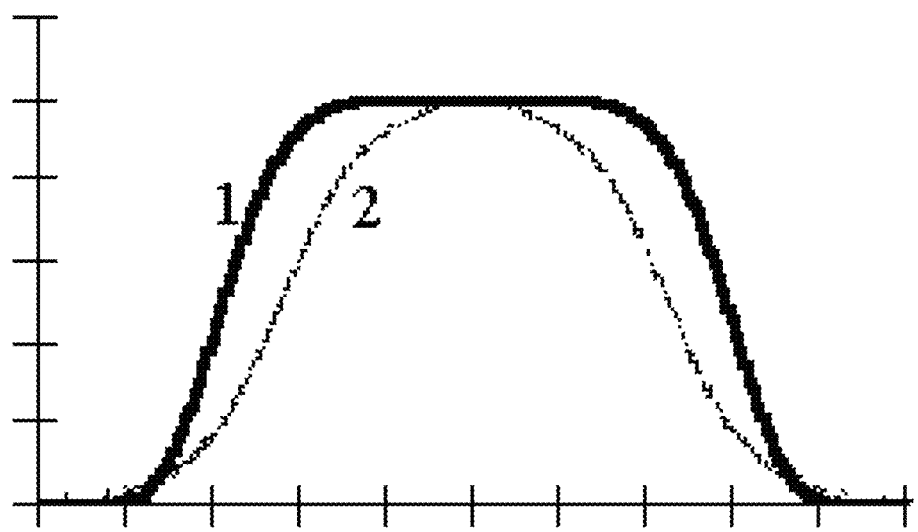
FIG. 3D illustrates a plot of the intensity values along the x-axis of another model of vessel intensity profile.

The inventors have appreciated that the cross-section of a vessel may be characterized by a generally Gaussian shaped intensity distribution. The cross-sectional density of a vessel may be modeled by a Gaussian distribution, centered on the longitudinal axis of the vessel, so that the modeled density is the highest at the center of the vessel. For example, the cross-sectional density distribution of a cylindrical vessel segment, when oriented such that its longitudinal axis coincides with the z-axis, may be modeled as, $$\rho \left( e^{-\frac{1}{r^2}((x-x_i)^2 + (y-y_i)^2)} \right) \quad (1)$$

where $\rho$ is the density coefficient at a center of the cylindrical segment and r is the radius of the cylindrical segment, so that the density is modeled as being greatest at the center (i.e., equal to $\rho$) and decays exponentially as a function of radial distance from the center. FIG. 3B illustrates a grey scale representation of the function given in Eq. (1), where darker grey scale values indicate increased density values. FIG. 3C illustrates a plot of the intensity values along the x-axis at the center of the grey scale Gaussian distribution in FIG. 3B. FIG. 3D illustrates a vessel intensity profile that may better model the intensity profile of vessels in an image. Curve 1 and 2 illustrated vessel profile intensity when vessel diameter is larger than the resolution of the scan and when the vessel diameter is smaller, respectively.

Figure 4:
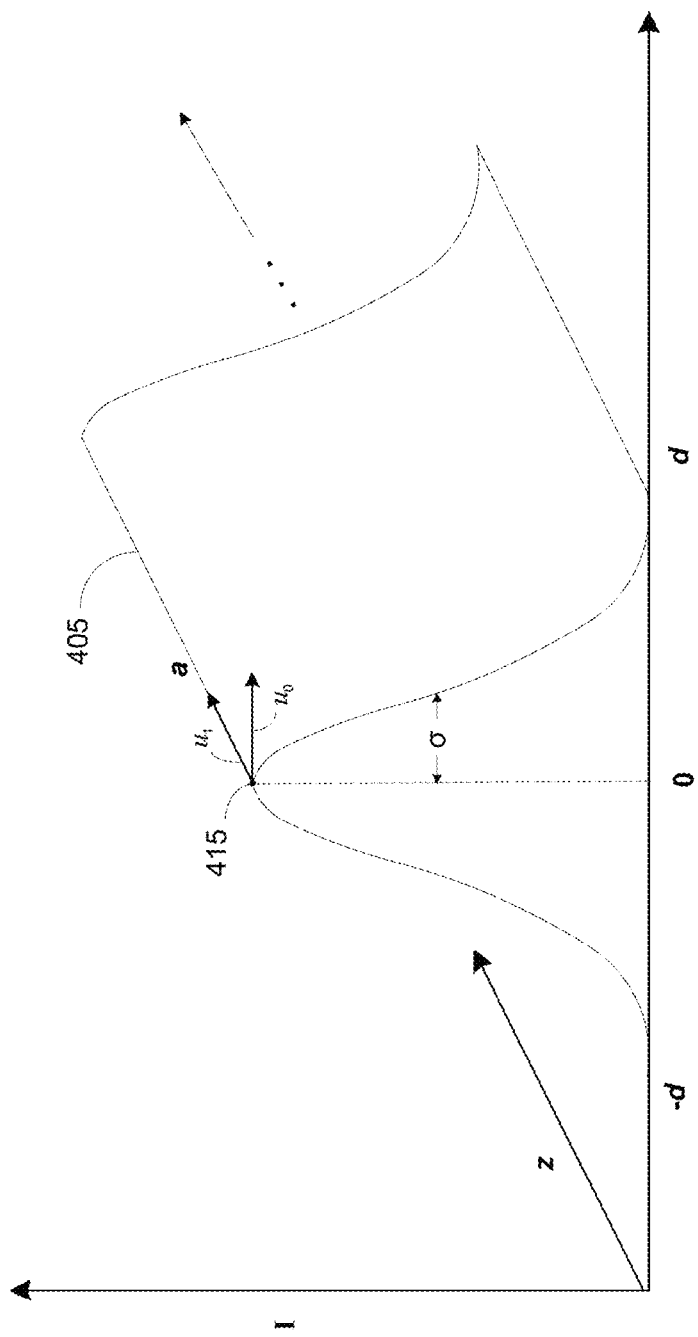
FIG. 4 illustrates schematically a cylindrical vessel segment intensity distribution illustrating a ridge or centerline feature, in accordance with some embodiments of the technology described herein.

The density distribution along the longitudinal axis of the cylinder (i.e., into and out of the page in FIG. 3B) is substantially uniform and does not vary substantially and may be modeled as a constant function of the cross-sectional distribution along the longitudinal axis, that is, as a constant function of the radial distance d from the center of the distribution. FIG. 4 illustrates schematically a cylindrical vessel segment intensity distribution model. In particular, the model of the cylindrical vessel segment has a maximum density at the center that decays exponentially to the boundary of the vessel as a function of the radial distance d, from the center. At each distance d, the density is uniform along the z-axis. For example, the density at d=0 is the density maximum along the length of the vessel. This density maximum shown by line 405 is referred to as a ridge, and corresponds to the centerline of a vessel.

If the herein described characteristic intensity distribution or similar distribution can be identified in the image, the associated pixels/voxels are likely to belong to a vessel. The characteristic points may be used to facilitate segmenting the image into vessel and non-vessel regions. Some methods of detecting the characteristic shape illustrated in FIG. 4 include performing ridge detection on an image. A ridge point is defined herein as a point in an image wherein the intensity assumes a local extrema in the direction of principal curvature, i.e., the direction having the steepest intensity gradient. For example, at point 415 (and along ridge 405) in FIG. 4, the principal direction of curvature is shown by $u_0$ (i.e., the unit vector $(1,0)$ in the $(d, z)$ coordinate frame). Each point along ridge 405 forms a ridge point since each point is a local maximum along the z-axis. Accordingly, a ridge may be characterized by local derivative information in the image and may be detected by examining the curvature of intensity about points of interest in the image.

Some conventional methods have proposed detecting the ridge using the Hessian operator. However, the Hessian operator requires performing second derivatives of the image information, which reduces the signal-to-noise ratio (SNR) and may result in degraded performance. The inventors have developed methods of detecting the characteristic shape of blood vessels described above using centerline filtering techniques that may avoid some of the performance degradations commonly seen with conventional filters such as the Hessian operator, as discussed in further detail below.

As discussed above in connection with FIG. 1, a non-limiting example of a method for extracting geometry from images may include a number of processing blocks including: a scale detector, an orientation detector, centerline filtering, non-maximum suppression and linkage. Briefly speaking, the system works as follows: firstly, the scale detection and orientation detection modules may be applied on 3D images to obtain correct size and orientation parameters for centerline detection (e.g., scale and orientation parameters for the centerline filters); secondly, based on the parameters obtained from scale detection and orientation detection modules, the centerline filter may be applied on every voxel of a 3D image, or applied on a subsection of voxels for which centerline detection is desired. The generated response field formed by applying the centerline filter indicates the likelihood that the associated voxel corresponds to the vessel centerline; finally, non-maximum suppression and linkage is applied on the centerline response field to extract the vessel centerline and obtain a vessel mathematical representation (e.g., a linked Poker Chip™ representation). Following below are more detailed descriptions of embodiments of the five main blocks briefly discussed above, e.g., scale detection, orientation detection, centerline filtering, non-maximum suppression and centerline linking.

Scale Detection

As discussed above, scale detection may be applied to estimate the centerline filter size appropriate for each voxel at which centerline detection is to be applied. Applying scale detection on each voxel of a 3D image volume may be relatively expensive computationally. That is, if each voxel in the 3D image is deemed to be a potential centerline point, then scale detection should be applied to each voxel in the image. However, the inventors have appreciated that since vessels occupy only a portion of the volume, it may not be necessary to detect scale on every voxel. In particular, certain voxels may be eliminated based on the image properties of the voxels, for example, the intensity level of the voxel.

In general, intensities from vessels are higher than those in the background. Using a conservative intensity threshold, voxels may be classified as background voxels with a low false positive rate that can be controlled based on how conservative the threshold operator is set. That is, by setting the threshold conservatively, a substantial percentage of the background voxels may be eliminated from scale detection without the risk of eliminating any vessel voxels. The term "background" refers herein to voxels that are not part of the subject matter of interest that is being detected. By eliminating background voxels, the computations needed to perform scale detection can be reduced. That is, by removing at least some voxels from consideration, scale detection need not be performed on each voxel in the image.

Figure 5:
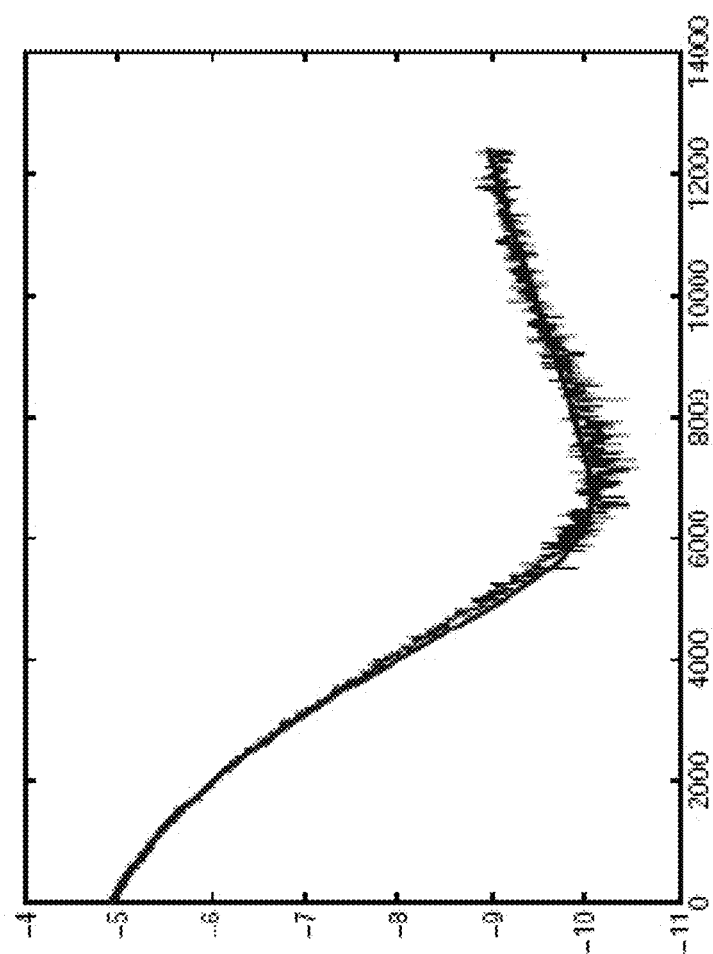
FIG. 5 illustrates an embodiment of a mixture of truncated Gaussian fit to 3D reconstruction intensity data, wherein the vertical axis is in log scale and low part of the horizontal axis is shown.

It is reasonable to model both background intensity and vessel intensities as a Gaussian distribution. In practice, the assumption in FIG. 5 shows that a model using a mixture of truncated Gaussians is a very good fit for the data in low intensity regions. The truncated Gaussian distribution has the Probability Density Function (PDF) as follows:

$$p(I|\mu, \sigma) = \frac{N(I|\mu, \sigma)}{\int_{b_1}^{b_2} N(x|\mu, \sigma)dx} \quad (2)$$

where $N(I|\mu, \sigma)$ denotes a Gaussian distribution with mean $\mu$ and variance $\sigma$, and b1 and b2 are the truncation points. To capture both background and vessel distributions, the mixture of two truncated Gaussians for the data may be expressed as:

$$p(I) = \sum_{c=0}^{1} \sum_{i} \left\{ w_c \, \log \left[ \frac{N_{c(I_i | \mu_c, \sigma_c)}}{\int_{b_1}^{b_2} N_{c(x_i | \mu_c, \sigma_c)} dx} \right] \right\} \quad (3)$$

where $w_c$ is the weight percentage of each component. Directly maximizing the likelihood may become challenging because determining the marginal probability may require computations that increase exponentially with the data. In some embodiments, the problem is solved using an Expectation Maximization (EM) algorithm. The EM process iteratively goes through two steps by soft assignment of data (Expectation) and maximizing the whole likelihood (Maximization). That is, an initial approximate distribution may be used to classify voxels as either background or foreground (e.g., vessels) in the Expectation step. Next, the distribution is refined based on the classification (Maximization) and classification (Expectation) is repeated on the refined distribution. This process may be repeated until the process converges on a final classification of background and foreground voxels.

Applying an EM algorithm on a mixture of Gaussians is only one method by which background voxels may be eliminated from consideration, or by which voxels are classified as background and foreground voxels. Other pre-processing or thresholding techniques may be used to reduce the number of voxels on which further processing is performed to reduce the computational expense, as the aspects of the technology described herein are not limited in this respect. In addition, while voxel intensity may be one suitable parameter to use to perform a conservative elimination of voxels belonging to the background, any suitable parameter may be used, as the aspects of the technology described herein are not limited in this respect. For example, higher order properties may be used.

As discussed above, separating scale detection and orientation detection may have benefits over algorithms that perform the two operations simultaneously. The inventors have designed a scale detection filter which does not depend on the orientation of the structure to be detected. According to some embodiments, an orientation independent filter may be developed such that the filter can be mathematically described in spherical coordinates as f–f(r), which is a function that does not depend on orientation. The symmetry of the filter allows the filter to be independent of how the filter is oriented. To accurately detect centerline voxels from 3D images, the response generated by the scale detection filter should be maximum when it is located at a centerline voxel. The scale $\sigma_r$ at a point (x, y, z) inside a cylinder may be defined as the distance to the wall of the cylinder boundary:

$$\sigma_r(x, y, z) = \text{dist}(x, y, z; \text{wall of the cyclinder}) \quad (4)$$

Figure 6:
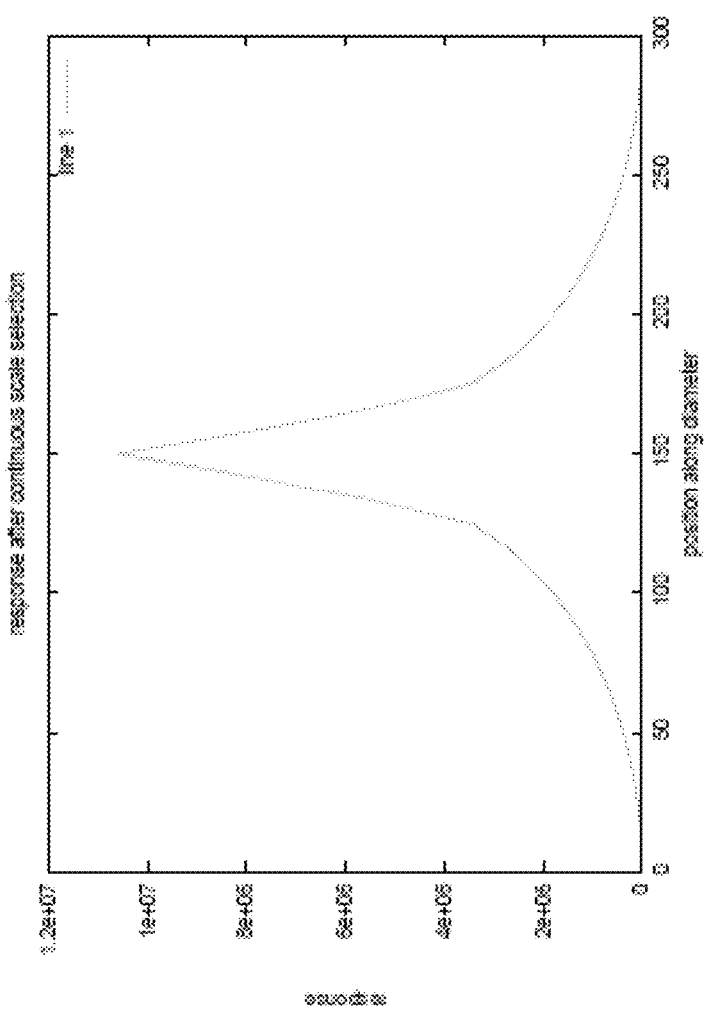
FIG. 6 illustrates an embodiment of a theoretical profile of a centerline filter response using scale detection, in accordance with some embodiments of the technology described herein.

As shown in FIG. 6, this definition of scale guarantees a unique maximum filter response inside the cylinder after scale selection (in the absence of noise). Normally, the intensity of a 3D image outside of a vessel is significantly lower than the intensity inside the vessel. This rapid intensity decay provides an indication of scale. The inventors have developed a rank-based scale filter that is orientation independent. Given a point X inside a vessel, a rank based scale filter may be defined as:

$$\mathcal{R}(X, r) = \frac{f_-(\{I(X^i): |X' - X| = r + 1\})}{\min_r \{f_+(\{I(X'): |X' - X| = 1, \ldots, r\})} \quad (5)$$

where R(X, r) is the filter response at image location X with filter radius r, and f– and f+ are rank functions, respectively. Note that the filter is parameterized by radius only, resulting in filter symmetry that is orientation independent. Given various noise models, there are many ways to choose the rank functions. In order to cope with image reconstruction effects, f– may be chosen as the median value of the last 10 lowest intensities and f+ may be chosen as the median value of the last 10 highest intensities. That is, the rank function may be determined from characteristics of the image. However, the rank functions may be selected to be any value that facilitates detection of scale, as the aspects of the technology described herein are not limited in this respect. The scale $\sigma_r(X)$ may then be obtained by finding the minimum radius r so that R(X, r) reaches the threshold α:

$$\sigma_r(X) = \min_r \left\{ R(X, r) < \frac{1}{\alpha} \right\} \quad (6)$$

Stated differently, the radius of the scale filter is increased until the filter response no longer satisfies the relationship in Eq. (6). As discussed above, the scale detection filter may be designed to be independent of orientation. According to some embodiments, the kernel or shell of the scale filter is a circle in 2D and a sphere in 3D. As a result, the size of the filter is defined by the radius r, where the center of the filter is located at a target voxel at location X in the image. Since the filter has the same radius in all directions, the application of the scale filter is independent of orientation.

Figure 7:
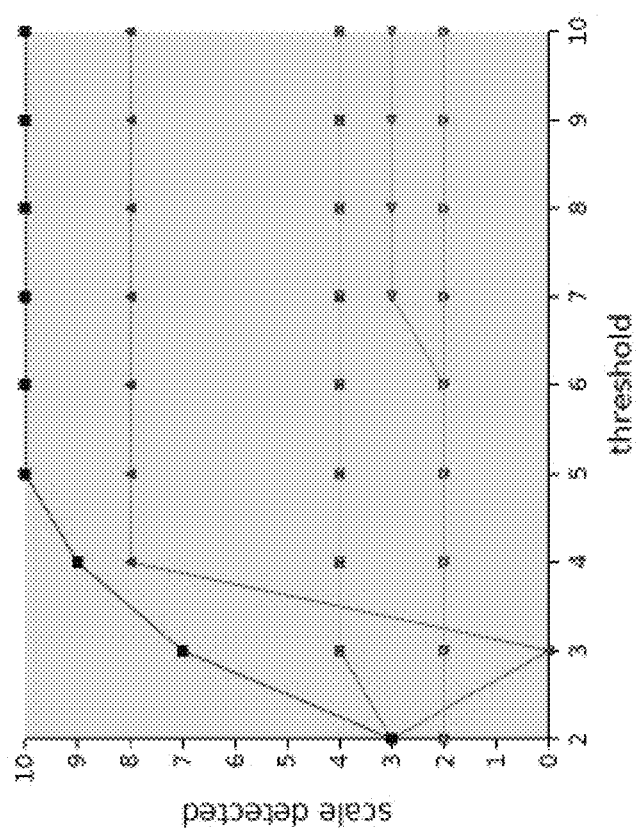
FIG. 7 illustrates an embodiment of a detected scale versus the choice of threshold α.

The criteria for the filter response may be chosen to be any suitable criteria that can robustly determine when the filter kernel has crossed a vessel boundary. The criteria in Eq. (6) is merely exemplary. In some embodiments, the value of α is chosen to be 5. However, other values may be used as well as the aspects of the technology described herein are not limited in this respect. In order to examine the sensitivities of this rank-based scale filter to the choice of the threshold parameter α, a few points inside different vessels may be randomly chosen to see how the selected scale changes depending on the ratio threshold parameter α. FIG. 7 shows that the scale approaches the correct value when α is chosen to be larger than 5.

Figure 8:
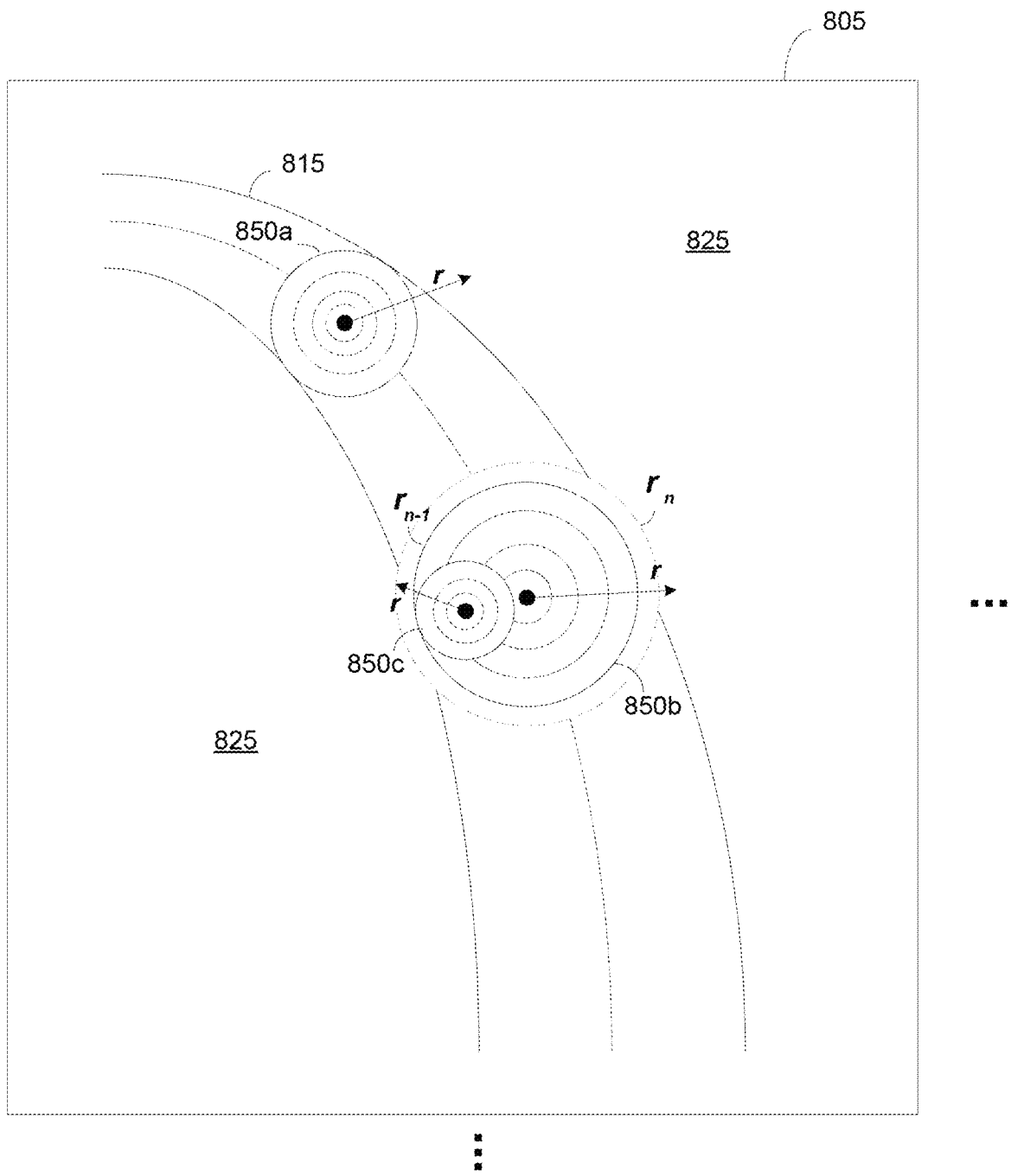
FIG. 8 illustrates an orientation independent scale filter, in accordance with some embodiments of the technology described herein.

FIG. 8 illustrates pictorial an orientation independent scale filter, in accordance with some embodiments of the technology described herein. It should be appreciated that while the scale detection filter in FIG. 8 is shown (and is suitable) in the context of a 2D image for convenience of illustration, the scale detection filter is designed as a 3D filter to detect scale in 3D volumetric images. In particular, the circular filter illustrated in FIG. 8 may be made an expanded to a sphere to detect scale in 3D. In FIG. 8, a portion of an image 805 is shown having a vessel structure 815 within the image portion. It should be appreciated that image portion 805 is schematic and the vessel structure 815 and the background 825 would be comprised of an intensity value at each voxel location in the image portion. Moreover, it should be appreciated that image portion 805 may be a small portion of a much larger image. For the sake of clarity only a single vessel structure is depicted in image portion 805, though the image portion may in reality include any number of vessel structures.

FIG. 8 also illustrates three separate applications of an orientation independent scale filter 850. It should be appreciated that the scale filter 850 may be applied at all of the image voxels or at a selected number of image voxels (e.g., voxels determined to be vessel voxels using a preprocessing techniques such as the intelligent thresholding method described above). The three applications of the filter in FIG. 8 are merely exemplary and are chosen at arbitrary locations to assist in describing the scale detection filter. Each application of the filter begins by placing the filter with a predetermined minimum radius r on a target pixel at which scale is being detected. The scale filter is then applied to the image, for example, by convolving the image pixels that fall under the filter kernel or support with the values of the filter kernel. If a certain criteria is met, the filter is assumed to still be entirely within the vessel and the radius r is increased.

In FIG. 8, the increasing of the filter radius is depicted by the successively larger circles in dashed line. The circles in solid line denote the last filter applied such that the criteria was met. For example, the dotted line circle in filter application 850b shows a circle of $r_n$ that when applied to the underlying image failed to meet the criteria, where n is the number of successively larger radius filter kernels that have been applied to the image. Thus, the scale at the corresponding image location is determined to be $r_{n-1}$. Not only does scale detection provide the appropriate scale to be used in subsequent filtering processes (e.g., centerline detection), it also may indicate the radius of the vessel structure in the Poker Chip™ representation.

The inventors have used the fact that the intensity of voxels within the vessel, in the absence of noise, is substantially higher than the background voxels to establish the criteria such that the criteria will not generally be met when the filter kernel is extended outside the vessel structure. One embodiment of such a criteria is described in Eq. 5 and Eq. 6. By employing the rank functions illustrated in Eq. 5, and using the criteria in Eq. 6, a robust filter may be designed that will fail to meet the criteria when the filter kernel is increased in size such that it encompasses voxels outside of the vessel. However, the above described scale detection filter is exemplary and other scale detection filters may be used, as the aspects of the technology described herein are not limited in this respect. In addition, any criteria that tends not to be met as a filter is expanded across a vessel boundary may be used, as the aspects of the technology described herein are not limited in this respect.

Because the centerline voxels are not known a priori, the scale detection filter may be applied to non-centerline voxels. As shown by filter application 850b, the scale detection is again stopped when the filter kernel crosses the vessel boundary. Because the target voxel is not a centerline voxel, the radius of the filter will not correspond to the radius of the vessel. However, this may be inconsequential because voxels that are not determined to be centerline voxels are removed in subsequent processing, such as during centerline filtering discussed below. Because only voxels detected as centerline voxels will survive centerline filtering, the radius of the scale detector may accurately reflect the radius of the associated vessel.

Figure 9:
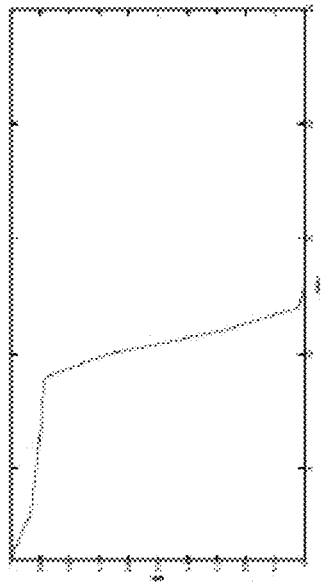
FIG. 9 illustrates an embodiment of how R(X, r) behaviors on real images—(a) a slice of 3D images is shown and blue point is the point X where we apply rank-based scale filter—(b) the rank-based scale filter's response with different radius is shown—although the intensities have large variation inside vessel, the rank-based scale filter behavior smoothly and have a rapidly decay while cross the boundary of the vessel.
Figure 9:
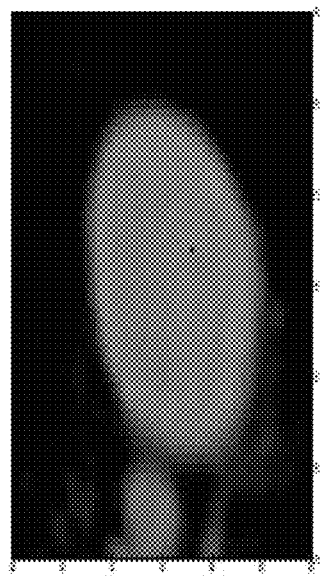
Figure 11:
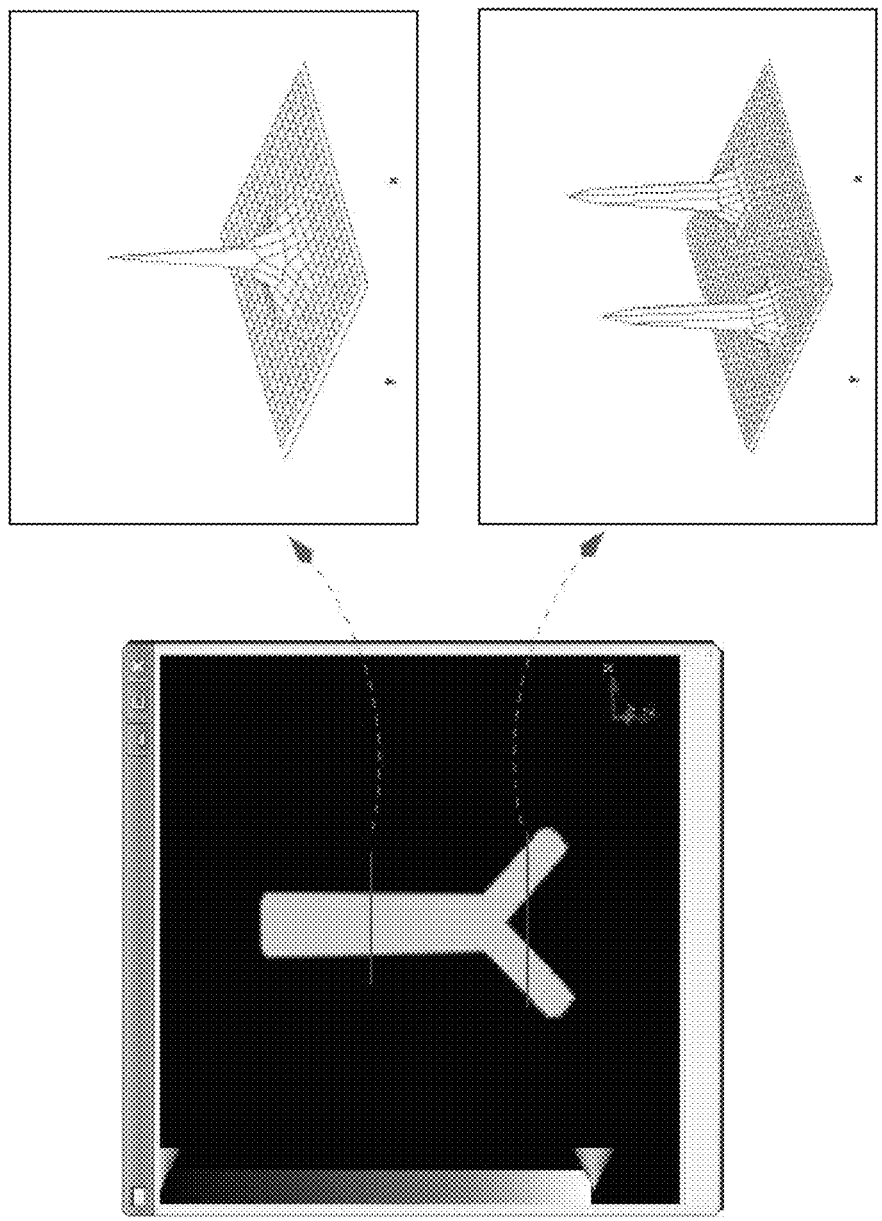
FIG. 11 illustrates centerline filtering on a 3D volume data set, in accordance with some embodiments of the technology described herein.

FIG. 9 shows what R(X, r) looks like when it is applied on real images. Although the intensities have large variation inside the vessel, the rank-based scale filter behaves smoothly and decays relatively rapidly across the boundary of the vessel. Thus, rank-based scale filters may have the generally beneficial property of relatively distinct response change as the filter crosses vessel boundaries, and is relatively stable and insensitive to the choice of ratio parameter. Accordingly, scale may be detected at each selected voxel in the image. For example, scale may be detected at each voxel in the image or the reduced number of voxels resulting from performing thresholding on the image to eliminate at least some of the background voxels. The selected voxels at which scale detection is performed can be selected in other ways, as the aspects of the technology described herein are not limited in this respect.

Orientation Detection

As discussed above, centerline filtering may be improved by first determining the orientation at which the centerline filter should be applied. Since scale is detected independent of orientation, orientation detection may be performed separately from scale detection and, in some embodiments, orientation detection uses the scale values detected during scale detection to improve detection of the orientation of the subject matter of interest. In some embodiments, a gradient based orientation detection algorithm may be used, however, other algorithms may be used to detect vessel orientation, as the aspects of the technology described herein are not limited in this respect. Because of the rotational symmetry along the axis of a cylinder on which the vessel structure may be modeled, the intensity along a line parallel to the vessel axis is constant in the absence of noise. In other words, the directional derivative of intensity along the direction v parallel to the vessel axis is zero in the absence of noise:

$$v \cdot \nabla \rho(X) = 0 \quad (7)$$

It should be appreciated that x-ray decay during image acquisition depends on its penetrating length. Thus, the intensity inside a vessel tends to vary along any direction other than the axis direction. This fact indicates that Eq. (7) may be a necessary and sufficient condition for finding the vessel direction since the above argument holds for any point X inside the vessel. Therefore, the direction of a small cylinder segment at each point X can be estimated by finding a direction vector a along which the intensities have the least change. However, direct estimation from the derivative of one point X tends to be error prone. In some embodiments, all the derivatives inside a small volume centering on the point X may be used to increase the accuracy. To be more precise, the axis direction â may be estimated by finding a direction that minimizes the sum of the directional intensity gradient along this direction:

$$\hat{a} = \arg\min_{a} \left\{ \iiint_{v} \| a \cdot \nabla \rho(x, y, z) \| \, dx\,dy\,dz \right\} \quad (8)$$

where σ(X) is the scale detected at point X and $\|\cdot\|$ is the norm discussed herein. In the presence of noise, a directional gradient of intensity convolved with an adaptive Gaussian kernel may be used, as follows.

$$\hat{a} = \arg\min_{a} \left\{ \iiint_{v} \| a \cdot \nabla (G_{\sigma(x,y,z)} \circ \rho(x, y, z)) \| \, dx\,dy\,dz \right\} \quad (9)$$

In some embodiments, Eq. (9) can be solved by a least square estimation by assuming the noise distribution is Gaussian i.i.d, i.e., the norm in Eq. (9) is an L2-norm. However, it is well known that an L2-norm may be sensitive to outliers present in the input data, and outliers may frequently appear in reconstructed 3D images. In some embodiments, a L1-norm in Eq. (9) may be used.

$$\hat{a} = \arg\min_{a} \left\{ \int\int\int_{v} \| a \cdot \nabla(G_{\sigma(x,y,z)} \circ \rho(x, y, z)) \|_1 \, dxdydz \right\} \quad (10)$$

$$\arg\min_{a} \left\{ \int\int\int_{v} \| a \|_1 \cdot \| \nabla(G_{\sigma(x,y,z)} \circ \rho(x, y, z)) \|_1 \, dxdydz \right\} \quad (11)$$

To avoid the trivial solution at a=0 in the above equation, the constraint $\Sigma_i \|a_i\|_2 = 1$ may be used. Since a is independent of the point (x, y, z), a is moved out of the triple integral so that:

$$\tilde{a} = \min_{a} \left\{ \| a \cdot \underbrace{\int\int\int_{v} \nabla(G_{\sigma(x,y,z)} \circ \rho(x, y, z)) dxdydz}_{M} \|_{L2} \right\} \quad (12)$$

$$\text{s.t.} \left\{ \sum_{i} \|a_i\|_2 = 1 \right\}$$

It should be appreciated that in Eqs. (8)-(12), the operation is being performed over a volume v. By performing orientation detection over a neighborhood, rather than at a single voxel, semi-global information may be captured in the orientation assessment. The neighborhood information allows for robust orientation detection in the presence of noise and outliers. However, it should be appreciated that the neighborhood (e.g., the volume v) may be different for detecting direction in relatively large vessels versus relatively small vessels. Accordingly, the inventors have developed an adaptive method that varies the size of the neighborhood based on the scale at a target voxel. That is, the scale determined during scale detection may be used to determine the size of the volume v. In some embodiments, the size of $(2\lfloor s+2 \rfloor +1)$ may be used as the size of volume. However, any adaptive neighborhood based on scale may be used, as the aspects of the technology described herein are not limited in this respect. Thus, the size of the neighborhood used for orientation detection may be adapted according to the scale of the image at each location.

As discussed above, and L1-norm may be used to address outliers. There are a number of ways to solve Eq. (12). In some embodiments, the equation is solved by constraint optimization using Lagrange multipliers. Applying Lagrange multipliers to the above equation obtains:

$$\nabla_a(a^T M^T M a + \lambda a^T a) = 0$$

$$(M^T M)a + \lambda a^T = 0 \quad (13)$$

Therefore the center line direction, a, may be obtained by computing the eigenvector associated with the smallest eigenvalues of matrix M. Referring back to FIG. 4, solving the above equations to determine the direction a can be pictorial explained. In general terms, the eigenvectors of matrix M indicate the characteristic directions of curvature. The relationship between these characteristic directions of curvature may be employed to identify the direction of the centerline. The eigenvalues and associated eigenvectors of a matrix may be determined in various ways, for example, by any number of well-known iterative methods of diagonalizing a matrix or analytically by directly solving the relationship:

$$Mu = \lambda u \quad (14)$$

where M is the matrix of Eq. 13, u is an eigenvector of matrix M, and $\lambda$ is an eigenvalue associated with u. The magnitude of each eigenvalue of the matrix M is related to the "significance" of the associated eigenvector. Stated differently, the eigenvalue indicates how much the curvature along the associated eigenvector contributes to the local curvature determined by the matrix M. Accordingly, a in Eq. 13 is the eigenvector associated with the smallest eigenvalue and indicates the direction in which the change in intensity is the smallest. The largest eigenvalue of the matrix M is associated with the principal direction of curvature.

In FIG. 4, the linearly independent eigenvectors $u_0$ and $u_1$ (i.e., eigenvectors $u_0$ and $u_1$ are orthogonal) are shown on the illustrated intensity curve. The eigenvalue $\lambda_0$ herein denotes the eigenvalue having the greatest absolute value and is referred to as the principal eigenvalue. Accordingly, the associated eigenvector $u_0$ indicates the principal direction of curvature at a target pixel and $\lambda_0$ is related to the magnitude of the curvature. The eigenvalue $\lambda_1$ (referred to as the secondary eigenvalue) is related to the magnitude of curvature in the direction of $u_1$, i.e., in a direction orthogonal to the principal direction of curvature indicated by $u_0$. Along the ridge of the Gaussian profile (i.e., in the direction $u_1$), the intensity should be substantially zero and the change in intensity relatively small and in the noiseless case is zero (i.e., the intensity does not change as a function of z in the direction of the centerline). Accordingly, by determining the eigenvector associated with the smallest eigenvalue, the direction a which corresponds to the direction of the centerline may be determined. Thus, the orientation of the centerline may be determined at each of the selected voxels.

Centerline Detection

Having determined scale and orientation for the feature detection filter, the feature of interest may be detected. According to some embodiments, centerline detection is performed using a Gaussian centerline filter. For example, assume the density inside the vessel satisfies the Gaussian model:

$$I(r) = I_0 e^{-\frac{r^2}{2\sigma^2}} \quad (15)$$

Here, r is in the direction perpendicular to the vessel axis; $\sigma$ is the radius of the vessel; and $I_0$ is the intensity at the center. In order to detect a Gaussian vessel, a filter with radial variation corresponding to the 2nd derivative of the Gaussian may be used:

$$h(r) = \left(\frac{r^2}{\sigma^2} - 1\right) e^{-\frac{r^2}{\sigma^2}} \quad (16)$$

The application of this filter corresponds to a volume integral over space. This volume integral should vanish if the filter is embedded in material with constant density. However the 2nd derivative of the Gaussian does not, i.e., $$\int_0^\infty \left(\frac{r^2}{\sigma^2} - 1\right) e^{-\frac{r^2}{\sigma^2}} r \, dr = 1 \quad (17)$$

This problem can be fixed by adding an offset, $$\int_0^\infty \left(\frac{r^2}{\sigma^2} - 2\right) e^{-\frac{r^2}{\sigma^2}} r \, dr = 0 \quad (18)$$

Therefore, the centerline filter has the form $$f(r) = \frac{e}{4\Pi\sigma^2}\left[2 - \left[\frac{r}{\sigma}\right]^2\right] e^{-\frac{r^2}{2\sigma^2}} \quad (19)$$

This filter has a positive core when $r<\sqrt{2}\sigma r<$ and negative shell when $r>\sqrt{2}\sigma$.

The inventors have appreciated that in the presence of noise, a centerline filter that closely mimics the shape of a Gaussian as described above may at times be inaccurate, especially in situations where vessel structures are relatively close together. In particular, the continuous decay of the Gaussian may incorrectly detect or fail to detect centerline voxels in certain situations, such as when vessel structures are close together and/or in circumstances where relatively small vessel structures appear nearby relatively large vessel structures.

The inventors have appreciated that a modified centerline filter may be more effective at accurately identifying centerline points, particularly in the presence of noise. According to some embodiments, centerline detection is performed using a filter that better matches the profile of vessel structures in an image. FIG. 10A illustrates a matched filter in accordance with some embodiments of the technology described herein. Filter 900 includes an inner core and an outer core. Rather than a Gaussian kernel, filter 900 includes a step function between the inner and outer core. As a result, the filter support is more compact and the filter is able to more accurately detect vessel structures that are close together. In addition, because the filter better matches vessel profiles, centerline detection may be more accurate. An example of values assigned to the matched filter 900 according to some embodiments include:

$$f_s(r, z) = \begin{cases} 1 & r \leq s \text{ and } z \leq \sqrt{2}\, s \\ 0 & s < r \leq \sqrt{2}\, s \text{ and } z \leq \sqrt{2}\, s \\ -1 & r > \sqrt{2}\, s \text{ or } z > \sqrt{2}\, s \end{cases} \quad (20)$$

Figure 12:
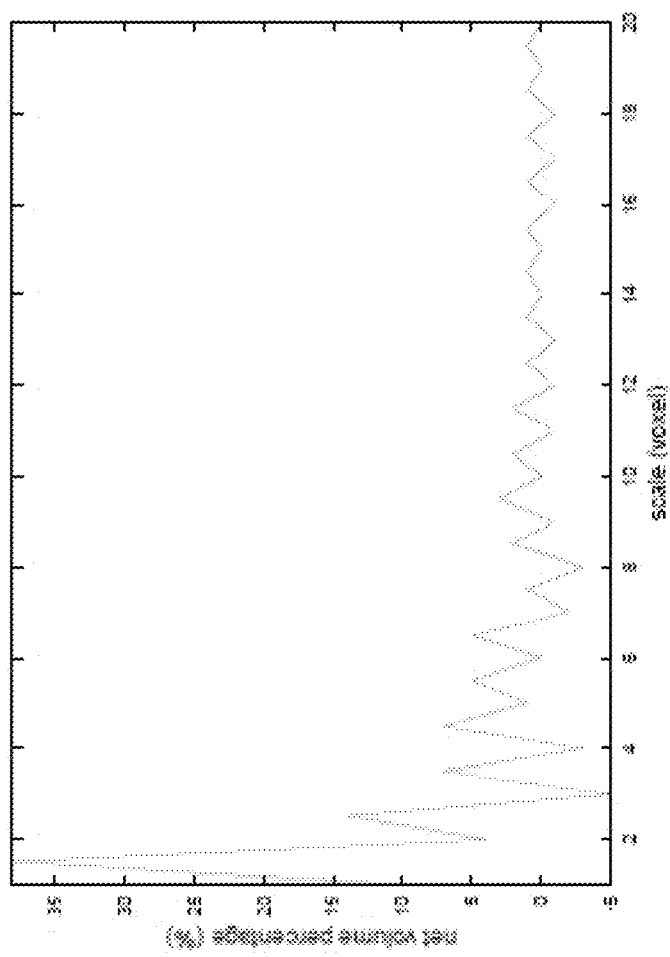
FIG. 12 illustrates net volume of the center line filter versus different scales.

An illustration of the profile of the above filter along the axis x-x' is shown pictorially in FIG. 10B. As shown, the size of the matched filter is based on the scale s detected during scale detection. Applying this filter, the centerline response may be given as:

$$r(x, y, z) = \iiint T[f(r, z)G(0, \sigma)]I(x, y, z)dxdydz \quad (21)$$

where $G(0, \sigma)$ is a Gaussian smooth kernel. When the scale of the filter is small (e.g., when scale detection determines that the local scale is relatively small), the filter defined by Eq. (20) may not have a zero net volume (volume of the positive core minus the volume of the negative core). This may cause detection difficulties because the filter may have non-zero response when applied to a non-zero uniform background. As shown in the FIG. 12, when the scale of the filter is small, the net volume percentage may be quite large. For example, for a centerline filter with scale of 1.5, the net volume is 35% of the total volume of the filter. Thus, the filter may generate filter bias in the favor of small scale.

Therefore, to address this bias the filter described above may be modified as:

$$f_s(r, z) = \begin{cases} 1 & r \leq s \text{ and } z \leq \sqrt{2}\, s \\ 0 & s < r \leq \sigma(s) \text{ and } z \leq \sqrt{2}\, \sigma(s) \\ -\omega_s & r > \sigma(s) \text{ or } z > \sqrt{2}\, \sigma(s) \end{cases} \quad (22)$$

where, $$\sigma(s) = \begin{cases} \sqrt{2}\, s + 0.5 & \text{if } s < 10 \\ \sqrt{2}\, s & \text{otherwise} \end{cases} \quad (23)$$

and $w_s$ is a function of scale s so that, $$\iiint_{r>\sigma(s) \text{ or } s>\sqrt{2}\sigma(s)} w_s dxdydz = \iiint_{r \leq s \text{ and } z \leq \sqrt{2}s} dxdydz \quad (24)$$

An illustration of the profile of the filter expressed in Eq. (22) along the axis x-x' is shown pictorially in FIG. 10C. The matched filters described above may be particularly effective at accurately detecting centerline voxels in the presence of noise and in circumstances when subject matter of interest is positioned in close proximity to each other.

The matched filters described above may be applied to a plurality of selected voxels in the image. Accordingly, for each selected voxel at which the matched filter is applied, there will be an associated filter response indicative of the likelihood that the corresponding voxel is a centerline voxel. However, only the maximum filter responses may be of interest. That is, the maximum filter responses are those that are most likely to be centerline voxels. Accordingly, filter responses that are not maximum may be suppressed such that only those voxels having maximum filter responses remain.

Non-Maximum Suppression

In some embodiments, non-maximum suppression may be performed. For example, after centerline filtering, each voxel has a response. The response on each voxel indicates how likely it is that the voxel is a centerline voxel. Since the center line voxel should have the maximum response in the plane perpendicular to the axis, the purpose of non-maximum suppression is to suppress non-maximum responses to eliminate non-centerline voxels. On each voxel, a cutting plane perpendicular to the vessel axis may be used to suppress the non-maximum responses. On the cutting plane, only local maximums of centerline filter responses are kept and all other responses are suppressed. Interpolating the centerline location in order to achieve sub-voxel accuracy is described below.

In some embodiments, location interpolation on the cutting plane may be performed. After obtaining the direction of the cylinder, a cutting plane perpendicular to this direction may be used to apply the non-maximum suppression as an analog to the traditional computer vision edge detection problem. Given an arbitrary voxel x, the voxel x may be tested to determine whether the voxel is a local maxima. According to some embodiments, the cutting plane may be centered on x and the centerline response R(x) may be compared with any other responses in its cutting plane neighborhood $N(x, v_x)$. That is, the response field in the neighborhood N (e.g., a 3×3×3 neighborhood) may be projected onto this cutting plane. If the response at voxel x is larger or equal to all of the responses of neighborhood voxel, voxel x may be labeled as a local maxima. Otherwise, voxel x is labeled as a non-maxima voxel and suppressed. This test may be expressed as:

$$IsMaxima(x) = \begin{cases} true & R(x) \geq R(y), \forall\, y \in \mathcal{N}(x, v_x) \\ false & otherwise \end{cases} \quad (25)$$

where N(x,vx) denotes the cutting plane neighborhood of the point x. Once the neighborhood is determined, the parabolic function as shown below may be used to interpolate the sub-voxel maximum location.

$$r(x, y) = ax^2 + by^2 + cxy + dx + ey + f \quad (26)$$

Given the above response model and the centerline filter responses in a small region around the center, the following equations may be used:

$$an^2 + bm^2 + cmn + dn + em + f = r(n, m)$$

$$a(n-1)^2 + bm^2 + cm(n-1) + d(n-1) + em + f = r(n-1, m)$$

$$a(n-1)^2 + bm^2 + cm(n-1) - d(n-1) - em + f = r(1-n, -m)$$

$$an^2 + bm^2 + cmn - dn - em + f = r(-n, -m) \quad (27)$$

This linear form can be written as a matrix form $$A \begin{bmatrix} a \\ b \\ c \\ d \\ e \\ f \end{bmatrix} = \begin{bmatrix} r(n, m) \\ r(n-1, m) \\ \vdots \\ r(1-n, -m) \\ r(-n, -m) \end{bmatrix} \quad \text{where} \quad (28)$$

$$A = \begin{bmatrix} n^2 & m^2 & mn & n & m & 1 \\ (n-1)^2 & m & m(n-1) & n-1 & m & 1 \\ \vdots & \vdots & \vdots & \vdots & \vdots & \vdots \\ n^2 & m^2 & m(n-1) & 1-n & -m & 1 \\ n^2 & m^2 & mn & -n & -m & 1 \end{bmatrix} \quad (29)$$

The maximum location is determined by the stationary condition $$\frac{\partial r}{\partial x} = \frac{\partial r}{\partial y} = 0.$$

That is, $$2ax + cy\_d = 0$$

$$cx + 2by + e = 0 \quad (30)$$

Therefore, $$\begin{bmatrix} x \\ y \end{bmatrix} = -\begin{bmatrix} 2a & c \\ c & 2b \end{bmatrix}^{-1} \begin{bmatrix} d \\ e \end{bmatrix} \quad (31)$$

$$= \frac{1}{4ab - c^2} \begin{bmatrix} -2b & c \\ c & -2a \end{bmatrix} \begin{bmatrix} d \\ e \end{bmatrix}$$

$$= \begin{bmatrix} \frac{ce - 2bd}{4ab - c^2} \\ \frac{cd - 2a\varepsilon}{4ab - c^2} \end{bmatrix}$$

In some embodiments, the size of the neighborhood N(x,vx) is determined based characteristics of the image in the neighborhood. There is a natural question of how big the neighborhood size should be chosen in the non-maximum suppression algorithm. In some embodiments, the smallest size of 3×3×3 may be used, but this choice may cause outliers to survive non-maximal suppression in noisy regions. An alternative method of choosing the parameter is to use the results from radius and/or scale detection. In some embodiments, to avoid suppressing real vessels which are close to each other, a conservative approach may be used when choosing the neighborhood:

$$n = 2\left\lfloor \frac{s}{\sqrt{2}} \right\rfloor = 1 \quad (32)$$

It should be appreciated that the neighborhood in Eq. (32) is exemplary and an adaptive neighborhood, for example, based on scale may be determined in other ways, as the aspects of the technology described herein are not limited in this respect.

Generating a Linked Representation of a Vessel Network

As discussed above, information obtained from one or more images of a vessel network may be used to generate an unlinked representation of the vessel network. The unlinked representation may comprise one or more geometric objects (e.g., Poker Chips™) each of which represents a cross-section of a vessel segment in the vessel network. Each of the geometric objects may represent a centerline voxel (e.g., when the geometric object is a Poker Chip™, the center location of the Poker Chip™ corresponds to a centerline voxel). An unlinked representation of the vessel network may be obtained based on output from centerline filtering and non-maximum suppression processes, which provide a 3D field in which each point is marked as either belonging to or not belonging to a centerline. The centerline points may be associated with other information such as radius, strength and orientation (e.g., using the Poker Chip™ representation).

However, without further processing, an unlinked representation of a vessel network does not by itself provide a notion of adjacency or vessel membership, which may be useful in performing analysis of vessel structure in the vessel network. Accordingly, in some embodiments, an unlinked representation of a vessel network may be processed to generate a linked representation of the vessel network. The linked representation may comprise information indicating structure of individual vessel segments (e.g., what centerline voxels belong to which vessel segments) as well as how the vessel segments connect to one another.

In some embodiments, the linked representation comprises a plurality of geometric objects (e.g., Poker Chips™) along with information indicating how the geometric objects are linked to create linked representations of vessel segments in the vessel network. In some embodiments, a linked representation of a vessel network comprises a vessel network structure graph that represents the connectivity of vessel segments in the vessel network. An edge in the vessel network structure graph may represent a vessel segment and a vertex in a vessel network structure graph may represent an intersection of two vessel segments in the vessel network (e.g., at a branch point).

Figure 20:
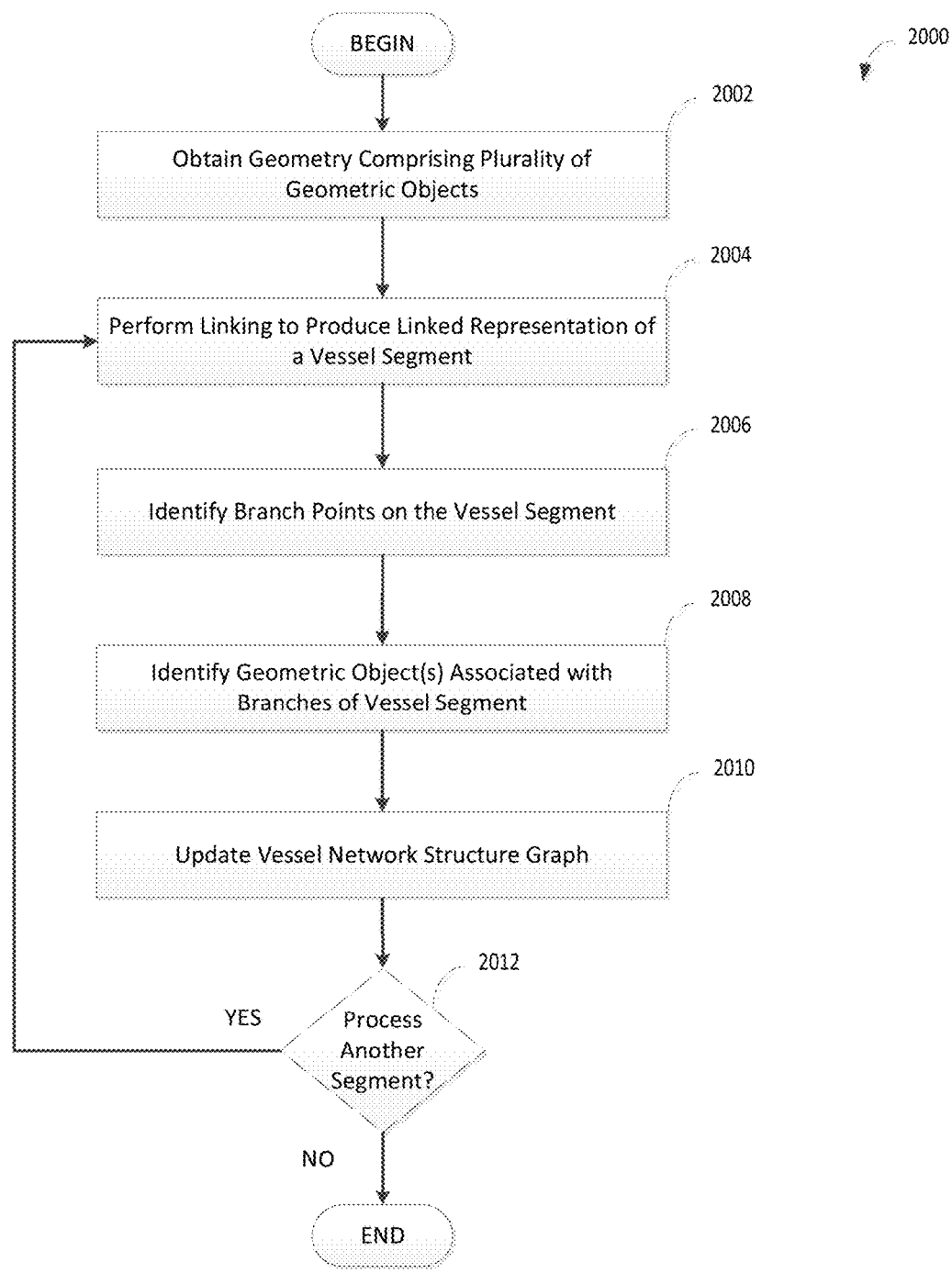
FIG. 20 is a flowchart of an illustrative process for generating a linked representation of a vessel network, in accordance with some embodiments of the technology described herein.

FIG. 20 is a flowchart of illustrative process 2000 for generating a linked representation of a vessel network, in accordance with some embodiments. Process 2000 may be executed using any suitable system and, for example, may be executed using computer system 2800 described below with reference to FIG. 28.

Process 2000 begins at act 2002 where an unlinked representation of a vessel network is obtained. For example, in some embodiments, a geometry comprising a plurality of geometric objects may be obtained, where each geometric object (e.g., a Poker Chip™) represents a cross-section of a vessel segment in the vessel network, as described above. The geometric objects may be obtained in any suitable way (e.g., the Poker Chips™ may be obtained in any of the ways described herein).

Next, process 2000 proceeds to act 2004, where a linked representation of a vessel segment is generated. In some embodiments, an initial geometric object (e.g., a prominent Poker Chip™, such as a Poker Chip™ with a relatively large radius) is identified and one or more other geometric objects are linked to the initial geometric object to form a linked representation of a vessel segment, whereby the linked geometric objects represent cross-sections of the vessel segment. The linking may be performed in accordance with process 2100 described below with reference to FIG. 21, or in any other suitable way.

Next, process 2000 proceeds to act 2006, where the linked representation (of the vessel segment) obtained at act 2004 is further processed to identify branch points on the vessel segment. This may be done in any of the ways described below including, but not limited to, using processes 2200, 2300 and 2500 described below with reference to FIGS. 22, 23, and 25, respectively. Identifying a branch point on the vessel segment may comprise identifying the location of the branch point on the segment as well as identifying the type of the branch point.

Next, process 2000 proceeds to act 2008, where one or more geometric objects that represent a vessel branch (i.e., another vessel segment branching off of the vessel segment whose representation was analyzed at act 2006 to identify one or more branch points) are identified for each of one or more of the branch points identified at act 2006. In some embodiments, one or more unlinked geometric objects may be identified (e.g., one or more Poker Chips located in a neighborhood of a branch point and having large radii) as representing a vessel branch. In some embodiments, one or more linked geometric objects providing a linked representation of the vessel branch may be identified (such a representation may be produced, for example, as part of the process for identifying a branch point, as described in more detail below). In any case, the geometric objects that represent a vessel branch may be used subsequently to perform further processing on the vessel branch (e.g., perform linking or further linking, identify branch points etc.).

Next, process 2000 proceeds to act 2010, where the vessel network structure graph may be updated based on results of acts 2004-2006. In some embodiments, the graph may be updated to have a vertex for each branch point identified at act 2006 and an edge between any two vertices representing branch points connected by a single vessel segment. For example, if a single vessel segment were identified, at act 2006, as having M consecutive branch points (where M is an integer greater than or equal to 1), the graph may be updated to have a vertex for each of the M branch points and an edge between vertices representing branch points that are adjacent on the vessel segment.

Next, process 2000 proceeds to decision block 2012 where it is determined whether another segment (e.g., one or more segments branching off of the vessel segment processed at acts 2004-2010) is to be processed further. This determination may be made in any suitable way. For example, it may be determined that another segment is to be processed when a segment branching off of the vessel segment has not been itself processed to identify branch points thereon. When it is determined at decision block 2012 that no other segment is to be processed, process 2000 completes.

On the other hand, when it is determined that another segment (e.g., a branch of the vessel segment analyzed at acts 2004-2010) is to be processed, a representation of the segment to be processed is obtained (e.g., one or more geometric objects representing the segment to be processed as may have been obtained at act 2008), and process 2000 returns via the "YES" branch to act 2004, at which point acts 2004-2010 are repeated. The segments to be processed may be identified in any suitable way. In some embodiments, each branch of a vessel segment is selected to be processed before any branch of a branch of the vessel segment is selected to be processed—a breadth-first-search type approach. In some embodiments, a branch of a vessel and all its sub-branches are selected to be processed before any other branch of the vessel segment is selected—a depth-first search type approach.

Linking

As discussed above, generating a representation of a vessel network may comprise generating a linked representation of one or more vessel segments in the vessel network by linking centerline voxels (e.g., center locations of Poker Chips™) to identify which centerline voxels are adjacent and determine the vessel segments to which the centerline voxels belong. Accordingly, in some embodiments, generating a linked representation of a vessel segment may be performed by linking geometry extracted from one or more images (e.g., obtained via CT scan, Magnetic Resonance Imaging, Optical Coherence Tomography, etc.). The geometry may include a plurality of geometric objects (e.g., Poker Chips™) each of which represents a cross-section of a vessel segment. Linking the geometric objects, by associating groups of the geometric objects with vessels and determining which geometric objects are adjacent to one another, provides a linked representation of one or more vessel segments in the vessel network. Each of the geometric objects may represent a centerline voxel (e.g., when the geometric object is a Poker Chip™, the center location of the Poker Chip™ corresponds to a centerline voxel).

In some embodiments, the geometric objects may be linked according to a criteria that includes one or any combination of minimizing a distance, a direction change, a radius change, and/or a filter response change from a geometric object to an adjacent geometric object. That is, when selecting between a number of candidate geometric objects to link to a target geometric object, the geometric object candidate that creates the smallest change in one or more of the above parameters may be preferred over candidate centerline geometric objects creating larger changes.

Accordingly, in some embodiments, each of the geometric objects in the geometry extracted from one or more images may be associated with one or more parameter values. In turn, these parameter values may be used to determine how to link the geometric objects to produce a linked representation of a vessel segment. For example, each geometric object may be associated with one or more location values indicative of its location (e.g., a Poker Chip™ may be associated with one or more values indicating the location of its center, which corresponds to a centerline voxel), and the location values of geometric objects may be used to determine how they should be linked (e.g., geometric objects closer to one another are more likely to be linked than geometric objects that are farther apart). As another example, each geometric object may be associated with one or more direction/orientation values (e.g., a Poker Chip™ may be associated with one or more values indicating the orientation of the centerline at the location of the Poker Chip™), and the direction/orientation values of geometric objects may be used to determine how they should be linked (e.g., geometric objects with similar direction/orientation parameter values are more likely to be linked than geometric objects having disparate direction/orientation parameter values). As yet another example, each geometric object may be associated with one or more scale values (e.g., a Poker Chip™ may be associated with one or more values indicating the radius/diameter of the Poker Chip™), and the scale values of geometric objects may be used to determine how they should be linked (e.g., geometric objects of similar scale are more likely to be linked than geometric objects having disparate radii). As yet another example, each geometric object may be associated with one or more response values corresponding to the response of a scale detection filter used to determine the scale of the geometric object, and the response values of geometric values may be used to determine how the geometric objects should be linked (e.g., geometric objects having similar response values are more likely to be linked than geometric objects having disparate response values). It should be appreciated that geometric objects are not limited to having only the above-described parameter values and may be associated with one or more values of any other suitable parameters, as aspects of the technology provided herein are not limited in this respect.

In some embodiments, all of the parameter values associated with geometric objects may be used to determine how the geometric objects are to be linked. In other embodiments, only some of the parameter values (e.g., location parameter values only; direction/orientation parameter values only; scale parameter values only; response parameter values only; location and direction/orientation parameter values only; location and scale parameter values only; location and response parameter values only; direction/orientation and scale parameters; direction/orientation and response parameters only; scale and response parameters only; location, direction/orientation and scale parameter values only; location, direction/orientation, and response parameter values only; location, scale and response parameter values only, direction/orientation, scale, and response parameter values only) may be used to determine how the geometric objects are to be linked, as aspects of the technology described herein are not limited in this respect.

Figure 21:
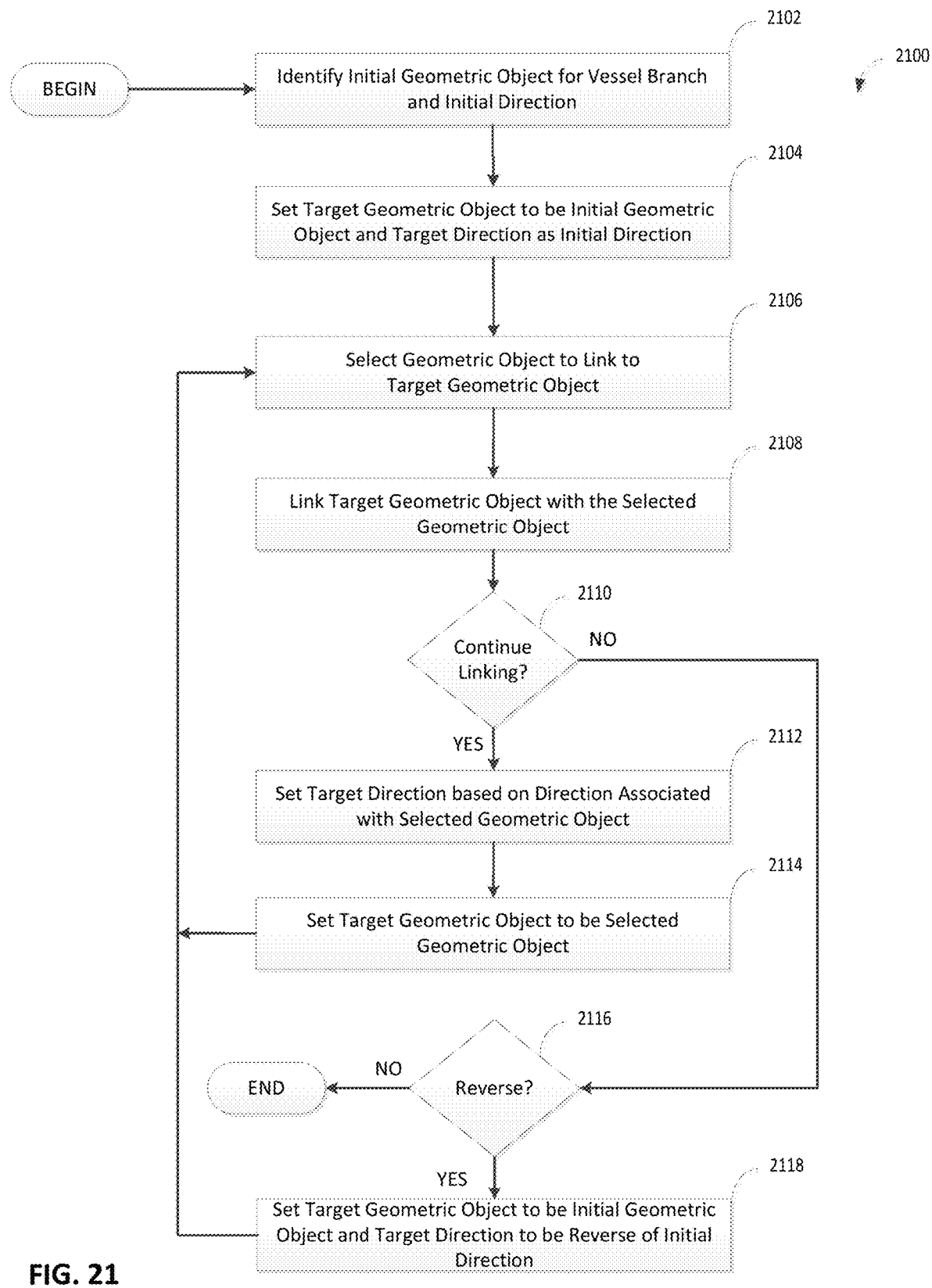
FIG. 21 is a flowchart of an illustrative process for linking geometric objects that represent cross-sections of a vessel in a vessel network, in accordance with some embodiments of the technology described herein.

FIG. 21 is a flowchart of illustrative process 2100 for linking geometric objects to generate a linked representation of a vessel segment. Process 2100 may be executed using any suitable system and, for example, may be executed using computer system 2800 described below with reference to FIG. 28. Process 2100 may be performed after a plurality of geometric objects (e.g., Poker Chips™) are obtained from one or more images using any of the techniques described herein.

Process 2100 begins at act 2102, where one of the plurality of geometric objects is identified as an initial geometric object to be used in generating a linked representation of a vessel segment. The initial geometric object may be identified from among the plurality of geometric object to be the most prominent geometric object. For example, the initial geometric object may be identified as the geometric object in the plurality of geometric objects having the largest scale (e.g., radius) and/or the largest response.

Though, the initial geometric object may be identified in any other suitable way, as aspects of the technology described herein are not limited in this respect. An initial direction in which to search for candidate geometric objects to link to the initial geometric object may be set equal to (or opposite to) the direction/orientation of the initial geometric object. The initial geometric object and the initial direction are then set as the target geometric object and the target direction, respectively, at act 2104 of process 2100.

Next, process 2100 proceeds to act 2106, where a geometric object to link to the target geometric object is selected from among multiple candidate geometric objects (e.g., at least two, at least five, at least ten, at least twenty five, at least one hundred, at least five hundred, at least one thousand, at least ten thousand candidate geometric objects). As discussed above, in some embodiments, the selection may be performed by comparing parameter values of the target geometric object with parameter values of the candidate geometric objects. Any of the above-described parameter values or any suitable combination of them may be used to perform the comparison. For example, in some embodiments, the selection may be performed at least in part by comparing at least one value for location of the target geometric object to respective values for location of the candidate geometric objects, and comparing at least one value for direction/orientation of the target geometric object to respective values for direction/orientation of the candidate geometric objects. Additionally or alternatively, the selection may be performed by comparing at least one value for scale of the target geometric object to respective values for scale of the candidate geometric objects. Additionally or alternatively, the selection may be performed by comparing at least one value for response of a scale detection filter (e.g., the scale detection filter used to detect scale of centerline voxels in any of the ways described herein) of the target geometric object to respective values for response of the scale detection filter of the candidate geometric objects.

In some embodiments, comparing parameter values of the target geometric object with respective parameter values of a candidate geometric object is performed by using a statistical model that provides, based on parameter values of the target and candidate geometric objects, a likelihood that the candidate geometric object and the target geometric object each represent cross sections of the same vessel segment. The statistical model may provide a likelihood that the candidate geometric object follows the target geometric object as a representation of another cross section of the same vessel segment. The statistical model may be used to obtain a likelihood that the target and candidate geometric objects each represent cross sections of the same vessel based on some (e.g., all) parameter vales of the target and candidate geometric objects. As one non-limiting example, the statistical model may provide the likelihood based at least in part, on at least one location value and at least one direction/orientation value of the target geometric object and at least one location value and at least one direction/orientation value of the candidate geometric object. As another non-limiting example, the statistical model may provide the likelihood based, at least in part, on at least one location value, at least one direction/orientation value, at least one scale value and at least one response value for each of the target and candidate geometric objects.

In some embodiments, the statistical model may be used to calculate a likelihood likelihood that the candidate geometric object follows the target geometric object by calculating a likelihood/probability of parameters of the candidate geometric object conditioned on parameters of the target geometric object. This may be done in any suitable way, one non-limiting example of which is described in more detail below.

In one non-limiting embodiment the statistical model may comprise a probability distribution representing the probability that target geometric object x (which is associated with location parameter value(s) $l_x$, direction/orientation parameter value(s) $v_x$, scale parameter value(s) $s_x$, and response parameter value(s) $r_x$) and candidate geometric object y (which is associated with location parameter value(s) $l_y$, direction/orientation parameter value(s) $v_y$, scale parameter value(s) $s_y$, and response parameter value(s) $r_y$) represent cross sections of the same vessel segment. It should be appreciated that direction/orientation $v_x$ is the direction of the target geometric object set at one of acts 2104, 2114, or 2216. We denote this distribution as:

$$\Pr(L_y = x | l_x, v_x, s_x, r_x). \tag{33}$$

This expression may be viewed as a posterior probability distribution with respect to the candidate geometric object. That is, when the target geometric object x is fixed, the posterior probability distribution will evaluate to a different value for every candidate target geometric object under consideration. Accordingly, in some embodiments, selecting a candidate geometric object to link to the target geometric object x may be performed by evaluating the probability distribution of Eqn. 33 for each of two or more candidate objects (holding the target candidate object fixed) and then selecting the candidate geometric object having the highest probability (according to Eq. 33) among those candidate geometric objects evaluated.

Absent assumptions on the prior distribution(s) of the variables $l_x$, $v_x$, $s_x$, and $r_x$, maximizing the probability distribution of Eqn. 33 is equivalent to maximizing the likelihood $$\Pr(l_x, v_x, s_x, r_x | L_y = x) \tag{34}$$

Under certain independence assumptions, the likelihood function of Eqn. 34 may be factored into a product of lower-dimensional distributions according to:

$$Pr(l_x, v_x, s_x, r_x | L_y = x) = Pr(dist(x, y), \overrightarrow{xy}, s_x, s_y, r_x, r_y | L_y = x) = \tag{35}$$
$$Pr(dist(x, y) | l_x) Pr(\overrightarrow{xy} | v_x) Pr(r_y, s_y | r_x, s_x),$$

where the probability distribution $Pr(dist(x, y)|l_x)$ represents the probability that candidate geometric object y and target geometric x represent cross sections of the same vessel segment based on location parameter values of the target and candidate geometric objects, where the probability distribution $Pr(\overrightarrow{xy}|v_x)$ represents the probability that candidate geometric object y and target geometric x represent cross sections of the same vessel segment based on direction/orientation parameter values of the target and candidate geometric objects, and where the probability distribution $Pr(r_y, s_y|r_x, s_x)$ represents the probability that candidate geometric object y and target geometric x represent cross sections of the same vessel segment based on scale and response parameter values of the target and candidate geometric objects. These probability distributions may be thought of as providing distance, direction/orientation, and scale/response based tests, respectively, in the order that they appear in Eqn. 35.

In some embodiments, the probability distribution $Pr(dist(x, y)|l_x)$ may be a Gaussian distribution, as shown below, so that the probability that target geometric object x and candidate geometric object y represent cross sections of the same vessel segment decreases exponentially with as the distance between the target and candidate geometric objects increases. That is, the probability distribution $Pr(dist(x, y)|l_x)$ may be:

$$Pr\left(dist(x, y) | l_x\right) = \frac{1}{\sqrt{2\pi}} \exp\left(-\frac{(|l_x - l_y| - \mu)^2}{2\sigma_d^2}\right). \tag{36}$$

The probability distribution of Eqn. 36 is a Gaussian probability distribution having mean $\mu$ (e.g., 1) and standard deviation $\sigma_d$ (e.g., 0.3). Though, it should be appreciated that $Pr(dist(x, y)|l_x)$ may take on any other suitable form and is not limited to being a Gaussian distribution.

In some embodiments, the probability distribution $Pr(\overrightarrow{xy}|v_x)$ may follow a super-Gaussian distribution, which has a "flat" top and exponentially decreasing tails, so that the probability that target geometric object x and candidate geometric object y represent cross sections of the same vessel segment decreases exponentially with increased disparity of orientation between the target and candidate geometric objects, but is not sensitive (or at least less sensitive than a Gaussian distribution) to local variations in the direction/orientation of centerline voxels (which may occur, for example, due to digitization errors). That is, the probability distribution $Pr(\overrightarrow{xy}|v_x)$ may be:

$$Pr(\overrightarrow{xy} | v_x) = \frac{1}{Z} \exp\left(-\frac{\theta(\overrightarrow{xy}, v_x)^4}{\sigma_\theta^4}\right) \tag{37}$$

Though, it should be appreciated that $Pr(\overrightarrow{xy}|v_x)$ may take on any other suitable form and is not limited to being a super-Gaussian distribution.

As discussed above, the scale and response parameter values may be also used to test the viability of linking candidate geometric object y with target geometric object x. Assuming that the scale and response values of geometric objects representing nearby cross sections of the same vessel segment change smoothly, linking two geometric objects having disparate scale and response parameter values should be assigned a lower probability. For example, in some embodiments, the probability distribution $Pr(r_y, s_y|r_x, s_x)$ may be:

$$Pr(r_y, s_y | r_x, s_x) = \frac{1}{Z} \exp\left(-\frac{(s_y - s_x)^2}{2\sigma_s^2(s)}\right) \exp\left(-\frac{\left(\frac{r_y}{s_y^3} - \frac{r_x}{s_x^3}\right)^2}{2\sigma_r^2}\right) \tag{38}$$

where Z is the normalization factor and the variance $\sigma_s(s)$ is equal set, for example, according to $\max\{0.5, 0.2s_x\}$. Though, it should be appreciated that $Pr(r_y, s_x|r_x, s_x)$ may take on any other suitable form and is not limited to having the density function of Eqn. 38.

Returning to the description of process 2100, after a candidate geometric object is selected for linking to the target geometric object, process 2100 proceeds to act 2108 where the selected geometric object is linked with the target geometric object. The target and selected geometric objects may be linked in any suitable way. For example, in some embodiments, the selected geometric object may be linked with the target geometric object by storing information identifying the selected geometric object in a list (or any other suitable data structure) together with information identifying the target geometric object. Additionally, in some embodiments, any geometric objects between the selected geometric object and the target geometric object may be linked to the target geometric object. For example, in some embodiments, any geometric object (e.g., Poker Chip™) in a cylinder defined by the target and selected geometric objects may be linked to the target geometric object. Any of the geometric objects linked to the target geometric object may be marked so that when the linking process continues, the geometric objects already linked and part of a linked representation of the vessel segment are not considered again.

It should be appreciated that after the target and selected geometric objects (and optionally one or more other geometric objects between the target and selected geometric objects) are linked at act 2108, the linked geometric objects form a linked representation of a vessel segment. In some embodiments, a linked representation of the vessel segment may be saved for later processing (e.g., by pushing information identifying the linked representation into a processing queue). Next, process 2100 proceeds to decision block 2110, where it is determined whether to continue the linking process by using the selected geometric object as the target geometric object to further update the linked representation of the vessel segment to include one or more additional geometric objects. This decision may be made in any suitable way, as aspects of the technology described herein are not limited in this respect. As one example, when the likelihood value associated with the candidate geometric object (e.g., computed using Eqn. 33) selected at act 2106 is below a threshold (e.g., signifying that none of the candidate geometric objects under consideration are sufficiently likely to represent a cross section of the vessel segment), it may be determined to not continue the linking process by using the selected geometric object as the target geometric object. On the other hand, when the likelihood value associated with the candidate geometric object selected at act 2106 is above a threshold, it may be determined to continue the linking process by using the selected geometric object as the target geometric object.

When it is determined at decision block 2110 that the linking process is to continue by using the selected geometric object as the target geometric object, process 2100 proceeds along the "YES" branch to act 2112, where the target direction is set to be a direction determined based on the direction/orientation of the target geometric object and the geometric object selected at act 2106. For example, the target direction may be set to the vector defined by the location values of the target and selected geometric objects. For instance, when the target and selected geometric objects are Poker Chips™ having center locations $l_x$ and $l_y$, respectively, the target direction may be set to be the vector $v_{target}=l_y-l_x$. Note that each of $l_x$ and $l_y$ may be a vector indicating the center locations in two or three dimensions. Next, process 2100 proceeds to act 2114, where the target geometric object is set to be the geometric object selected at act 2106. Next process 2100 returns to act 2106 and acts 2106-2108 and decision block 2110 are repeated. In this way the linking process may continue so that the representation of a vessel segment generated by using process 2100 may further be updated.

On the other hand, when it is determined at decision block 2110 that the linking process is to not continue by using the selected geometric object as the target geometric object, process 2100 proceeds to decision block 2116 where it is determined whether the linking process is to be performed again starting from the initial geometric object identified at act 2102 but in the opposite direction from the initial direction identified at act 2102. The determination to perform the linking process in the "reverse" direction may be made when the linking process was not previously run starting with the initial geometric object and an initial direction that is the opposite direction of the direction/orientation of the initial geometric object.

When it is determined that the linking process is to be continued from the initial geometric object in the opposite direction from the direction selected at act 2102, process 2100 proceeds to act 2116 where the target geometric object is set to be the initial geometric object and the target direction is set to be the opposite direction of the direction/orientation of the initial geometric object identified at act 2102. Process 2100 then returns to act 2106. On the other hand, when it is determined that the linking process is to not be continued from the initial geometric object in the opposite direction, process 2100 completes.

The linked representation of a vessel segment obtained by linking geometry using process 2100 may be used to compute further geometric features of the vessel segment. For example, the direction/orientation parameters of geometric objects in the linked representation capture information about the geometry of the vessel segment centerline. In some embodiments, integrating the direction/orientation vectors, a representation of the centerline curve may be obtained. That is, because the displacement/orientation vectors may represent tangents to the centerline curve at each location of a geometric objects in the linked representation, the centerline curve may be recovered from linked tangents by integrating over some desired segment of geometric objects.

Figure 13:
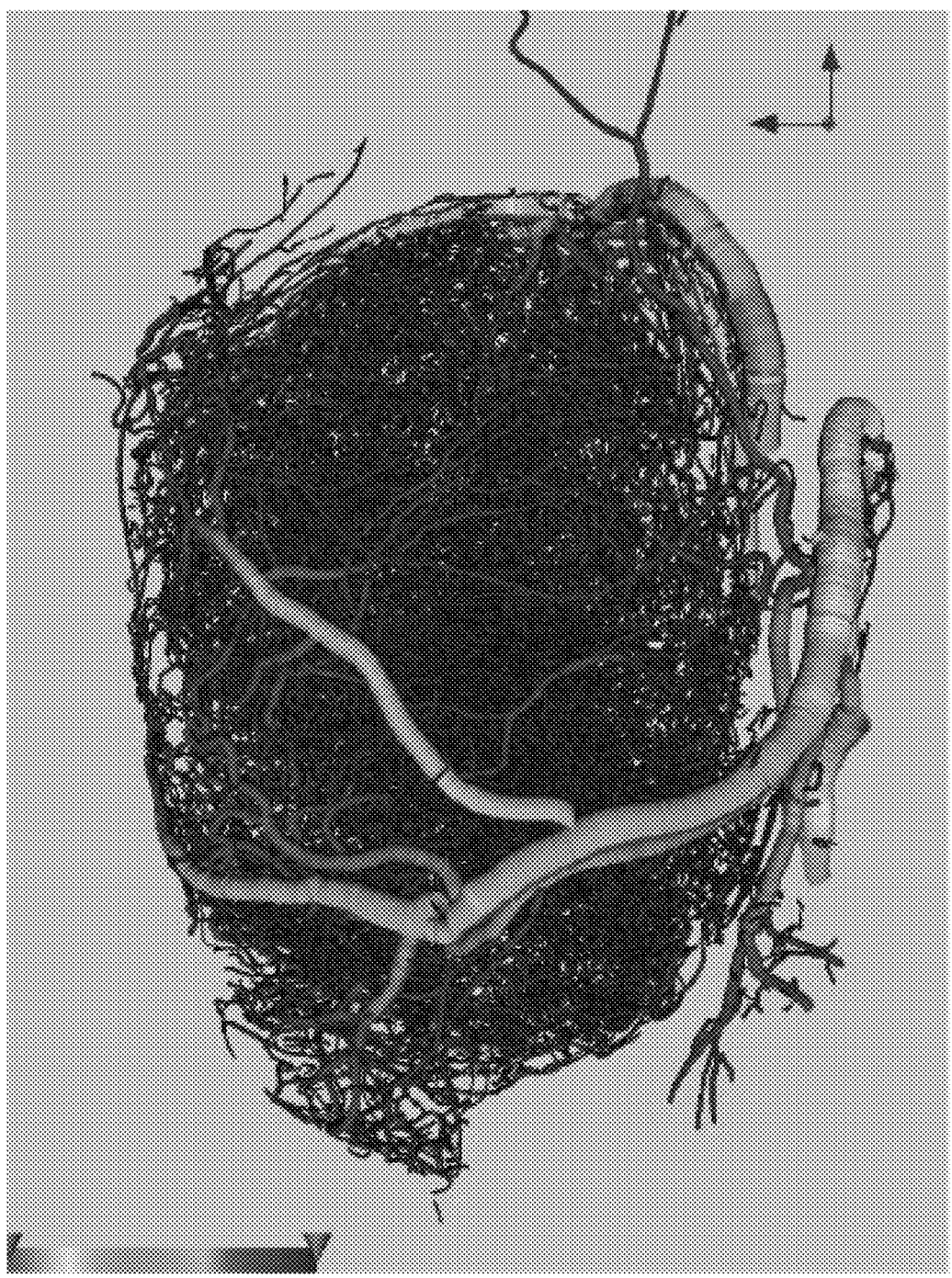
FIG. 13 illustrates a geometrical representation of vasculature obtained from a 3D volumetric image, in accordance with some embodiments of the technology described herein.

In addition, the linked representation may be used to determine higher-order and/or more sophisticated geometrical properties of the vessel segment. For example, derivatives of the linked orientation vectors may be used to determine the curvature of the vessel. The centerline curve, length of the curve and curvature parameters may be used to determine various tortuosity parameters, which may be used to characterize the vessels. Moreover, the linked representation of the vessel segment carries distribution information with respective to the density of vessel material, the relative distribution of vessels at different radii, etc. These geometrical, structural and distribution parameters may be used in a number of ways to analyze vasculature, as discussed in further detail below. FIG. 13 illustrates a geometrical representation of vasculature using the linked Poker Chip™ representation, wherein the geometry was extracted from a 3D volumetric image using the methods described herein.

Orientation Determination

As discussed above, linking of centerline voxels (e.g., center locations of a Poker Chip™) may be performed according to criteria that include minimizing the disparity of orientations of linked centerline voxels. For example, linking of centerline voxels may be achieved using probability models that provide for a measure of disparity of direction/orientation between a target Poker Chip and one or more candidate Poker Chips™. The inventors have realized that conventional methods for computing direction/orientation associated with a Poker Chip™ (i.e., instantaneous vessel direction at the Poker Chip™) may be unstable and may be unsuitable (or at least inconsistently applicable) for performing orientation tests for the purposes of linking (e.g., performed in accordance with process 2100 described above with reference to FIG. 21).

Conventional methods of determining orientation are frequently based on gradient information extracted from the underlying intensity image. However, computing direction or orientation from intensity information of an intensity image (e.g., a greyscale image) may be unstable and/or inaccurate, particularly in regions of high curvature and/or high frequency information. Moreover, direction/orientation computations based on operating on intensity information are vulnerable to noise. The inventors have developed a technique for determining direction at a Poker Chip™ from voxel locations, rather than gradient information extracted by operating on intensity data (e.g., greyscale images).

According to some embodiments, the direction v of a Poker Chip™ may be computed based on voxel locations in a segmented image, which herein refers to an image whose voxels are labeled as corresponding to subject matter of interest or not corresponding to subject matter of interest (e.g., using zero and non-zero values, respectively). For example, in images of blood vessels, voxels in a segmented image may be labeled as corresponding to a vessel or not corresponding to a vessel. One representation of a segmented image is a binary image where voxels within a vessel boundary are labeled as 1 (or a non-zero value, such as a value related to distance from a vessel boundary, as discussed below) and voxels not within a vessel boundary are labeled as 0 (or vice versa). When geometry has been extracted from images (e.g., Poker Chips™ have been obtained from image information), the locations of the voxels within the cross-section corresponding to the Poker Chip™ are known. This location information may be used to determine direction/orientation at a Poker Chip™ that may be more reliable than direction/orientation values computed by operating directly on intensity values in the image(s) (e.g., on the greyscale values of the image).

According to some embodiments, displacement vectors are computed from locations associated with a Poker Chip™ by finding the difference in location between voxel locations associated with a Poker Chip™ and locations in a neighborhood associated with the Poker Chip™. The neighborhood may be defined in any suitable way, some examples of which are described in further detail below. The displacement vectors may be utilized to compute the direction/orientation of the Poker Chip™, for example by performing principal component analysis (PCA) on the displacement vectors. However, the displacement vectors may be utilized in other ways to compute the direction/orientation at the Poker Chip™. Likewise, the location of voxels within a Poker Chip™ and a neighborhood of a Poker Chip™ may be used in other ways to determine direction/orientation at the Poker Chip™. Since the direction/orientation is computed using location information in a segmented image(s) and not from intensity information, the direction/orientation computations may be more accurate and/or stable (e.g., may be more robust in regions of high curvature, high frequency, noise and/or other image artifacts).

Figure 27:
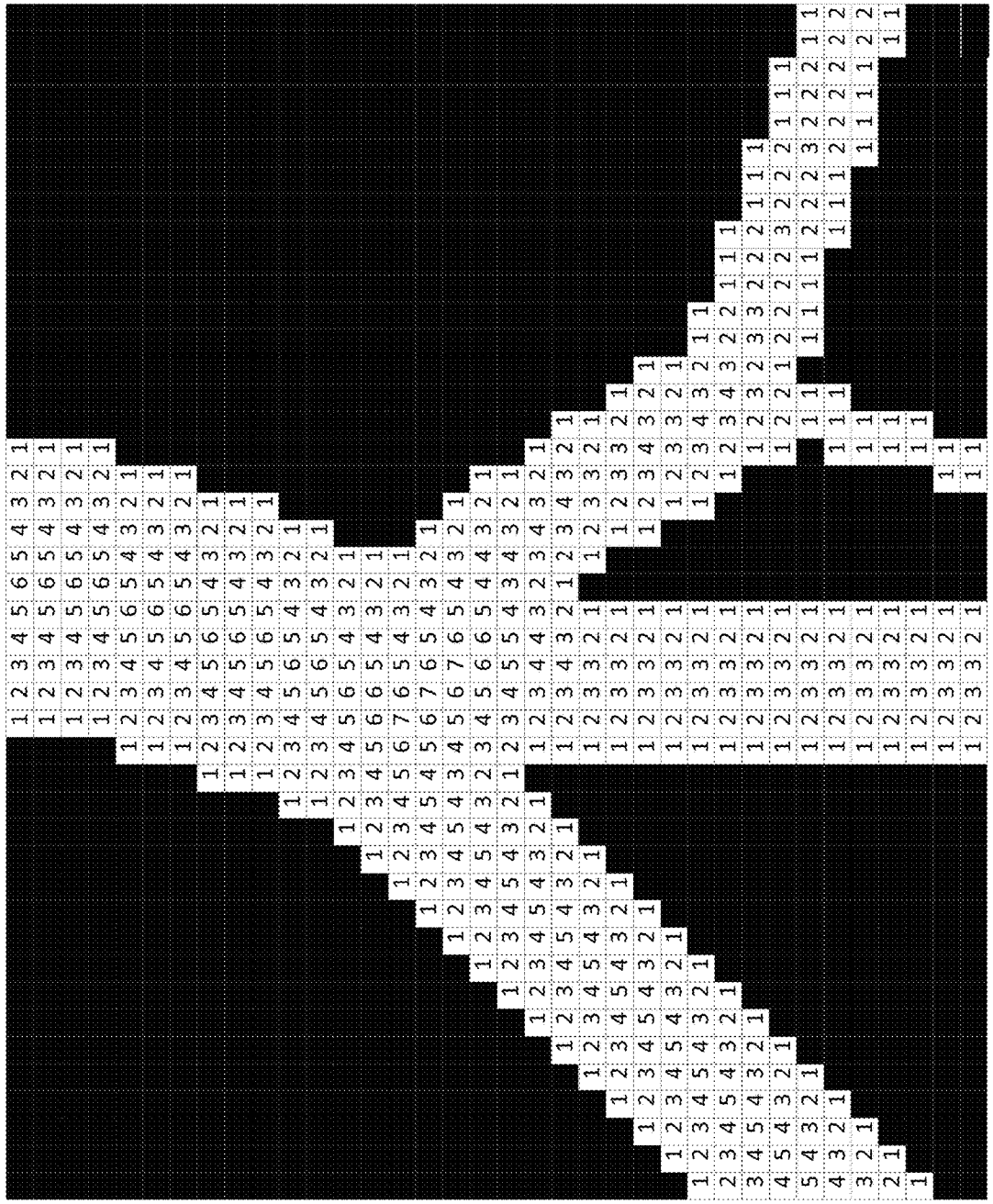
FIG. 27 illustrates a two-dimensional scale image, in accordance with some embodiments of the technology described herein.

The inventors have appreciated that direction/orientation computations may be made more reliable by operating on a scale image of the vessel structure. A scale image refers herein to a segmented image where voxel locations are labeled with a zero outside the boundary of a vessel (e.g., as determined from segmentation and/or by extracting vessel geometry from the image) and are labeled with non-zero values within the vessel boundary indicating the distance the voxel is from the vessel boundary. For example, a scale image may be a segmented image for which a distance transform has been computed such that voxels within a vessel boundary are labeled with their corresponding distance from the corresponding vessel boundary. FIG. 27 shows an illustrative two-dimensional scale image. It should be appreciated that although the scale image of FIG. 27 is two-dimensional, this is for clarity of presentation, as scale images may be, and likely are, three-dimensional images.

In the scale image of FIG. 27, voxels outside the vessel boundary are shown in black (e.g., are labeled as zero) and voxels inside the vessel boundary are labeled with the distance the voxel is from the vessel boundary. The distance or scale information may be utilized to define the neighborhood discussed above and/or may be utilized in evaluating the direction/orientation at a candidate Poker Chip™. According to some embodiments, displacement vectors are computed at a candidate location $x_0$, which may be the location of a candidate Poker Chip™ being assessed for a possible link to a target Poker Chip™. One exemplary formulation is provided below.

According to some embodiments, to determine the direction/orientation v at a voxel $x_0$ (e.g., a center voxel of Poker Chip™) a neighborhood of voxels $N(x_0)$ around voxel $x_0$ is computed according to:

$$N(I_0) = \{x \mid \text{distance}(x, x_0) \leq \lceil \text{scale}(x)+2 \rceil\} \quad (39)$$

As such, a neighborhood of voxels around $x_0$ may be defined based on the distance of the voxels from $x_0$ and the scale of voxels that are candidates for inclusion in the neighborhood $N(x_0)$. However, it should be appreciated that a neighborhood of voxels around voxel $x_0$ may be defined in any other suitable manner, as direction detection techniques are not limited for use with any particular neighborhood or neighborhood calculation. From the neighborhood $N(x_0)$ computed for voxel $x_0$, a scatter matrix $M(x_0)$ may be computed as follows:

$$M(x_0) = \frac{\sum_{i=1}^{\|N(x_0)\|} (v_i - \bar{v})(v_i - \bar{v})^T}{\|N(x_0)\|} \quad (40)$$

where $v_i = x - x_i$ for some $x_i$ in $N(x_0)$, $\bar{v}$ is the average of the vectors $v_i$, and $\|N(x_0)\|$ is the number of points in the neighborhood $N(x_0)$. The direction/orientation v may be associated with the eigenvector associated with the largest eigenvalue of the scatter matrix M. For example, the direction/orientation v may be the direction of the eigenvector associated with the largest eigenvalue (or the opposite direction). When $x_0$ corresponds to a center voxel of (or another voxel representing) a Poker Chip™, the direction orientation v obtained in accordance with the above-described embodiments may be used as the direction/orientation of the Poker Chip™. As a result, a direction/orientation v at each candidate location $x_0$ may be computed to facilitate linking together of Poker Chips™.

Branch Point Detection and Linking

As discussed above, generating a comprehensive linked vessel structure may involve detecting where vessel segments branch into further vessel segments and determining how vessel segments are linked together. The inventors have appreciated that branch point detection and linking may be achieved using a coarse-to-fine approach, however, other approaches may be utilized as well. According to some embodiments, a coarse-to-fine approach includes detecting branch point candidates from a set of locations (e.g., from a set of vessel locations including detected Poker Chips™), refining the set of branch point candidates based on local behavior and/or linking branches according to the junction type exhibited (e.g., the shape/topology of the branch relative to the linked vessel structure from which it branches). It should be appreciated that the techniques described herein, though applicable to 2D datasets, are particularly designed for processing 3D datasets (e.g., 3D geometry extracted from 3D x-ray scans). Conventional linking techniques (e.g., those implemented to link roads from a satellite image) are generally not suitable for accurately linking vessel structures and are not applicable to 3D datasets.

Figure 22:
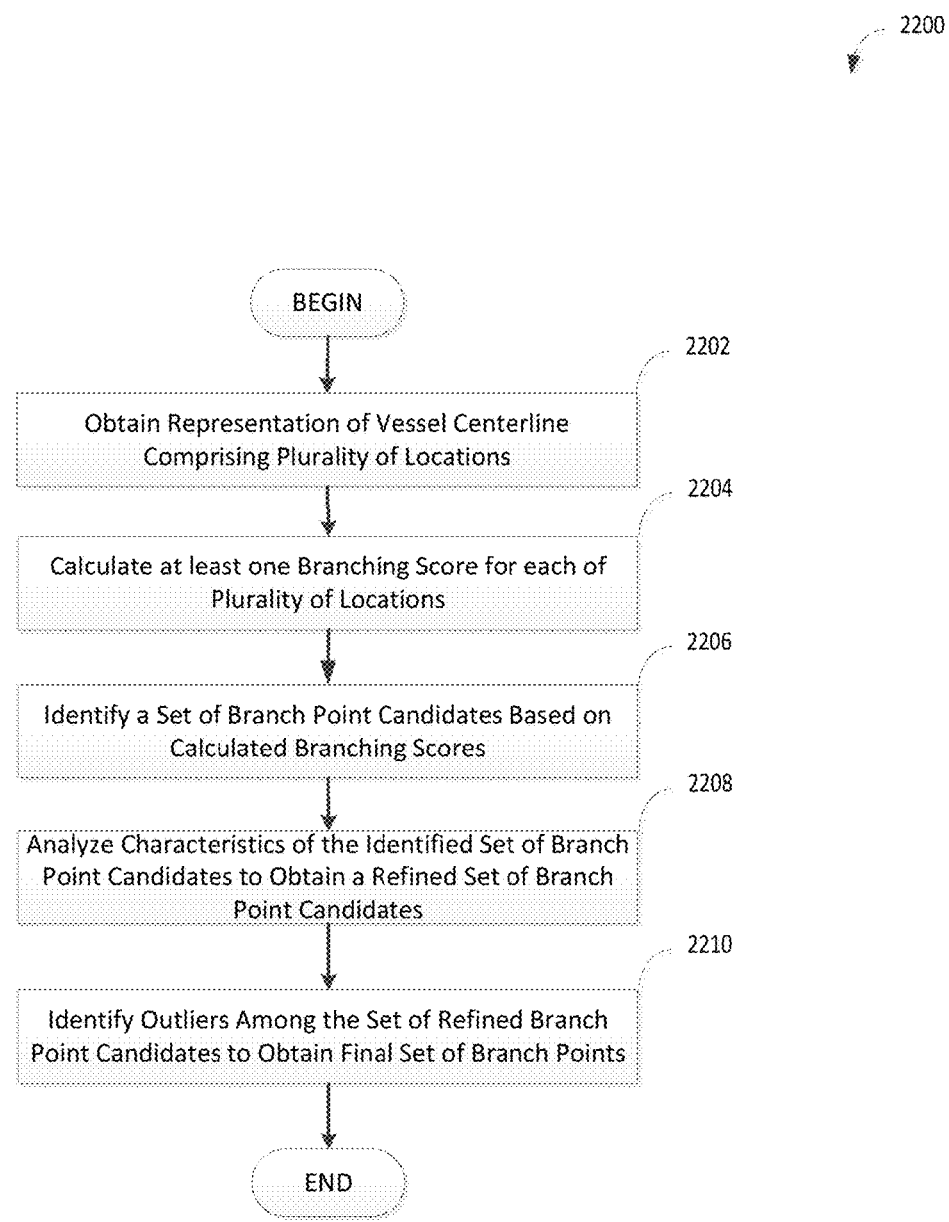
FIG. 22 is a flowchart of an illustrative process for detecting branching point locations, in accordance with some embodiments of the technology described herein.

FIG. 22 illustrates a method of identifying branch points, in accordance with some embodiments. In act 2202, a representation of a centerline for a vessel segment is obtained, the representation including a plurality of locations (e.g., locations of geometric objects extracted from a 3D x-ray scan of vasculature) corresponding to the vessel segment. For example, the representation of a centerline for a vessel segment may include a plurality of Poker Chips™ linked together using any of the techniques described herein, wherein the plurality of locations correspond to the center locations of the respective Poker Chips™. It should be appreciated, however, that the representation of a vessel centerline that includes a plurality of locations may be obtained in other ways, as techniques for identifying branch locations are not limited for use in connection with any particular representation or method of obtaining the representation. The linked segment for which branch points are being identified is also referred to below as the main segment, main branch or centerline as needed to clarify from branch segments or simple curves that may be generated during the course of identifying branch point for the main linked segment.

In act 2204, at least one branching score (also referred to as branch score) is calculated for each of the plurality of locations of the representation of the vessel segment. A branching score may be computed in any suitable manner and may depend on the representation of the vessel segment. According to some embodiments, the branch score is based, at least in part, on a measure of asymmetry (e.g., a measure of asymmetric variation in the distribution of geometric objects (e.g., Poker Chips™) associated with the representation at each respective location. According to some embodiments, the branching score is based on the probability model used to link centerline locations (e.g., Poker Chips™) as discussed in the foregoing. For example, the likelihood score from the probability model may be utilized not only to link centerline locations but to evaluate the likelihood that locations correspond to a branch point at which a further vessel segment branches from the representation of the target vessel segment (main segment) being evaluated. According to some embodiments, multiple techniques may be utilized to provide a branching score (e.g., asymmetry and linking likelihood measures may be used in combination to calculate a branching score or multiple branching scores). Any suitable technique may be used that provides at least one branching score indicative of how likely it is that the associated location corresponds to a branch point or branch location.

In act 2206, a set of branch point candidates are identified based, at least in part, on the branching scores computed in act 2204. For example, branching scores may be evaluated and high scoring locations (e.g., via thresholding or by taking the N largest branch scores) may be identified as branch point candidates. According to some embodiments, local maxima of the computed branching scores are identified to select the set of branch point candidates. For example, the branching scores computed for the plurality of locations may be viewed as a function from which branch point candidates may be selected by identifying local maxima (e.g., peaks) in the function. In embodiments in which multiple branching scores are computed for each location, the branching scores may be combined (e.g., via a weighted sum, average and/or weighted average) to form a single branching score for each location from which branch point candidates may be selected (e.g., using thresholding, N-greatest scores, local maxima techniques, etc.). Alternatively, multiple branching scores at each location may be analyzed in other ways, such as using a rule-based approach that considers the values of each branching point at a location and determines whether the location should be identified as a branch point candidate, using fuzzy logic, or any other suitable technique for evaluating multiple branch scores so as to determine whether a location should be considered (at least preliminarily) as a branch point candidate.

According to some embodiments, acts 2204 and 2206 may reflect a coarse process to identify a set of branch point candidates, which set may be further refined using further processes (e.g., by performing one or more of acts 2208 and 2210 described in further detail below) to eliminate one or more of the branch point candidates that do not meet further (and perhaps stricter) criteria. According to some embodiments, the set of branch point candidates computed, for example, in the manner described in connection with act 2204 and 2206 may be used as representing the final set of branch points, as further refinement may not be necessary in certain situations or environments. However, in some circumstances, it may be desirable to refine or filter the branch point candidates to remove from further consideration branch point candidates that do not exhibit one or more further characteristics of a branch point and/or to correctly characterize the branch segments with respect to the branch segments relationship with the centerline, some examples of which are described in further detail below.

In act 2208, one or more characteristics of the identified branch point candidates may be analyzed to refine the set of branch points to include only those branch point candidates that meet further criteria. According to some embodiments, the behavior of surrounding locations (e.g., surrounding Poker Chips™) may be evaluated to assess whether the branch point candidate is more likely to represent a true branch point, a non-branch point, or a nearby branch point. For example, each branch point candidate may undergo further processing by locally linking unlinked geometric objects in the vicinity of the branch point candidate (e.g., using any of the techniques described above in connection with FIG. 21) to evaluate whether the locally linked vessel segment (e.g., simple curve) interacts with the main linked vessel segment (centerline) from which it has been identified as a branch candidate in a manner suggestive of a branch (e.g., whether the linked branch segment, or a projected trajectory of the linked branch segment, intersects with the existing linked vessel segment) and/or how the locally linked vessel segment(s) (e.g., minor branch(es)) interact with the main vessel segment (e.g., major branch). Other characteristics of identified branch point candidates may be additionally or alternatively considered (e.g., location, orientation and/or scale of proximate geometric objects may be evaluated for continuity with an existing linked vessel segment) to refine the set of branch point candidates, as the act of refining is not limited to consideration of any particular characteristic or set of characteristics associated with the branch point candidates.

Refinement of the branch point candidates may include determining a type of junction for the branch point. For example, vessel structures may branch in a number of ways, each exhibiting a different behavior at the junction (branch point). Identifying the junction type may be performed to facilitate correctly linking vessel segments at their respective branch points. In this manner, branch point detection may be performed using coarse processing followed by a refining process to implement a coarse-to-fine approach, some examples of which are described in further detail below.

In act 2210, the refined set of branch point candidates may be further processed to remove outliers, though act 2210 may not need to be performed. In particular, the identified branch points and accompanying branch segments (e.g., simple curves) may be further analyzed to remove outliers from consideration as valid branch points or to identify an actual branch point when two or more branch points correspond to a same simple curve. For example, simple curves identified as branching from a branch point on a target centerline may be removed as potential branches when it is determined that insufficient non-zero scale voxels exist between the first geometric object in the simple curve and the branch point to support the hypothesis that the simple curve is a branch of the target centerline. This situation of insufficient support is indicative of the simple curve belonging to a distinct vessel segment other than the target linked segment (current centerline).

According to some embodiments, identified branch points are further evaluated to assess whether branch points that are close together are true branch points or whether they correspond to a single branch points. For example, adjacent branch points along a centerline that meet a proximity requirement are further evaluated to identify the true branch point. In other embodiments, multiple simple curves that have been associated with a single branch point are evaluated to assess the true branching structure at the branch point. Any of various methods may be utilized to identify outliers, filter identified branch points or otherwise rectify the branch points and associated minor branches to accurately reflect the true branching structure. Method 2200 in FIG. 22 described above may be repeated on any number of linked vessel segments so as to obtain a comprehensively linked structure of geometric objects (e.g., Poker Chips™) extracted from, e.g., a 3D x-ray scan of vasculature and/or otherwise obtained.

Figure 23:
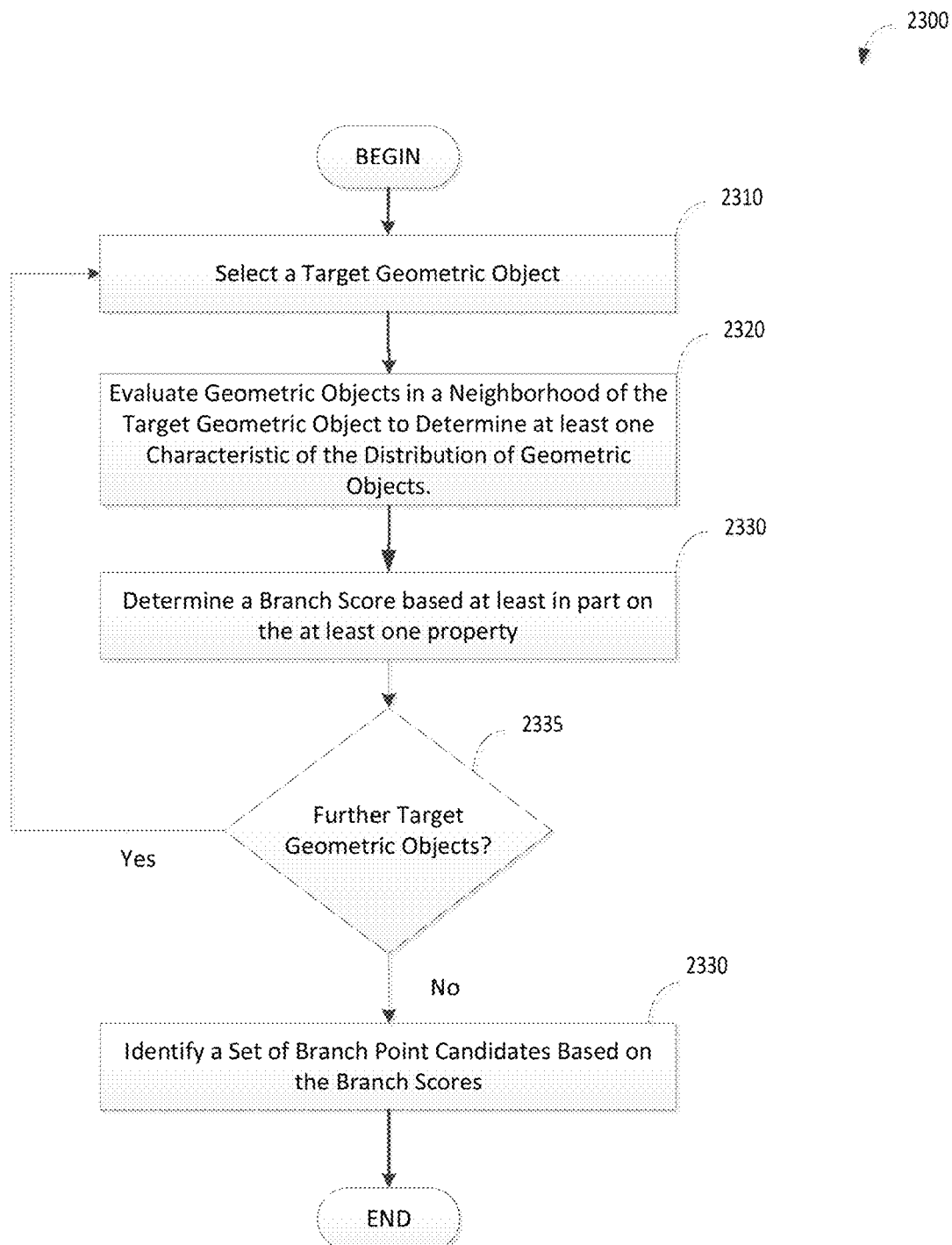
FIG. 23 is a flowchart of an illustrative process for calculating branching scores for locations on a centerline of a vessel, in accordance with some embodiments of the technology described herein.

As discussed above, identifying branch points may include a coarse-to-fine approach wherein a coarse process is performed to identify branch point candidates and a refining process is performed to identify branch points based on the branch point candidates. As also discussed above, the coarse process may include identifying branch point candidates using a branch point scoring process. According to some embodiments, the branch point scoring process is based on the inventors' recognition that the distribution of geometric objects (e.g., Poker Chips™) at branch locations will generally exhibit different characteristics than geometric objects (e.g., Poker Chips™) along a vessel segment at non-branch locations. Differences in Poker Chips™ distribution may be captured in a number of different ways including examining how Poker Chips™ are distributed about a target Poker Chip™ along a centerline of a vessel segment. FIG. 23 illustrates a method of identifying branch point candidates, in accordance with some embodiments.

Method 2300 may be performed, for example, on a set of geometric objects (e.g., Poker Chips™) extracted from a 3D x-ray dataset of a vasculature network, or may be performed on geometric objects obtained from other datasets.

In act 2310, a target geometric object is selected for analysis. The target geometric object may be one of the centerline locations of a linked vessel segment, linked in accordance with any of the techniques described herein. For example, each centerline location in a linked vessel (e.g., represented by a linked segment of Poker Chips™) may be evaluated for possible branching at that location and the selected target geometric object may be a first geometric object in the linked segment to be evaluated. The evaluation may then be performed iteratively on each geometric object in the linked segment or on a desired number of geometric objects in the linked segment (main segment or centerline).

Figure 24C:
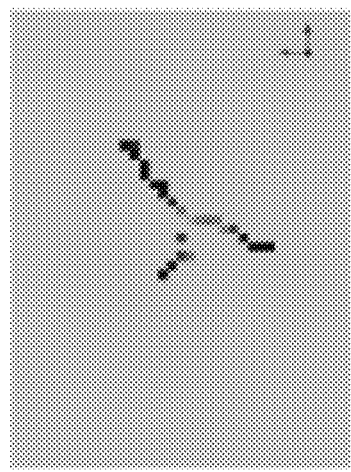
FIGS. 24A, 24B, and 24C illustrate calculation of a branching score, in accordance with some embodiments of the technology described herein.
Figure 24B:
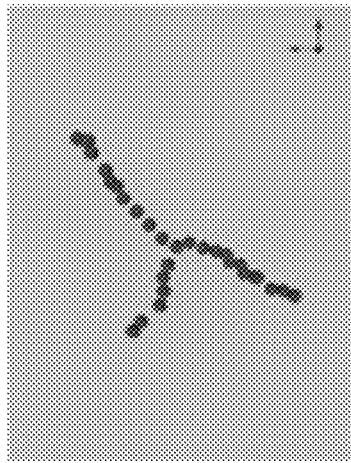
Figure 24A:
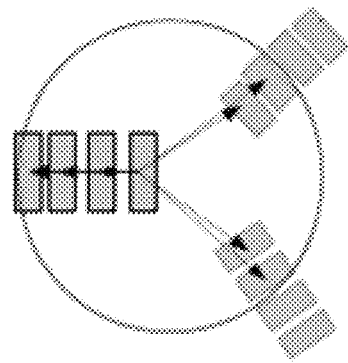

In act 2320, the distribution of geometric objects in a neighborhood of the target geometric is evaluated to determine at least one characteristic of the distribution. As discussed above, the inventors have recognized that geometric objects are distributed differently at branch locations than at non-branch locations. Based on this insight, the inventors have developed techniques to determine one or more characteristics of the neighborhood distribution of geometric objects to score the location associated with the target geometric object according to how strongly the neighborhood distribution is suggestive of a branch point. FIG. 24A illustrates schematically the evaluation of geometric objects in a neighborhood of a target geometric object.

The neighborhood can be chosen to be of any size, but typically is chosen to be large enough so as to accurately capture the local distribution of geometric objects. According to some embodiments, the neighborhood is selected to be of a fixed size about the target geometric object (e.g., all geometric objects within a circle centered on the target geometric object and having a fixed radius). According to some embodiments, the neighborhood is selected to be of size that depends, at least in part, on one or more of the parameters that describe the geometric object. For example, when the geometric object corresponds to a Poker Chip™, the neighborhood size may be selected based at least in part on the scale (e.g., radius) of the Poker Chip™. However, the size of the neighborhood may be selected in any manner suitable for a given application.

According to some embodiments, displacement vectors between the target geometric object and geometric objects in a predetermined neighborhood of the target are evaluated to determine one or more characteristics of the distribution. A displacement vector refers herein to any vector that provides information regarding a spatial relationship between locations. As such, in the context of geometric objects, a displacement vector may be any vector construct that provides information regarding the spatial relationship between geometric objects. For example, a displacement vector may capture the spatial relationship between two Poker Chips™ (e.g., the spatial relationship between the center locations of two Poker Chips™). The inventors have appreciated that displacement vectors between a target geometric object and geometric objects in a neighborhood of the target provides a mechanism for capturing the manner in which the geometric objects are distributed about the target geometric object, and may be used as a basis for computing one or more characteristics of the local distribution of geometric objects.

Typically, the displacement vectors will more generally align in the direction of the centerline (main segment) of a linked structure at non-branching points and will have more variability in this respect at branch points. Accordingly, this property may be exploited to score the location associated with the target geometric object based on the variability (also referred to herein as asymmetry) in connection with the distribution of geometric objects in the neighborhood. According to some embodiments, the variation in the principal directions of the displacement vectors is computed to obtain a measure of the variability or asymmetry of the neighborhood about the target geometric object. Any technique may be used to evaluate the variability of a neighborhood of geometric objects, some examples of which are discussed in further detail below.

In act 2330, the location corresponding to the target geometric object is scored relative to how indicative the at least one property of the target neighborhood is of a branch point. According to some embodiments, the variability (or asymmetry) of the neighborhood of geometric objects about and in relation to the target geometric object, however computed, is used to score the location associated with the target geometric object. The score may then be utilized to identify a set of branch point candidates, as discussed in further detail below.

In act 2335, it is determined whether there are further target geometric objects to be evaluated. For example, it may be determined whether each geometric object that forms a linked segment has been considered in connection with branch scoring (e.g., whether there are further Poker Chips™ along a linked vessel segment for which branch scoring has not been performed). If there are further geometric objects to consider, a next target geometric object is selected for scoring (act 2310) and a neighborhood of the new target geometric object is evaluated (act 2320) and a location associated with the new target geometric object is branch scored (act 2330). If all of the desired geometric objects (e.g., all Poker Chips™ along a linked segment) have been branched scored, the resulting branch scores may be further evaluated to identify a set of branch point candidates. FIG. 24B illustrates a number of geometric objects and FIG. 24C illustrates the geometric objects shaded in relationship to their respective branch scores using some embodiments of branch scoring.

In act 2340, the branch scores computed by iteratively repeating acts 2310-2330 (e.g., branch scoring each Poker Chip™ along a linked vessel segment) may be evaluated to locate branch point candidates. For example, all locations having a branch score that meets certain criteria may be selected as branch point candidates. The criteria selected may be any criteria that suitably identifies locations that are indicative of branch points. According to some embodiments, the branch scores are thresholded and all locations that meet the threshold criteria (e.g., that exceed a given threshold) are selected as branch point candidates. According to some embodiments, the branch scores are viewed as a function and local maximum (or local minimum) are identified and selected as branch point candidates (e.g., peak picking may be performed on the computed branch scores). However, any technique that suitably identifies branch point candidates from the scored locations may be used, as identifying branch point candidates from a plurality of branch scores is not limited to any particular technique(s) for doing so.

As discussed above, the inventors have appreciated that candidates for possible branch points (i.e., points in a vessel structure where a vessel branches into two or more vessels, including splits, tributaries, multiple splits, etc.) may be determined in a number of ways. According to some embodiments, branch point candidates are identified at locations where the linking analysis described above does not result in any high enough probability link to another Poker Chip™ (e.g., according to some threshold of likelihood). As such, branch point candidates may include the termination points of linked segments.

The inventors have also appreciated that branch points may also exhibit different variation and/or asymmetry properties than non-branch locations (e.g., with respect to the distribution of geometric object about such points). In view of this insight, the inventors have developed techniques to evaluate variation patterns at locations along a linked segment to facilitate identifying branch point candidates. As also discussed above, the inventors have recognized that the distribution of geometric objects differs at branch locations than at non-branch locations (or may exhibit other asymmetry characteristics that are detectable). For example, the principal directions of variation for displacement vectors computed in connection with a neighborhood of a target geometric object may be computed to assess how the geometric objects in the neighborhood are distributed. According to some embodiments, the principal directions of variation for displacement vectors computed between a target geometric object and each geometric object in a neighborhood of the target geometric object is computed and analyzed to assess whether the target geometric object corresponds to a possible branch point or branch location. Following below are non-limiting examples of analyzing a neighborhood of geometric objects about a target location to assess whether the distribution of the geometric objects indicates the presence of a branch point. According to some embodiments, principal component analysis may be performed on displacement vectors in a neighborhood of a target geometric object being considered to evaluate geometric object distribution and/or structure about the target geometric object, for example, by identifying asymmetry based on the relationship of the principal components (e.g., based on principal directions of variation as assessed by comparing eigenvectors and/or eigenvalues of a matrix formed from a neighborhood of the target geometric object). According to some embodiments a segmented image and/or a scale image may be used to define a neighborhood and/or compute displacement vectors from which the principal directions of variation may be determined. The principal directions of variation may be evaluated (e.g., using eigenvector analysis) to assess whether the target geometric object corresponds to a possible branch point location.

According to some embodiments, detection of branch point candidates may proceed by defining a neighborhood of a target voxel $x_0$ associated with a geometric object (e.g., centered on a Poker Chip™) as follows:

$$N(x_0) = \{x | \sigma(x_0) < \text{dist}(x, x_0) \leq D \land \text{connect}(x, x_0)\} \quad (41)$$

Where the distance D may be expressed as follows:

$$D = \begin{cases} 2\sigma(x_0) + 4 & \sigma(x_0) < 4 \\ \sigma(x_0) + 8 & \sigma(x_0) \geq 4 \end{cases} \quad (42)$$

That is, the neighborhood of a target voxel $x_0$ centered on a Poker Chip™ may be defined by non-zero scale voxels having a distance from target voxel $x_0$ between $\sigma(x_0)$ and D. It should be appreciated that a neighborhood of a target voxel may be computed in any way and the above formulation is merely one example of defining a neighborhood N. Typically, voxels in the neighborhood of the target voxel (i.e., the location associated with the target geometric object)

that are considered in the following computations are those that are also associated with the location of a geometric object (e.g., voxels that represent the center location of a Poker Chip™). For each x in the neighborhood N (however computed) a displacement vector may be computed as follows:

$$v = \frac{x - x_0}{|x - x_0|} \tag{43}$$

As discussed above, to assess characteristics of the geometric objects in a neighborhood, displacement vectors may be computed only for voxels associated with a geometric object. However, in other embodiments, displacement vectors may be computed for each voxel in the neighborhood or for some other desired subset of voxels in the neighborhood. The displacement vectors may be used to form a matrix suitable for performing principal component analysis. According to some embodiments, the matrix may be formulated as follows:

$$M(x_0) = \frac{\sum_{i \in N(x_0)} vv^T}{\|N(x_0)\|} \tag{44}$$

Where $\|N(x_0)\|$ is the number of voxels inside the neighborhood for which a displacement vector is computed. It should be appreciated that the above matrix is one example of a matrix that may be suitable for providing a basis for performing principal component analysis to evaluate characteristics of neighborhood N. When M is computed as a real symmetric matrix as it is in the above formulation (48), the matrix can be diagonalized as:

$$M = U \begin{pmatrix} \lambda_1 & & \\ & \lambda_2 & \\ & & \lambda_3 \end{pmatrix} U^T \tag{45}$$

The eigenvalues λ and/or the relationship between the eigenvalues may be analyzed to assess one or more properties regarding the principal directions of variation of the displacement vectors, e.g., to assess whether the vessel structure at the target location is symmetric with respect to its cross-section (likely no branch point) or asymmetric in this respect (branch point candidate). For example, when $x_0$ is not on or not close to a branch point, $\lambda_2$ and $\lambda_3$ will likely be small (e.g., close to zero). When $x_0$ is near or at a branch point, $\lambda_2$ will likely be relatively large. As such, $\lambda_2$ may operate as an indicator as to the likelihood of the existence of a branch point at location $x_0$. According to some embodiments, the principal components are computed for visited Poker Chips™ such that the values $\lambda_2$ form a function. The peaks of this function may be selected as branch point candidates for further evaluation (e.g., fed into a branch point model to assess whether the locations correspond to branch points and/or to assess what type of branch point the candidate represents, as discussed in further detail below. A sliding window may be utilized to evaluate branch scores (e.g., branch scores based, at least in part, on $\lambda_2$) determined for each desired target voxel $x_0$ (e.g., visited Poker Chips™) and the local maximums in the resulting branch score function (e.g., asymmetry function) selected as branch point candidates. It should be appreciated that the above described technique for evaluating the variation with respect to the distribution of geometric objects (e.g., the principal directions of variation of displacement vectors) in a neighborhood of a target geometric object is a non-limiting example and other ways of evaluating characteristics of the distribution of geometric object may also be performed to facilitate identification of branch point candidates.

Figure 25:
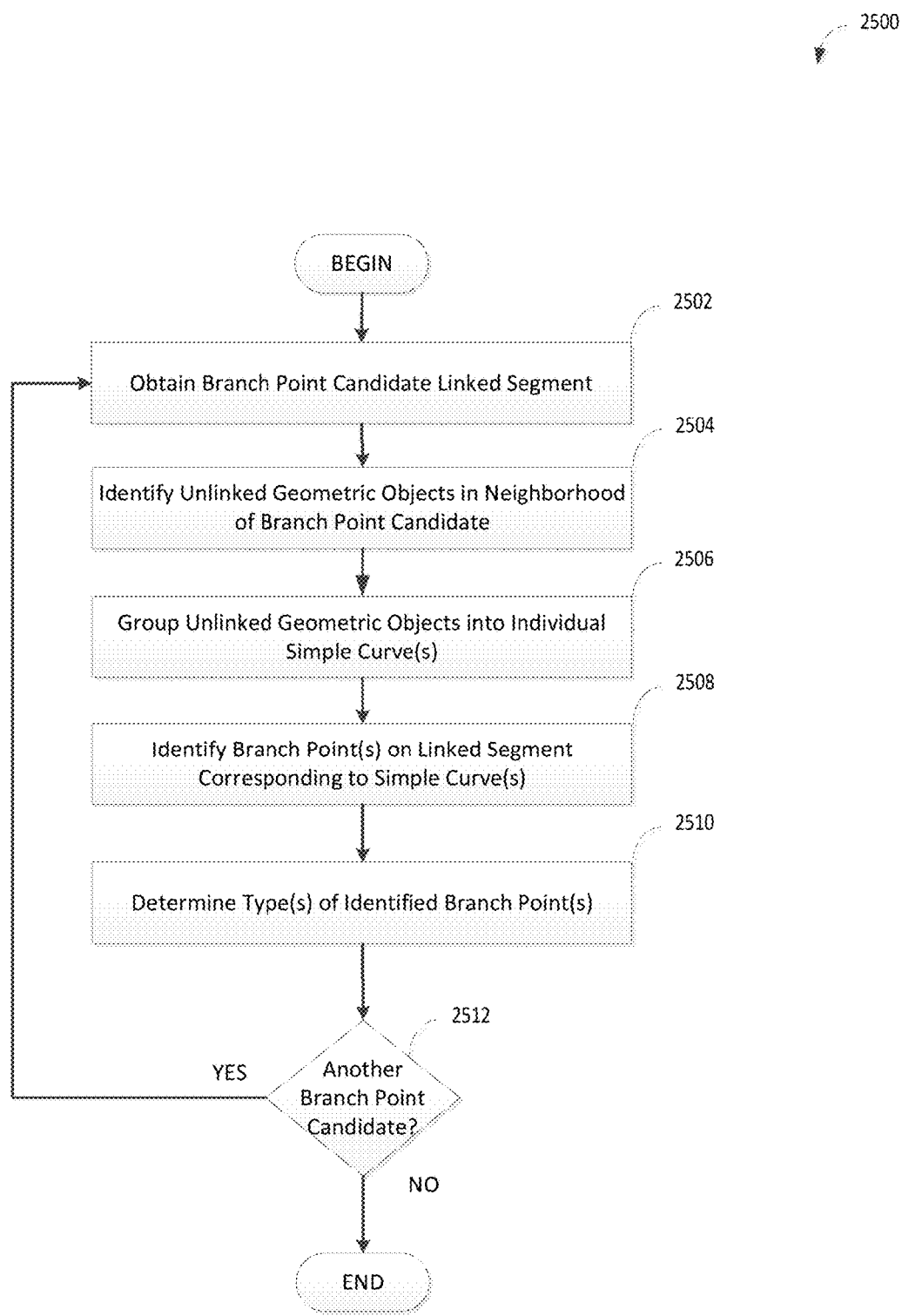
FIG. 25 is a flowchart of an illustrative process for analyzing characteristics of branch point candidates, in accordance with embodiments of the technology described herein.

As discussed in the foregoing, identifying branch point candidates (e.g., as described in connection with FIG. 23 above) may represent a coarse process that identifies branch point candidates for further consideration, or may represent a final set of branch points without undergoing further refinement. According to some embodiments, the set of branch point candidates identified via branch scoring undergo further refinement to evaluate whether the branch candidate is a branch point and how an accompanying minor branch interacts with the presently linked vessel at the branch point. FIG. 25 illustrates a method 2500 of refining a set of branch point candidates and identifying relationships between branch junctions and a linked segment, in accordance with some embodiments. According to some embodiments, a branch model is utilized to identify different junction types, as also discussed in further detail below.

In act 2502, a branch point candidate is selected for evaluation. For example, the branch point candidate may be selected from a set of branch point candidates identified according to any of the techniques described herein (e.g., the branch point identification method described in connection with FIG. 23). In act 2504, unlinked geometric objects in a neighborhood of the branch point candidate are identified. The neighborhood may be the same or different than the neighborhood selected for branch scoring and identification of branch point candidates. In act 2506, the identified unlinked geometric objects in the neighborhood are group into simple curves. The term "simple curve" refers herein to locally linking geometric objects in the neighborhood. For example, any of the techniques described herein for linking geometric objects (e.g., linking Poker Chips™) may be applied to form relatively short segments from the unlinked geometric objects in the neighborhood.

According to some embodiments, the unlinked geometric object in the neighborhood that is closest to the branch point candidate is selected to begin local linking, after which the next closest unlinked geometric object may be selected for local linking and so on until all of the unlinked geometric objects in the neighborhood have been locally linked. According to some embodiments, the unlinked geometric object with the largest radius (or closest radius to the geometric object at the branch point candidate), the highest confidence, or any other criteria may be selected to perform local linking and repeated until each unlinked geometric object in the neighborhood has been processed to form one or more linked segments (simple curves). Linking of each individual simple curve from a starting point (e.g., the closest unlinked geometric object from the linked vessel segment (centerline) may be terminated using any type of criteria. For example, local linking of a simple curve may be stopped when the linking probability falls below a certain threshold, using a distance threshold (e.g., distance from the centerline), using a maximum length criteria for the simple curve, using a maximum number of geometric objects criteria, etc. The simple curves (however computed and in whatever order linked) may then be assessed to evaluate their interaction with the linked vessel segment to assist in identifying the branch points and/or the type of branch corresponding to the simple curve.

In act 2508, the geometric object in each simple curve closest to a geometric object in the linked vessel segment is identified. That is, for each simple curve generated in act 2506, the pair of geometric objects on the simple curve and the linked vessel segment having a minimum distance are identified. This information may be utilized to identify the actual branch points and also to characterize the type of junction formed (e.g., using a junction-type or branch model). In particular, the geometric object of a linked structure closest to a geometric structure on a simple curve may be identified as a branch point. The geometric object identified as a branch point may correspond to a branch point candidate or may correspond to another geometric object on the linked segment that was not identified as a branch point candidate. With the branch points on the linked segment identified, the branch or junction-types may be identified to correctly link together the larger vessel structure. According to some embodiments, the simple curves (e.g., relatively short locally linked segments (minor branch), grown from unlinked geometric objects in the neighborhood of a branch point candidate) may be projected or extended along its trajectory to determine whether the simple curve intersects with the linked vessel structure to assess whether the simple curve is a branch of the linked vessel structure.

According to some embodiments, determining whether and where a simple curve branches from a linked vessel segment or centerline of a major branch proceeds by considering a ray R, for example, between the closest points. Given a simple curve or line segment of a possible minor branch (a set of points $x_i$, $i=1, \ldots, n$) and a location on a linked vessel segement (centerline) $x_0$ (e.g., a location assocaited with a geometric object on a linked vessel segement/major branch), the best ray fitted to points set $\{x_i\}$ and passing $x_0$ is obtained by solving the minimization problem.

$$\operatorname{argmin}\Sigma dist(x_i, R(x_0, v)) = \operatorname*{argmin}_{v} \sum \{(x_i - x_0)^2 - [(x_i - x_0) \cdot v]^2\}$$
$$= \operatorname*{argmax}_{v} \sum [(x_i - x_0) \cdot v]^2$$
$$= \operatorname*{argmax}_{v} \left( v^T \underbrace{\left[\sum (x_i - x_0)(x_i - x_0)^T\right]}_{M} v \right)$$

The solution to above minimization is the eigenvector associated with the largest eigenvalue. A measure of the likelihood that the simple curve (minor branch) actually joins (i.e., branches from) the linked vessel segment may be defined as follows.

$$\frac{1}{\sqrt{2\pi}} \exp\left(\frac{\Sigma_i d_i^2}{2}\right)$$

where $d_i$ is the residual error of each point on the possible branch segment to the best fitted ray R. Accordingly, each geometric object location on the centerline L, may be evaluated to find the location with the smallest fitting error $$e = \sqrt{\frac{d_i^2}{N-1}}.$$

If all of the fitting errors $$e > \frac{\sqrt{2}}{2},$$

there is no branching point. Otherwise, the a set of points, S, on the centerline L which have the fitting error falling in the range [e,e+0.1] are identified (e.g., all geometric objects on the linked vessel structure that have an error below a threshold are identified as possible branch points). When multiple possible branch points are identified, further processing may be performed to identify one or more actual branch points and/or to characterize the type of junction at the identified branch point, as discussed in further detail below.

In act 2510, the type(s) of the identified branch points are determined. For example, the junction at which a vessel segment branches from another segment may take on a number of different configurations. FIGS. 26A-C illustrate examples of junction types of a branching vessel structure. FIG. 26A illustrates a Y-junction, FIG. 26B illustrates a V-junction and FIG. 26C illustrates a T-junction. The inventors have developed techniques for identifying these junction types based on characteristics of the identified branch points and the simple curves to facilitate accurately constructing a linked vessel structure. In some embodiments, a best matching vessel segment model may be fitted to the branch points in a neighborhood of an identified branch point.

According to some embodiments, a branch model or junction model is utilized to classify the branch type of each identified branch points, as discussed in further detail below. For example, given a neighborhood of a branch point candidate and a centerline L (e.g., a linked vessel segment), a local linking algorithm is applied to all unlinked geometric objects in a neighborhood to generate linked segments $\{c_i, i=1 \ldots n\}$ (e.g., acts 2502-2506 may be performed). For each segment $c_i$, the location of the geometric object in the centerline or major linked vessel segemtn (e.g., $x \in L$) that has the minimum distance to the curve $c_i$ is found (e.g., act 2508 may be performed). If x is in the middle of the linked vessel segment L, the junction between the linked vessel segement L and the simple curve $c_i$ is a Y-junction (e.g., as shown in FIG. 26A). If x is at the end of the linked vessel segment L, the junction between the linked vessel segment L and the simple curve $c_i$ is a V-junction (e.g., as shown in FIG. 26B). Otherwise, the junction between the linked vessel segement L and the simple curve $c_i$ is a T-junction (e.g., as shown in FIG. 26C).

The inventors have developed a branch point model to evaluate the above circumstances and also to handle certain special cases that may arise. For example, the following procedure may be utilized to identify junction types in a variety of circumstances. As discussed above, the pair of locations on the linked vessel segment (centerline) and a simple curve (possible minor branch) that have a minimum distance may be identified. The linked vessel structure and the simple curve are referred to in the following description as the centerline (or major segment) and the simple curve (or minor segment), and the two locations are referred to as the major closest point and the minor closes point, respectively. When the major and minor closest points are in the middle of the centerline and the simple curve, respectively, the simple curve centered on the minor closest point may be broken and only the part considered a straight line is taken for further evaluation. This straight line segment may be evaluated as a simple Y junction by the Y-junction model.

When the major closest point is at one end of the centerline, and the minor closest point is in the middle of the minor simple curve, the branch point may be labeled as a T-junction type branching point. When both major closest point and minor closest point are at one end of the centerline and minor simple curve, respectively, the branching point may be labeled as a T-junction type branch point. It should be appreciated that the circumstances that arise regarding the structure and configuration of branch points may be evaluated and resolved in other ways and the foregoing description merely describes some possible ways of doing so.

Various techniques described in the foregoing may be utilized to obtain a comprehensively linked structure, e.g., a fully linked vessel network for a 3D x-ray scan of vasculature. However, the techniques may also be used to linked together only portion of a vasculature, as the techniques described herein on not limited for use to any particular linking application or result.

Detection of Loop Structure

As discussed above, a linked representation of a vessel network may comprise a network structure graph representing connectivity among vessel segments in the vessel network. The inventors have recognized that loops in a vessel network may be difficult to detect and conventional linking methods were not equipped to detect or handle such loop structures in the vessel network. As a result, conventional methods of linking vessel structures are inaccurate in this respect.

Accordingly, in some embodiments, loops in a vessel network may be detected and taken into account when generating a linked representation of the vessel network. In this way, the vessel network structure graph may accurately represent loops in the vessel network (e.g., the vessel network structure graph may comprise one or more cycles) representing loops in the vessel network).

Loops in the vessel network may be detected in any of numerous ways. For example, according to some embodiments, loops may be detected in part by labeling geometric objects (e.g., Poker Chip™) as visited and/or linked such that when a geometric object that is already labeled as visited and/or linked is identified as a candidate geometric object to be linked to more than a single vessel segment (e.g., two or more different vessel segments), the geometric object may be evaluated from both directions (that is with respect to membership to each of two or more vessel segments) to assess whether the vessel structure forms a loop. When it is determined that a geometric object may be linked to two or more vessel segments (which may be done in any suitable way including, for example, the linking techniques described with reference to FIG. 21 above), the location of the geometric object (e.g., the center point of a Poker Chip™) may be identified as a branch point location. In such a case, the vessel network structure graph may be updated to include a vertex corresponding to the branch point and to include edges, incident to this vertex, that correspond to the two or more vessel segments to which the geometric object may be linked to.

Parallelization

According to some embodiments, the linking algorithm may be performed in parallel. Since linking is generally local and may not need to rely on the information from far away voxels, the algorithm can be parallelized by dividing the image into small blocks. Then individual CPUs may operate on a single block without the need to communicate with other blocks. Because of the computation requires some neighborhood information, each block may include a fixed margin overlapping with its neighbor's margin. The speed gained by parallelization is the number of processors divided by one plus overhead caused by margin. In one example, dividing a volume of 2000×2000×1400 into 500×500×500 blocks and using 8 processors produced a gain of 4.49 times processing speed.

The margin for parallelization may be chosen based on the following: 1) the margin for the scale selection $m_s = r_{max}+1$; 2) the margin for the smoothing $m_{sm} = 3\sigma$; 3) the margin for the gradient computation $mg=1$; 4) the margin for the direction detection $m_d = m_g + r_{max} + 1 + m_{sm}$; 5) the margin for centerline filtering $m_c = \max\{2r_{max}, m_d\}$; and 6) the margin for the non-maximum suppression $m_{sprs} = r_{max} + m_c$.

Because the block algorithm for parallelization needs to divide the volume into blocks at the beginning and assembling the blocks into a volume at the end, a way to transform between global coordinates and block coordinates may be needed. The block id $(b_x, b_y, b_z)$ for a point $(i, j, k)$ in the global coordinate is given as:

$$b_x = \left\lfloor \frac{i}{s} \right\rfloor \quad (46)$$

$$b_y = \left\lfloor \frac{j}{s} \right\rfloor$$

$$b_z = \left\lfloor \frac{k}{s} \right\rfloor$$

The local coordinates in its block is $(i', j', k')$ $$i' = i - b_x s$$

$$j' = j - b_y s$$

$$k' = k - b_z s \quad (47)$$

The dimension $(s_x, s_y, s_z)$ of the block $(b_x, b_y, b_z)$ is:

$$s_x(b_x) = \begin{cases} \mathrm{mod}(N_x, s) & \text{if } b_x = \left\lfloor \frac{N_x}{s} \right\rfloor - 1 \wedge \left\lfloor \frac{N_x}{s} \right\rfloor \neq 0 \\ 0 & \text{if } b_x < 0 \\ s & \text{otherwise} \end{cases} \quad (48)$$

$$s_y(b_y) = \begin{cases} \mathrm{mod}(N_y, s) & \text{if } b_y = \left\lfloor \frac{N_y}{s} \right\rfloor - 1 \wedge \left\lfloor \frac{N_y}{s} \right\rfloor \neq 0 \\ 0 & \text{if } b_y < 0 \\ s & \text{otherwise} \end{cases}$$

$$s_z(b_z) = \begin{cases} \mathrm{mod}(N_y, s) & \text{if } b_z = \left\lfloor \frac{N_z}{s} \right\rfloor - 1 \wedge \left\lfloor \frac{N_z}{s} \right\rfloor \neq 0 \\ 0 & \text{if } b_z < 0 \\ s & \text{otherwise} \end{cases}$$

Given a point $(i', j', k')$ at block $(b_x, b_y, b_z)$, the global offset in the file is:

$$pos = \underbrace{i's_y s_z + j's_z + k'}_{} + \underbrace{\left(\frac{b_z N_x N_y s_z(b_z-1) + b_y N_x s_y(b_y-1)s_z(b_z) +}{b_x s_x(b_x-1)s_y(b_y)s_z(b_z)}\right)}_{block\ offset} \quad (49)$$

The number of blocks in the x dimension is $$n_{bx} = \left\lceil \frac{N_x}{s} \right\rceil,$$

the number of blocks in the y dimension is $$n_{by} = \left\lceil \frac{N_y}{s} \right\rceil,$$

and the number of blocks in the z dimension is $$n_{bz} = \left\lceil \frac{N_z}{s} \right\rceil.$$

A one dimensional block ID $1=(1, \ldots, n_{bx} n_{by} n_{bz})$ to 3D index $$b_x = \left\lfloor \frac{l}{n_{by} n_{bz}} \right\rfloor$$

$$b_y = \left\lfloor \frac{l - b_x n_{by} n_{bxz}}{n_{bz}} \right\rfloor$$

$$b_z = l - b_y\ n_{bz} - b_x n_{by} n_{bz}$$

(50)

Three dimensional block ID ($b_x$, $b_y$, $b_z$) to one dimensional block ID. When connecting the linked structure from adjacent blocks, a glue layer between the different blocks may be analyzed and the how the linked structure in the adjacent blocks approach Poker Chips™ in the glue layer may be evaluated to determine how to link the local linked structures together. According to some embodiments, probability models (e.g., similar to the probability models discussed above) can be used to assess the likelihood that a Poker Chip™ in the glue layer is part of local linked structure in two or more adjacent blocks.

The inventors have appreciated that the speed of linking a geometric representation of a vessel structure may be accelerated by dividing the representation into smaller regions and processing them in parallel. The inventors have developed techniques for stitching the linked structures from the smaller regions together to form a larger linked structure representing the vessel network. Methods for stitching or gluing structures from adjacent regions together are described in further detail in Appendix A. According to some embodiments, location and direction of Poker Chips™ in a glue region at the juncture of adjacent regions are evaluated to determine how sub-structures should be stitched or glued together to form a larger linked structure.

Information relating to the geometry of a subject's vasculature, or a portion thereof, can be used to determine one or more qualitative and/or quantitative measures of geometrical, structural, and/or distribution parameters of the subject's vasculature that are informative for diagnostic, predictive, prognostic, therapeutic, interventional, research and/or development purposes, as well as for grading and/or staging a disease. It should be appreciated that vasculature geometry may be obtained for any suitable blood vessel volume, as the aspects of the technology described herein are not limited in this respect. In some embodiments, all the geometrical information captured by the linked Poker Chips within a target volume of interest may be evaluated. However, in some embodiments, useful information may be obtained from analyzing only a subset of Poker Chips within a target volume (e.g., about 10%, about 20%, about 30%, about 40%, about 50%, about 60%, about 70%, about 80%, or about 90%) as aspects of the technology described herein are not limited in this respect.

According to aspects of the technology described herein, the types of geometrical or structural information that may be extracted from images (e.g., extracted from a linked Poker Chip representation) includes a measure of vessel curvature, tortuosity, branching, diameter, etc., or any combination thereof. Optionally, or additionally, a measure of vessel density (and/or the density of vessels having one or more predetermined structural characteristics) may be determined and/or analyzed. It should be appreciated that a Poker Chip may consist of or include information relating to the size (radius), angle, etc. of the vessels being represented. In some embodiments, the Poker Chip representation may include linking information (e.g., relating to the linkage angle etc. between a first Poker Chip and one or more adjacent Poker Chips).

Tubular structures (e.g., blood vessels in a cast or in vivo) of different size ranges may be analyzed separately and compared to different threshold or reference values as described herein. In some embodiments, one or more structural parameters are obtained (e.g., calculated or modeled, etc.) for only a subset of size ranges (e.g., only for those size ranges for which changes are known to be associated with a diagnostic, prognostic, clinical, or research application of interest). However, in certain embodiments, all of the size ranges are analyzed. In some embodiments, one or more different parameters are analyzed for different size ranges. However, in certain embodiments, the same parameter(s) is/are analyzed for all of the size ranges that are being assayed. Analyses may be provided in the form of histograms or curves representing a distribution of numerical values or scores obtained for the different ranges.

It should be appreciated that analytical techniques used to categorize blood vessels based on size may be used to categorize other tubular body structures based on size. In some embodiments, once the tubular structures (e.g., blood vessels) are categorized based on size, the associated values or scores obtained for different parameters of interest can also be categorized and analyzed. Aspects of the technology described herein may be automated, for example, as described herein.

Aspects of the technology described herein relate to analyzing data obtained for body structures in animals (e.g., in test animals). In one embodiment, the technology described herein relates to obtaining pattern information relating to one or more aspects or regions of the vasculature of an animal. Pattern information obtained according to aspects of the technology described herein may be used to analyze a disease model (e.g., to assess whether an animal disease model is representative of an actual disease based on structural vascular features, or to assess the progression of one or more vascular changes in a test animal that provides a validated disease model, etc.), to evaluate the effectiveness of a treatment regimen, to identify candidate compounds or treatment regimens that are therapeutically effective, or for other applications where data relating to vascular structures (e.g., the progression of vascular structures, changes in vascular structure over time or in response to different drugs or drug dosages or administration frequencies, etc., or any combination thereof) is informative. For example, aspects of the technology described herein may be used to identify one or more pattern elements that can be used to help diagnose or evaluate diseases, including but not limited to cancer, retinopathies, and cardiac, renal, and/or haptic disease, provide prognostic information, monitor treatments, screen therapeutic agents, select one or more therapeutic agents (e.g., help determine or predict a subject's responsiveness to a particular drug), etc., or any combination thereof.

In some embodiments, structural vascular features, and/or changes in structural vascular features, can be used to evaluate the effectiveness and/or toxicity of one or more therapeutic compounds or treatment modalities. In some embodiments, the toxicity of a compound (e.g., a known therapeutic compound or a candidate therapeutic compound) can be evaluated by determining vascular changes in response to the compound. The vascular changes can be determined over the whole body, within a tissue, within an organ (e.g., the liver or kidneys), or within a portion of any one thereof. In some embodiments, a qualitative assessment of vascular change is made. In some embodiments, a quantitative assessment of vascular change is made. In some embodiments, vascular changes in a healthy body, tissue, or organ, is evaluated. In some embodiments, toxicity (e.g., drug toxicity) can be determined based on changes in vascular patterns (e.g., changes in vascular morphology or any other change in vascular features described herein). In some embodiments, a vascular therapeutic index can be calculated as a ratio between vascular changes in treated diseased regions versus vascular changes in normal, nontreated, tissues, organs or organ regions. In some embodiments, a ratio of vascular changes in a treated diseased region (e.g., a tumor) relative to vascular changes in a control (e.g., either a control that is not treated, or a control tissue that is not diseased but that is exposed to the treatment) can be calculated. In some embodiments, vascular changes in a non-diseased organ or tissue (e.g., non-diseased kidney or liver) of a subject that has a disease (e.g., cancer or a tumor) in a different tissue or organ can be assessed and compared to vascular changes in a healthy subject. It should be appreciated that one or more quantifications described herein (e.g., one or more ratios of vascular changes in treated versus control organs or tissue) can be used, either directly or indirectly, as a basis for providing a quantitative assessment of vascular toxicity of a particular compound or treatment.

Aspects of the technology described herein may be used to study, identify, and or analyze geometrical, structural, and/or distributional features of blood vessels that are associated with one or more diseases or conditions represented by an animal of interest. In some embodiments, an animal may be a disease model as described herein. In some embodiments, an animal may be undergoing a therapeutic regimen of interest. In some embodiments, an animal may be treated with a candidate therapeutic compound. Accordingly, aspects of the technology described herein may be used to identify, analyze, and/or evaluate one or more vascular patterns or changes in vascular patterns associated with a disease. Aspects of the technology described herein also may be used to evaluate the effects of one or more therapeutic regimens or candidate compounds. In some embodiments, therapeutic effectiveness may be evaluated using one or more vascular patterns or changes therein as a marker of a response (or lack thereof) to treatment. Accordingly, aspects of the technology described herein may be used to identify particular vascular patterns that are indicative of certain diseases or disease stages. These patterns can subsequently be used in sensitive assays to detect diseases in vivo (e.g., in human subjects). Other aspects of the technology described herein may be used to select therapeutic regimens or candidate compounds for administration to a patient (e.g., a human patient) in a therapeutically effective amount and in a physiologically acceptable form.

It should be appreciated that in some embodiments, an animal (e.g., an animal that is perfused with a casting agent composition) may be sacrificed prior to analysis regardless of whether the analysis is performed in situ or not. Accordingly, in some embodiments, changes over time may be studied using a plurality of animals and using one or more animals for each time point of interest. In some embodiments, different dosages, different therapeutic regimens, different drugs or drug combinations, or any combination of two or more thereof may be studied using different animals (with at least one animal for each condition of interest). It should be appreciated that combinations of time courses and drugs, drugs dosages, or other therapeutic regimens similarly may be studied using a plurality of different animals, each representing a unique condition. It should be appreciated that the different animals are preferably genetically identical or similar (e.g., identical for at least one trait that is associated with a disease or condition of interest). In some embodiments, the animals may be mice, rats, sheep, cats, dogs, primates, or any suitable non-human experimental animal.

In some embodiments, a combination of different drugs, different doses, etc., may be evaluated at a series of time points according to aspects of the technology described herein. Again, it should be appreciated that a different animal may represent a different drug, dosage, time point, or combination thereof, because each animal may be sacrificed for analysis. However, in some embodiments, a single animal may be tested at different sites (representing, e.g., different drugs, dosages, time points, etc.) depending on the impact of the casting agent that is used and the site of administration of the casting agent.

In some embodiments, samples from one or more animals may be prepared and analyzed periodically during the time course of a treatment (e.g., using a group of animals exposed to the same experimental conditions). In some embodiments, different conditions may be compared. For example, separate groups of animals (e.g., groups of mice) may be exposed to a candidate drug and a placebo (or other control). In some embodiments, subsets of animals (e.g., one or more animals) may be perfused with a casting agent composition at different time points and vascular structures may be imaged (e.g., directly or through reconstruction) for each time point. For example, tumors may be induced in genetically-altered mice using appropriate controls and different dose levels or regimens (e.g., 1, 2, 3, 4, 5, or more different dose levels or regimens) of one or more therapeutic compounds or compositions. Vascular structures then may be analyzed at different time points using methods of the technology described herein to evaluate the effectiveness of a drug composition and/or to identify biological markers that can be used to monitor a patient response to the drug composition. It should be appreciated that vascular structures of different sizes may be studied to identify structural features and/or distribution patterns of interest. In some embodiments, blood vessels having a diameter of about 50 microns are studied. However, it should be appreciated that smaller or larger vessels, or a combination thereof, may be studied.

In some embodiments, a vasculature characteristic may be evaluated over time by comparing results at different time points. However, it should be appreciated that the end-point of a study may be used as a single time point and characteristics associated with different diseases or treatments may be compared to identify or infer changes associated with a disease, treatment, or other condition of interest. Aspects of the technology described herein can be used to analyze data obtained from any suitable image source to identify one or more patterns associated with tubular structures of different sizes (e.g., structural patterns of blood micro-vessels). One or more parameters of a structural pattern can be used as biomarkers for different biological conditions and processes (including pathogenic conditions). Accordingly, aspects of the technology described herein relate to disease detection, diagnosis, grading, staging, disease monitoring, monitoring the effectiveness of therapy and interventional applications based on an analysis of structures (e.g., in situ structures) to identify patterns that may be associated or correlated with a disease or other physiological condition. According to aspects of the technology described herein, a pattern may comprise one or more different parameters. Parameters may be one or more structural features of individual tubular structures and/or one or more distribution properties (e.g., spatial distribution, spatial orientation, frequency, number, etc., or any combination thereof) of one or more tubular structures and/or one or more distribution properties (e.g., spatial distribution, spatial orientation, frequency, number, etc., or any combination thereof) of one or more individual tubular structural features within a subject or a within a region of interest in the subject, or any combination thereof. Accordingly, a vasculature pattern may include one or more structural features of an individual blood vessel (e.g., micro-vessels), a distribution of one or more blood vessels (e.g., micro-vessels) within a subject, a distribution of one or more individual blood vessel structural features (e.g., individual micro-vessel structural features), or any combination thereof. An individual blood vessel structural feature may include, but is not limited to, vessel tortuosity, curvature, branching (e.g., frequency, angle, hierarchy, etc.), diameter, direction, etc., or any change (e.g., variation or frequency) of any of these features over a predetermined length of the blood vessel being analyzed, or any combination thereof. A distribution of blood vessels or individual blood vessel structural features may include, but is not limited to, a blood vessel density, a distribution of blood vessel directions, a distribution of blood vessel diameters, a distribution of distances between blood vessels, a distribution of blood vessel spatial orientations (e.g., relative to each other), a distribution of blood vessel curvatures, a distribution of any other individual blood vessel structural features described herein, other distributions of blood vessel parameters or any combination of two or more thereof. It should be appreciated that the distribution of blood vessels or blood vessel structural features may be determined and/or analyzed for a predetermined region within a subject (e.g., a target volume of tissue within a subject) or within predetermined tissues or organs within a subject or throughout the subject (e.g., within a vascular cast). It also should be appreciated that either the absence or presence of blood vessels or of individual blood vessel structural features within a predetermined volume being analyzed may be a pattern parameter that can be used in analytical methods of the technology described herein. It also should be appreciated that one or more pattern parameters may be monitored and/or analyzed as a function of time. Accordingly, blood vessel patterns can be used as biomarkers for different biological conditions and processes (including pathogenic conditions). Accordingly, aspects of the technology described herein relate to identifying and evaluating biological markers that may be used for in vivo disease detection, diagnosis, grading, staging, for disease monitoring, for monitoring the effectiveness of therapy and interventional applications in live animals, including humans, based on an analysis of vasculature patterns including vasculature morphology and/or architecture in experimental subjects, for example experimental animals (e.g., animals perfused with one or more casting agent compositions). In one embodiment, the in vivo density, and/or diameter distribution, and/or geometric orientation of blood vessels (e.g., micro-vessels) may be analyzed, quantified, and/or evaluated for disease detection, monitoring, and/or interventional applications. In one embodiment, the sensitivity and specificity of disease diagnosis may be enhanced by analyzing and evaluating in vivo vasculature morphology and/or architecture associated with a tissue lesion. Accordingly, aspects of the technology described herein include detecting in vivo indicia of diseases associated with abnormal vascular structures or patterns. Other aspects include disease diagnosis, staging, grading, monitoring and prognosis, patient treatment, drug development and validation, and research applications. It should be appreciated that one or more biological markers identified in vascular casts in association with a response to a known drug or treatment may be used as a reference markers to evaluate the effectiveness of additional drugs or treatments in comparison to the known drug or treatment.

Certain embodiments according to aspects of the technology described herein includes a method of analyzing geometric features of blood vessels and correlating one or more features with a biological process, condition, or disease. Accordingly, certain geometric features of blood vessels may be used as biomarkers indicative of particular biological processes, conditions, and/or diseases.

In some embodiments, data for tubular structures (e.g., blood vessels) may been sorted into bins based on their size (e.g., their diameter). Aspects of the invention may increase the analytical resolution when evaluating structural information that is obtained for one or more experimental models and/or subjects being evaluated. According to aspects of the technology described herein, a binned structural analysis refers to any analysis of tubular structures that have been sorted or categorized according to size (e.g., according to the diameter or radius of the tubular structure in an area of interest). For example, in some embodiments a binned micro-vessel density (BMVD) analysis refers to an analysis of blood vessel density based on blood vessels that have been categorized according to vessel diameter in an area of interest.

Binned analytical techniques can be applied to the analysis of many different parameters that may be characteristic of tubular structures. Binned analytical techniques may be performed on tubular structures observed in casts or in vivo (e.g., in situ). For example, bins of tubular structures having different diameters can be evaluated to determine one or more of the following parameters: tortuosity, curvature, density, branching frequency, branching hierarchy (e.g., presence or absence of a branching hierarchy), relative distribution and/or direction of tubular structures (e.g., blood vessels), etc., or any combination thereof. By performing the analysis on binned data, small changes that primarily affect structures in one size range are more likely to be detected, because they are not masked by a relative absence of change in structures in other size ranges. Accordingly, methods of the technology described herein can be used to refine an analysis of tubular structures (e.g., blood vessels) over time or in response to disease or treatment, etc., where the analysis may be performed on casts and/or in vivo. Aspects of the technology described herein can also be used to detect or delineate diseased tissue (e.g., cancerous or pre-cancerous tissue, necrotic regions, etc.) in casts and/or in vivo.

It should be appreciated that, regardless of the source of information relating to vessel geometry, structure, and/or distribution (e.g., from analysis of BMVD, casts, in vivo, images, representations, etc., or any combination thereof), analytical methods described herein may be used. Accordingly, any analytical descriptions of vessel distributions that are provided in the context of one source of information may be applied to that analysis of vessel distributions obtained from one or more other sources as appropriate.

In some embodiments, spatiotemporal information about the vessel distribution provides numerous indicators about the health of a tumor, the effectiveness of a treatment such as the efficacy of a particular anti-angiogenic drug, and how a tumor is changing over time with respect to differently sized vessels. Numerous exemplary applications using one or more distribution analyses (e.g., based on BMVD measurements), in accordance with various aspects of the technology described herein. The inventors have identified and disclosed various applications that are facilitated by the acquisition of information about vessel characteristics, distribution, size, shape, etc., in PCT application US2005/047081 filed on Dec. 22, 2005, which is hereby incorporated by reference in its entirety. The inventors have appreciated that certain of these applications are facilitated by obtaining one or more BMVD measurements or by using one or more alternative binned analyses. It should be appreciated that any application may involve an analysis limited to one or more (e.g., 2, 3, 4, 5, 6, 7, 8, 9, 10, or more) bins of microvasculature of different sizes. For example, binned analyses may be useful for diagnostic applications. In one embodiment, aspects of the technology described herein can be used to detect and diagnose diseases associated with patterns (e.g., individual structural features or distributions) of in situ tubular networks. In some cases, a diagnosis can be rendered from an examination of the patterns (e.g., individual structural features or distributions) of interest at a single time. Alternatively, disease progression in a subject can be tracked by performing a structural analysis at two or more (e.g., 3, 4, 5, 6, 7, 8, 9, 10, or more) time points. Disease tracking can be used to provide diagnostic and prognostic information for a patient. For example, disease progression information can be used to assess the aggressiveness and/or invasiveness of a tumor.

The technology described herein can be used to screen an individual or a population for the presence of indicia relating to one or more diseases. As mentioned herein, the screen may be a whole body screen, or may be focused on one or more target regions (e.g., specific organs or tissues).

In one embodiment, the techniques described herein can be used automatically to identify individuals with one or more disease-associated structural patterns or features. These individuals can be subsequently tested for additional indicia of disease. The subsequent testing can take any suitable form, as the aspects of the technology described herein are not limited in this respect. For example, follow on testing can employ conventional techniques. As a non-limiting example, the use of aspects of the technology described herein may enable cost-effective screening techniques that may identify a relatively small pool of candidates as at risk of a disease, and may justify the use of relatively more expensive testing procedures to reach a final diagnosis or prognosis, wherein the follow on techniques may be too expensive to administer to a wider sample that has not been narrowed using the techniques of the technology described herein. As a further example, aspects of the technology described herein, either alone or in combination with other techniques, can be used to perform subsequent tests. In this respect, the sensitivity of the initial screening can be set relatively high, such that it may indicate some false positives, and subsequent application of techniques in accordance with aspects of the technology described herein can be employed with a higher degree of sensitivity that may provide more detailed information.

In one embodiment, aspects of the technology described herein can be used to screen a population of at risk individuals (e.g., individuals with genetic or other risk factors for a disease such as cancer, a circulatory disorder, or other disease) to identify the presence of disease indicia in one or more individuals.

In one embodiment, diagnostic methods of the technology described herein are computer-implemented to increase efficiency and throughput, and reduce variability associated with individual physicians. However, as discussed herein, in some embodiments, the final diagnosis may be made by a physician based on information generated by an automated analysis or a structural representation using aspects of the technology described herein.

As shall be appreciated from the foregoing, aspects of the technology described herein can be used on patients known to have a disease, or can be used to screen healthy subjects on a regular basis. A subject can be screened for one or more diseases. Screening can be done on a regular basis (e.g., weekly, monthly, annually, or other time interval); or as a one-time event. Different conditions can be screened for at different time intervals and in function of different risk factors (e.g., age, weight, gender, history of smoking, family history, genetic risks, exposure to toxins and/or carcinogens etc., or a combination thereof).

In one embodiment, aspects of the technology described herein can be employed to diagnose, evaluate or stage diseases associated with changes in vasculature structure. The detection of small changes in vasculature structure may be informative for early stage disease detection and disease monitoring. A morphological determination of binned blood vessels may be analyzed and one or more patterns (e.g., individual structural features or distributions) may be evaluated for the presence of abnormal properties. In one embodiment, a vasculature structure may be obtained including a series of interconnected branched blood vessels and may include arteries, arterioles, veins, venules, capillaries, and other sized blood vessels. However, according to aspects of the technology described herein, an interconnected vasculature structure is not required and different sizes of blood vessels can be analyzed separately and represented on a histogram or other form of distribution representation. In some aspects of the technology described herein, blood vessels of the entire body can be analyzed, and in other aspects the blood vessels of a target organ, tissue, or part thereof can be analyzed. In some aspects of the technology described herein, only a subset of blood vessel sizes is binned and analyzed (e.g., blood vessels with a diameter below about 500 microns, preferably below about 200 microns, more preferably below 100 microns, even more preferably below 50 microns, and even more preferably below 25 microns). In one embodiment, only capillary blood vessels are analyzed. In another embodiment, capillaries and small arteries and veins (e.g., arterioles and venules) are analyzed. For example, an arborescent vasculature can be analyzed in any tissue where it is found (e.g., an arborescent mucosal vasculature such as the oesophageal arborescent mucosal vasculature).

The branches of a vascular tree may be analyzed to glean information about the status of the patient. In one embodiment, the branches of a vascular tree may be followed to identify specific regions where certain characteristics of angiogenesis may be evaluated (e.g., start with a large branch and follow the tree to second, third, or fourth, or subsequent levels of branching to identify small blood vessels that may have abnormal structures if they are providing a blood supply associated with a disease). Alternatively, several different blood vessel sizes in the vascular tree may be evaluated for signs of angiogenesis. In another embodiment, the overall branching pattern of a vascular tree can be analyzed. For example, a healthy vascular tree may be approximately hierarchical in that the size of the blood vessels generally decreases as the vessels branch. In contrast, a diseased (e.g., angiogenic) vascular tree may be less hierarchical with areas of significant blood vessel branching with little or no decrease in blood vessel size. It should be appreciated that the nature and extent of the analysis may depend on the goal of the diagnostic evaluation. For example, a full body scan can be evaluated selecting all vascular structures and analyzing the entire vascular network for signs of different diseases. Alternatively, a region of a body suspected of being diseased may be selected and the data may be processed to focus on the vasculature in that region (e.g., to obtain a segmented representation of structures in the region of interest). A region of interest may be an organ (e.g., pancreas, liver, kidneys, breast, colon, etc.) or a tissue (e.g., skin epidermal tissue, retinal tissue). The presence of an abnormal vasculature structure can be an early indication of a range of diseases for which early detection is critical for effective treatment (e.g., retinal vascular changes are a common precedent to the development of diabetes and hypertension).

Diseases associated with changes in vascular structure (e.g., that can be detected by the presence of abnormal vascular patterns at a given time or abnormal structural changes observed as a function of time) include, but are not limited to, cancer, heart diseases and related circulatory disorders, eye diseases, skin disorders, and surgical conditions. For example, diseases and conditions associated with changes in vascular structure include, but are not limited to, tumor angiogenesis, recurrent and progressive cancers, coronary artery disease, cardiomyopathy, myocardial ischemia, arteriosclerosis, atherosclerosis, atherosclerotic plaque neovascularization, arterial occlusive disease, ischemia, ischemic or post-myocardial ischemia revascularization, peripheral vascular disease (including diabetic retinopathy), thromboembolic diseases (e.g., stroke, pulmonary embolism, brain aneurisms, and deep venous thrombosis), claudication, rheumatologic disorders (e.g., arthritis), immune disorders (e.g., rheumatoid arthritis, vasculitis, Wegner's granulomatosis, and systemic lupus erythematosis (SLE)), pulmonary disorders (including, emphysema, COPD, idiopathic pulmonary fibrosis, pulmonary arterial hypertension, and other respiratory disorders), myeloma, vascular proliferative disorders, gastrointestinal disorders (e.g., Crohn's disease, ulcerative colitis, and inflammatory bowel disease (IBD)), gynecologic disorders (endometrial polyp, vaginal bleeding, endometriosis, dysfunctional uterine bleeding, ovarian hyperstimulation syndrome, preeclempsia, polycystic ovarian syndrome (PCO), cervical cancer, and cervical dysplasia), skin disorders (infantile hemangioma, verruca vulgaris, psoriasis, neurofibromatosis, epidermolysis bullosa, Stevens-Johnson syndrome, and toxic epidermal necrolysis (TEN)), eye disorders (macular degeneration, maculopathies, diabetic retinopathy, and retinopathy of prematurity (retrolental fibroplasia)) wound healing, inflammation associated with immune responses, ischemia including limb ischemia and cardiac ischemia, Alzheimer's disease and other disorders such as wound dehiscence, Buerger Disease (thromboangitis obliterans, arteriosclerosis obliterans (ASO), ischemic ulcers) multiple sclerosis, idiopathic pulmonary fibrosis, HIV infections, plantar fasciosis, plantar fasciitis, Von Hippel-Lindau Disease, CNS hemangioblastoma, retinal hemangioblastoma, thyroiditis, benign prostatic hypertrophy, glomerulonephritis, ectopic bone formation, and keloids.

These different diseases are characterized by different changes in vasculature structure. Accordingly, in one aspect of the technology described herein, parameters and scoring methodologies are used to detect, diagnose, and monitor particular diseases and their related therapies based upon particular characteristics of vasculature structure indicative of the disease. Even within each disease category, different diseases can be characterized by different changes in vasculature structure. Accordingly, structure mining and scoring can be fine-tuned to increase the sensitivity for particular types of disease within a category (e.g., lung cancer score, breast cancer score, etc., can be developed). Patient-specific scoring parameters can also be developed to follow the progression of a specific disease or disorder in a patient.

Structural vasculature changes include changes in vascular architecture and vascular morphology affecting blood vessels and/or lymph vessels. Structural changes can involve neovascularization (including the growth of large blood vessels (e.g., arteriogenesis) and the growth of microvasculature (angiogenesis)), large blood vessel expansion, and vascular necrosis. Angiogenesis involves the formation of new blood vessels that sprout from preexisting blood vessels. Angiogenesis is different from vasculogenesis, which is the de novo formation of vessels that occurs primarily during development. Vasculogenesis is rarely associated with a disease or disorder. However, aspects of the technology described herein can be used to study the natural process of vasculogenesis to help identify and understand defects in de novo blood vessel formation.

Angiogenesis is often associated with tumor growth and is a useful biomarker for cancer. Angiogenesis also can be associated with conditions where new blood vessel growth occurs in response to a reduced oxygen supply or blood flow (whether due to thrombosis, embolism, atherosclerosis, or other chronic occlusion or narrowing of the vasculature). Certain respiratory, cardiovascular, and inflammatory disorders also are associated with angiogenesis.

Angiogenic blood vessels have structural characteristics that are different from those of established blood vessels. For example, the branching patterns and tortuosity of angiogenic blood vessels are very different from those of normal blood vessels. These and other structural features are found predominantly in microvasculature and can be used for mining and scoring vasculature structural images. However, changes in larger blood vessels such as arteries and veins also may be associated with certain diseases or disease stages (e.g., growth and development of large tumors or late-stage tumors). The vasculature that supports a tumor is typically associated with the connective tissue of the tumor (the stroma) that supports the malignant cells (in the parenchyma). As discussed herein, tumor blood vessels are irregularly spaced and characterized by heterogeneous structural patterns or features. However, the formation of tumor blood vessels and other forms of angiogenesis may involve a series of characteristic stages (see, for example, Dvorak, 2003, American Journal of Pathology, Vol. 162:6, pp. 1747-1757, the disclosure of which is incorporated herein by reference in its entirety). Early stage angiogenesis may be characterized by vascular hyper-permeability, fibrin deposition and gel formation, and edema. This may result in the enlargement of micro-vessels such as venules. The cross-sectional area of an enlarged micro-vessel may be about 4 fold that of a normal micro-vessel. The perimeter of an enlarged micro-vessel may be about 2 fold that of a normal micro-vessel. Enlarged micro-vessels may occupy about 4-7 fold the volume of normal micro-vessels in a region of active angiogenesis. The appearance of enlarged micro-vessels may be followed by the appearance of "mother" vessels that are enlarged, thin-walled, serpentine, and hyper-permeable. Mother vessels may undergo a process of bridging whereby trans-luminal bridges are formed dividing the blood flow within the vessel into smaller channels. A developing mother vessel also may contain one or more glomerular bodies that may expand to divide the lumen of the mother vessel into several smaller channels that are typically tortuous. Bridging and glomerular body formation in mother vessels may lead to the appearance of small capillaries characteristic of angiogenesis. However, certain mother vessels persist as abnormally enlarged vessels with thin walls. These vascular malformations are often characterized by the presence of an asymmetric muscular coat and perivascular fibrosis. Small arteries and arterioles also may increase in size in diseased tissue. Aspects of the technology described herein include detecting and/or monitoring any one or more of the blood vessel structural changes described herein. In one embodiment, the presence of one or more patterns (e.g., individual structural features or distributions) characteristic of new blood vessel formation may be used to detect or monitor a disease. In another embodiment, the presence of one or more specific patterns (e.g., individual structural features or distributions) may be used to determine the stage of angiogenesis (e.g., early-stage, mid-stage, late-stage, etc.) in a body region.

Accordingly, abnormal changes in blood vessel size (diameter and/or length) can be early signs of diseases such as cancer or other disease associated with an increased blood supply. Changes in blood vessel size may occur before any structural signs of angiogenesis appear. In one embodiment, aspects of the technology described herein are useful to detect blood vessels (e.g., capillaries) that are swollen and/or longer than normal. For example, aspects of the technology described herein are useful to detect abnormally long intrapapillary capillary loops in situ (e.g., associated with early stages of cancer in oesophageal mucosa).

In some embodiments, blood vessel changes indicative of necrosis in tumor tissues may be indicative of the aggressiveness of the tumor tissue and/or the likelihood of metastasis, and/or the responsiveness to therapy, and/or the efficacy of a therapeutic treatment (e.g., a candidate drug), and/or an therapeutic treatment selection and/or modification (e.g., a change in drug or dose for an individual patient). Accordingly, in situ patterns (e.g., individual structural features or distributions) indicative of necrosis may be useful biomarkers for patient prognosis. In certain embodiments, necrosis within a region of a tumor may be indicated by one or more of the following patterns (e.g., individual structural features or distributions) within that region: a collapse in blood vessel structure, poor vascularization (e.g., a low blood vessel density relative to other regions of the tumor or relative to the perimeter of the tumor), a change in blood vessel size or shape over time, a lower than threshold number of blood vessels, blood vessels (e.g., in the microvasculature or the capillaries) that are separated by a greater than threshold distance (e.g., by more than 100 microns, more than 150 microns, or more than 200 microns) within a volume of the tumor, micro-vessel diameter and/or density indicative of undervascularization, etc., or any combination thereof. In some embodiments, a volume of avascularization or undervascularization may be evaluated or quantified and used as an indicator of necrosis. It should be appreciated that other indicia of necrosis may be used, alone or in combination with blood vessel features. Other indicia may include indicia of tissue collapse or cavitation that may be visualized (e.g., using CT etc.) and/or indicia of tissue viability using one or more markers of metabolic activity (e.g., ones that may be analyzed using a PET scan, etc.). One or more reference indicia (e.g., a reference volume of avascularization or undervascularization may be identified by analyzing vascular casts of necrotic tumor tissue (e.g., in a xenograft tumor model, for example in an orthotopic or an ectopic tumor xenograft). Aspects of the technology described herein may be used for the detection (e.g., the automatic detection) of necrotic areas in a subject (e.g., in a tumor in a subject). A necrotic region is an avascular region within the boundary of a diseased tissue. Methods of the technology described herein may be used to detect (e.g., automatically) the transition between the vascularized diseased tissue and avascular region that defines the boundary of the necrotic region.

Aspects of the technology described herein also may be used to detect or evaluate (e.g., automatically) a response to therapy. For example, a response to therapy (e.g., to a specific drug and/or a specific dosage of a drug, and/or to a combination of drugs and specific dosages of these drugs, etc.) can be detected and assessed as follows. Changes in the vascular patterns (e.g. vessel normalization/straightening, disappearance of smaller diameter vessels leading to lower micro-vessel density and to skewing of the vessel diameter distribution towards the larger vessels) may be detected and/or evaluated within the volume defined by the boundary of the diseased tissue and the boundary of the necrotic area. An increase in the absolute volume size of the necrotic area and/or the rate of such change while the total volume of the disease (e.g. tumor) volume stays constant may be detected and/or evaluated as an indicator that the therapy is effective. An increase in the ratio between the absolute volume size of the necrotic area and the total disease (e.g., tumor) volume and/or the rate of change in this ratio may be detected and/or evaluated and used as an indicator that the therapy is effective. A ratio of the diseased tissue volume and the necrotic region volume may be detected and/or evaluated and when it approaches 1 and the overall diseased tissue volume starts shrinking it provides an indication that a therapy is effective. In some embodiments, reference indicia may be obtained from analyzing casts (e.g., appropriate vascular casts). However, reference indicia may be obtained from any suitable data relating to blood vessel structures (e.g., view data, scan data, in vivo data, etc., or any combination thereof).

Structural representations of blood vessels can be mined to identify and evaluate certain patterns (e.g., individual structural features or distributions) that can be used to provide a score that is related to the probability that the blood vessels are normal or abnormal (e.g., disease associated). Accordingly, in some embodiments a binned analysis may be predictive of a response to therapy.

In certain embodiments, a binned analysis may be sensitive to vasculature changes resulting from unwanted side-effects associated with one or more therapeutic drugs. Accordingly, binned analysis may be used to detect or quantify toxic side-effects of certain drugs.

The morphology of blood vessels (e.g., binned blood vessels) can be mined to identify and evaluate certain patterns (e.g., individual structural features or distributions) that can be used to provide a score that is related to the probability that the blood vessels are normal or abnormal (e.g., disease associated). Patterns (e.g., individual structural features or distributions) for scoring blood vessels include, but are not limited to, the following: diameter, curvature, tortuosity (including, for example, the degree of tortuosity, the length of the blood vessel along which abnormal tortuosity is observed, etc.), variability or heterogeneity (including spatial variability or heterogeneity over distance or in a volume), branching shape or pattern, branching density, branching hierarchy, blood vessel density, distribution of vessel size (ratio of microvasculature to macrovasculature) a field effect (the presence of blood vessels bending towards a specific region), blood vessel diameter distribution, variability of the geometric orientation of blood vessels or fragments thereof, and the distribution of the orientation(s) within a field. The score may have more significance if two or more (e.g., 3, 4, 5, 6, 7, 8, 9, 10, or more, or all) of these parameters are evaluated. In some embodiments, a score is generated using one or more of these structural parameters combined with additional information such as patient-specific medical information (e.g., age, weight, height, gender, etc.) and the presence of one or more additional indicators of disease such as a visible lesion on an X-ray or other image. In some embodiments, a score can be provided for a tumor. An example of a useful score is one that reflects the vascularity of a tumor. An abnormally high vascularity (measured as a higher than normal blood vessel number, density, length, or combination of the above) is generally indicative of a more aggressive or invasive tumor. In one embodiment, vascularity is evaluated by measuring the volume of the lumen of angiogenic vasculature (the volume within the blood vessel tree associated with a tumor). In another embodiment, a measure of vascularity is provided by dividing the volume of the angiogenic lumen by the volume of the solid tumor. Additional information can be gleaned from obtaining a score (or other structural evaluation) at two or more times. A changing score (or other structural evaluation) is indicative of an evolving vasculature that could be associated with a disease or disorder. It should be appreciated that the patterns (e.g., individual structural features or distributions) described herein can be identified and analyzed for a field of analysis without imposing a connectivity on the vessels being studied. In some embodiments, it may be sufficient to analyze only fragments of blood vessels in order to detect one or more structural features of individual vessels or geometrical features of a field of vessels that are different from normal features. For example, blood vessel fragments having an average length of 0.5 mm, 1 mm, 5 mm, 10 mm, 50 mm, 1 cm, 5 cm, 10 cm, 50 cm, etc. may be used. However, it should be appreciated that shorter or longer or intermediate lengths may be used. The scoring and mining aspects of the technology described herein can be automated. Accordingly, diseased (e.g., angiogenic) vasculature can be automatically detected amidst normal vasculature. Various vasculature parameters can be automatically detected and scored, either separately or in any combination, including vessel tortuosity, vessel branching, vessel density, and total intra-vascular volume, but the technology described herein is not limited to any particular parameter or combination.

In one embodiment, aspects of the technology described herein can be used to detect blocked blood vessels, and thromboembolic events, including stroke, lung emboli, blocked micro-coronaries, deep-vein thrombosis, etc. Blocked blood vessels can be detected (1) directly by detecting structural changes in the blocked blood vessel (e.g., detecting a clot, wall thickening, or other signs of reduced flow) and/or (2) indirectly by detecting new vasculature that was generated in response to the blockage. In general, the formation of collateral blood vessels is more ordered than angiogenesis associated with cancer. One aspect of the technology described herein described herein also allows clots to be detected in small blood vessels.

As discussed herein, aspects of the technology described herein can be used to screen the entire vasculature structure of a human or other animal to screen for any form of abnormality in any tissue. Alternatively, a subset of the body may be screened. Accordingly, the structures of binned vessels can be analyzed for one or more organs or tissue types. In addition, only a portion of the vessels in any predetermined bin may be analyzed within any target volume as opposed to the entire vascular tree in that volume. This may be done by analyzing structure data focused on the area of interest, or large amounts of structure data may be obtained, but an analysis may be restricted to a subset of the available data. In some embodiments, only a portion of a vascular tree may be binned and/or analyzed, for example only a portion of those vessels that are of a particular size range. In some embodiments, only fragments of a vascular tree are represented and/or analyzed if the fragments are sufficiently informative to provide patterns (e.g., individual structural features or distributions) of interest. Fragments may include branches or may be unbranched. The portion of the vasculature being analyzed may be statistically significant, such that any observation (normal or abnormal) is physiologically significant. For example, branched structures may not be required for the analysis if a sufficient number of vessel substructures are analyzed to confidently detect any other patterns (e.g., individual structural features or distributions) that may be associated with vasculature changes (e.g., angiogenesis) such as high vessel density. In aspects of the technology described herein, vascular patterns may be detected and/or evaluated in situ in a volume of 1 $mm^3$, 2 $mm^3$, 5 $mm^3$, 1 $cm^3$, 2 $cm^3$, 5 $cm^3$, 10 $cm^3$, etc. However, smaller or larger or intermediate volumes also may be analyzed. In some embodiments, vascular patterns or structures are evaluated over an entire model tissue or organ (e.g., for an entire orthotopic or ectopic tumor model).

Different tissues and organs have different and characteristic blood vessel patterns (e.g., the lung which is highly vascularized). Accordingly, in one embodiment, structural analyses and associated structural parameters may be optimized for evaluating different tissues.

In some embodiments, scan data is obtained and/or analyzed for one or more organs (e.g., lung, heart, colon, brain, liver, pancreas, kidney, breast, prostate, etc.) or tissue (e.g., skin, bone, etc.) or portion of any of the above.

Brains may be evaluated for signs of brain tumors and/or other neurological disorders that can be associated with changes in vascular patterns. For example, Alzheimer's may be associated with certain vascular abnormalities. In one embodiment, one or more changes in blood vessel pattern (e.g., shape and/or size) may be detected as an indicator of high blood pressure in the brain.

In some embodiments, certain specific regions of organs or tissues are focused on. For example, atherosclerosis is typically found in certain parts of the arterial tree (e.g., bifurcations, side branches, regions opposite flow dividers, and other areas where angiogenesis often occurs in association with atherosclerosis) and certain cancers tend to occur more frequently in certain organ or tissue regions (e.g., colon cancers are not distributed evenly along the length of the colon).

In other embodiments, aspects of the technology described herein may be used to follow up with individuals who have been identified as having one or more other indicia of disease (e.g., fecal occult blood, a colon polyp, a lung nodule, one or more cysts or other indicia of disease). Aspects of the technology described herein may be used to confirm the presence of a disease, determine a location for the disease-associated lesion, or provide an evaluation or prognosis of a disease. For example, aspects of the technology described herein may be used to determine whether abnormal vasculature is present at the site of a lesion (e.g. a colon polyp, a lung nodule, a bladder cyst, a prostate cyst, a breast cyst, a spot on a mammography, or any other cyst, lump, or spot that may be detected physically, visually, or using any other diagnostic technique) and help evaluate the likelihood of a malignancy (or other carcinogenic disease stage) associated with the lesion. Accordingly, aspects of the technology described herein may be used for virtual malignancy detection (e.g., virtual colonoscopy, virtual colon malignancy detection, virtual bronchoscopy, virtual lung malignancy detection, virtual mammography, virtual cystoscopy, etc.).

In other embodiments, aspects of the technology described herein may be used for screening a cancer patient to evaluate the extent of a cancerous lesion and/or to screen for the presence of one or more metastatic lesions (e.g., one or more loci associated with angiogenesis). A cancer patient may be screened upon initial diagnosis of a primary cancer. In addition or alternatively, a cancer patient may be screened at least once after an initial cancer treatment (e.g., surgery, radiation, and/or chemotherapy). This screening may include the original cancer locus to detect any cancer recurrence. This screening may include similar body tissue to screen for the presence of other lesions in the same tissue or organ (e.g., the entire colon may be screened when a cancerous lesion is detected in one region of the colon, the second breast may be screened when a cancerous lesion is detected in one breast, etc.). This screening also may be extended to the whole body or to one or more other loci suspected of containing a metastatic lesion. In one embodiment, a cancer patient may be screened several times after an initial cancer treatment (e.g., at time intervals of about 6 months, about 1 year, about 2 years, about 5 years, or at other time intervals).

In one embodiment, a follow up procedure may involve screening one or more organs or tissues for the presence of a metastatic lesion. Different cancers may have different characteristic patterns of metastasis. Accordingly, different target loci may be screened for different cancers. For example, metastatic breast cancer typically spreads to the lungs, the liver, bone, and/or the CNS. Therefore, one or more of these tissue types or organs may be screened after a patient is diagnosed with breast cancer. Similarly, other target loci may be screened after a patient is diagnosed with another cancer type. In some embodiments, the entire body of a cancer patient may be screened for indicia of metastasis.

In one aspect, an initial screen may be performed on an entire body, or an entire organ, using a low resolution representation and/or, for example, analyzing only one or two or a small number (e.g., less than five) pattern parameters in order to detect indicia of a disease. Subsequently, the presence and or nature of the disease may be diagnosed using a higher resolution representation and/or, for example, analyzing one or more additional pattern parameters or alternative pattern parameters than those that were analyzed for the initial detection.

In some embodiments, small changes in blood vessel distributions may be observed (for example as measured by a ratio between the number of blood vessels of two or more different sizes in a region of interest, for example, a tumor in an animal model) and used as a biomarker. Such biomarkers may represent early changes (e.g., early changes in tumor growth or response to therapy) that occur before later changes in tumor size and/or tumor morphology. It should be appreciated that some or all of the diagnostic aspects of the technology described herein can be automated as described herein.

It should be appreciated that some or all of the diagnostic aspects of the technology described herein can be automated as described herein.

Aspects of the technology described herein also can be used to identify the location of a disease by locating one or more structural abnormalities associated with the disease. This information can be used to target a biopsy procedure or a treatment (e.g., a treatment with one or more toxic chemicals, radiation, heat, cold, small molecules, gene therapy, surgery, any other treatment, or a combination of two or more of the above) to the precise location of a disease lesion, or for any other purpose.

In one embodiment, an imaging device is connected to a computer that provides a real-time visual display of the disease lesion. In one embodiment, a real-time visual display may be an accurate model of a body region and lesion along with associated vasculature (as opposed to an actual image). This visual information can be used to guide a surgical instrument for a biopsy. Alternatively, the information can be used to guide an invasive (e.g., surgical removal or bypass) or non-invasive (e.g., radiation) treatment procedure to the site of the disease lesion (e.g., tumor or blood clot).

In some embodiments, aspects of the technology described herein may be used to define the boundary between diseased and non-diseased tissues, or between necrotic and non-necrotic tissue, etc., or any combination thereof. For example, a boundary may be identified or defined by analyzing binned data for several areas of interest and identifying adjacent areas having very different blood vessel densities (or differences in other morphological parameters that are associated with disease, necrosis, etc., or any combination thereof.

In one embodiment, aspects of the technology described herein may be used to identify an area of tissue for treatment before the treatment is applied. For example, a treatment target region may be identified by detecting a boundary of chaotic blood vessel structures. The area may be assessed after treatment to confirm that the treatment was appropriately targeted. In one embodiment, a structure may be analyzed pre-operatively to identify the extent of tissue to be removed from a body region. In one embodiment, a body region may be analyzed post-operatively to determine whether any abnormal structures were missed. This may be used to confirm the success of a radiation treatment or a surgical removal of diseased tissue. Alternatively, this may be used to decide on further surgery and/or another form of treatment. In another embodiment, a disease boundary may be defined or depicted by the boundary of abnormal vasculature. A treatment (e.g., radiation therapy, surgery, etc.) may be guided by and/or restricted to a volume encompassed by the disease boundary.

In one embodiment, aspects of the technology described herein can be used to evaluate the success of a surgical implant or transplant. For example, aspects of the technology described herein can be used to evaluate the formation of new blood vessels after an organ or tissue transplant.

In another embodiment, the development of new blood vessels may be monitored after removal of tumor tissue or after a tumor biopsy, both of which may trigger angiogenesis and/or convert a dormant tumor into a malignant tumor.

It should be appreciated that some or all of the interventional aspects of the technology described herein can be automated as described herein.

Aspects of the technology described herein also can be used to optimize a therapeutic treatment for a patient. The extent of disease progression or regression can be monitored in response to different treatment types or dosages, and an optimal treatment can be identified. The optimal treatment may change as the disease progresses. The effectiveness of the treatment over time can be monitored by analyzing changes in disease-associated patterns (e.g., individual structural features or distributions) using the aspects of the technology described herein described herein.

In one embodiment, a first therapy can be administered and its effectiveness on slowing, stopping, or reversing abnormal blood vessel growth can be monitored either irregularly or at certain time intervals (e.g., daily, weekly, monthly, or other time intervals). In some embodiments, if a first therapeutic regimen does not have a desired effect on disease progression, a second therapeutic regimen can be evaluated. Similarly, additional therapeutic regimens can be evaluated on a patient-by-patient basis. Additionally, the technology described herein can be used to optimize a chosen therapeutic regimen (e.g., optimize dosage, timing, delivery, or other characteristic of a drug or other treatment) by monitoring the effect of minor therapeutic changes and using the conditions that appear to be most effective for the condition and the patient.

When looking at the therapeutic effectiveness of a treatment, disease-specific parameters may be monitored. Of course, all parameters can be obtained and only a subset reviewed. However, it may be more efficient to simply obtain binned data only for those parameters that characterize the disease.

According to aspects of the technology described herein, patterns (e.g., individual structural features or distributions) that are used to detect angiogenic vasculature and other abnormal blood vessels also can be used to monitor a disease response to treatment. For example, the total vascularity or any other volumetric analysis of angiogenic or other diseased vasculature, and the distribution of vessel size (e.g., a ratio of small to large blood vessels) can be used independently or together as indicators of disease progression or regression. In general, microvasculature disappears before macrovasculature if an anti-angiogenic treatment (or other disease treatment) is effective. Therefore, an effective treatment results in a shift in the distribution of blood vessel sizes towards larger vessels. An index of anti-angiogenic activity can be scored as either a loss of small blood vessels or a shift of observed blood vessels towards a single size (or both).

In another aspect, the parameters can be (or include) changes over time. For example, a structure present at a second time can be compared to a structure present at a first time. In one embodiment, a disease may be tracked pre-therapy and/or post-therapy. Naturally, additional time points can be used. The time points may depend on the condition being observed (e.g., is it the progression of a disease that is already identified, is it the screening of patient(s) over time). Time periods can be daily, weekly, monthly, annual, or shorter, intermediate or longer time periods. Time intervals may be a series of regular time periods. However, other time intervals may also be useful. In one embodiment, a patient-specific baseline is established and monitored over time. For example, vasculature changes in the colon, breast, or other tissue or organ can be monitored periodically.

In one aspect of the technology described herein, a type of treatment may be determined by the degree or extent of abnormal vascular structures (e.g., angiogenesis) that is detected at one or more suspected disease loci (e.g., cancerous loci). For example, if a suspected cancerous locus or metastasis is pre-angiogenic or associated with early stage angiogenesis, it may be appropriate to monitor the locus without any form of treatment. However, an appropriate therapy may involve the administration of one or more angiogenesis inhibitors to prevent the formation of any new vasculature. If a suspected cancerous locus or metastasis is associated with mid-stage angiogenesis, an appropriate therapy may be the administration of one or more angiogenesis inhibitors. A patient with mid-stage angiogenesis at a suspected locus also should be monitored so that any further blood vessel development can be treated more aggressively. If a suspected cancerous locus or metastasis is associated with late stage angiogenesis, an appropriate treatment may involve at least one or more of chemotherapy (e.g., cytotoxic chemotherapy and/or hormone-based chemotherapy), radiation, surgery, and/or treatment with one or more angiogenesis inhibitors. However, it should be appreciated that any of the above treatment options may be used to treat a patient with any one or more lesions associated with any degree of angiogenesis.

Examples of angiogenesis inhibitors include but are not limited to 2-methoxyestradiol (2-ME), AG3340, Angiostatin, Angiozyme, Antithrombin III, VEGF inhibitors (e.g., Anti-VEGF antibody), Batimastat, bevacizumab (avastatin), BMS-275291, CAI, 2C3, HuMV833 Canstatin, Captopril, Cartilage Derived Inhibitor (CDI), CC-5013, Celecoxib (CELEBREX®), COL-3, Combretastatin, Combretastatin A4 Phosphate, Dalteparin (FRAGIN®), EMD 121974 (Cilengitide), Endostatin, Erlotinib (TARCEVA®), gefitinib (Iressa), Genistein, Halofuginone Hydrobromide (TEMPOSTATIN™), Id1, Id3, IM862, imatinib mesylate, IMC-IC11 Inducible protein 10, Interferon-alpha, Interleukin 12, Lavendustin A, LY317615 or AE-941 (NEOVASTAT™), Marimastat, Maspin, Medroxpregesterone Acetate, Meth-1, Meth-2, Neovastat, Osteopontin cleaved product, PEX, Pigment epithelium growth factor (PEGF), Platelet factor 4, Prolactin fragment, Proliferin-related protein (PRP), PTK787/ZK 222584, ZD6474, Recombinant human platelet factor 4 (rPF4), Restin, Squalamine, SU5416, SU6668, SU11248 Suramin, Taxol, Tecogalan, Thalidomide, Thrombospondin, TNP-470, TroponinI, Vasostatin, VEG1, VEGF-Trap, and ZD6474.

Some embodiments may include a method of selecting a subject for treatment and/or selecting a treatment or a course of therapy based on the analysis of certain in situ vascular structures. A method may involve analyzing in situ vascular structure(s) in a human subject to obtain, for example, a score. The score may be compared to a control score (e.g., in an apparently healthy population) or to a previous score from a previous analysis on the same subject. The treatment or the course of therapy may be based on such a comparison. In some embodiments, obtaining an analysis of vascular structures is repeated so as to monitor the human subject's response to therapy over time. In some embodiments of this aspect of the technology described herein, the method further comprises measuring a second index of disease in the human subject wherein deciding on the treatment or course of therapy is also based upon the measurement of said second index.

In certain embodiments, patients having a tumor that is under-vascularized (e.g., one that shows signs of necrosis) may be selected for treatment with one or more anti-angiogenic compounds. Under-vascularized tumors may be identified as those that have a low density of blood vessels, or for which the blood vessel diameters are low (e.g., below a threshold number typical of vascularized tumors).

Aspects of the technology described herein also may include monitoring the effectiveness of a therapy by monitoring the presence of blood vessel patterns or features over time. For example, the progressive loss of blood vessels in a tumor in response to treatment may be a sign that a therapy is effective. In contrast, the absence of any impact on vascularization may be an indicator that a treatment is not being effective in a patient and that an alternative therapy should be considered or used.

It should be appreciated that some or all of the therapeutic aspects of the technology described herein can be automated as described herein.

In one embodiment, aspects of the technology described herein can be used to understand structural changes associated with biological processes of interest (e.g., disease development and progression). For example, an animal's vasculature can be analyzed to identify additional patterns (e.g., individual structural features or distributions or changes associated only with certain binned size ranges) that may be associated with wound healing or different diseases or different disease stages. These additional patterns (e.g., individual structural features or distributions) may be used in one of more of the diagnostic, intervention, therapeutic, and development aspects of the technology described herein.

In one embodiment, aspects of the technology described herein can be used to understand structural changes associated with medical procedures. For example, an animal's vasculature can be analyzed to identify changes associated with post-surgical wound healing or implant/transplant (including xenografts) growth or rejection.

It should be appreciated that some or all of the research aspects of the technology described herein can be automated as described herein.

In another embodiment, aspects of the technology described herein can be used in screens of compound libraries or to validate candidate compounds for treating diseases associated with abnormal internal structures (e.g., abnormal tubular networks). Aspects of the technology described herein allow efficient high throughput analyses of internal structural changes using binned data (e.g., BMVD). These changes can act as surrogate markers (biomarkers) for certain diseases. As a result, the screening process can be automated to a large extent, and the time for obtaining results significantly shortened when compared to current validations that often involve waiting for disease symptoms to change and also may require tissue biopsies.

Aspects of the technology described herein may be used for identifying and quantifying vascular patterns (e.g., structural features) that can be used as surrogate markers for diagnostic, therapeutic, and research and development purposes. Surrogate markers are useful for reducing the time of diagnosis, therapy evaluation, and drug development. A surrogate marker can be used as an early indicator for disease diagnosis, disease prognosis, or drug effectiveness, without waiting for a clinical outcome (e.g., increased survival time in response to a drug). So, a vasculature analysis can be used as a surrogate marker for drug development (in both pre-clinical and clinical trials), for clinical screening (e.g., breast, lung, or colon screening), and for clinical therapy monitoring. For example, binned vasculature structure may be a useful surrogate marker for angiogenesis related diseases such as cancer.

In one embodiment, aspects of the technology described herein provide methods for screening and/or validating candidate compounds or therapies for their effectiveness in treating neo-vasculature formation and/or vasculature pattern changes associated with disease. Aspects of the technology described herein may be used to evaluate individual or small numbers of compounds or to screen libraries to evaluate and/or identify a plurality of candidate compounds (e.g., by administering these compounds, individually or in groups, to an experimental animal such as a mouse and evaluating their effect on angiogenic vasculature). Libraries may contain any number of compounds (e.g., from approximately 100 to approximately 1,000,000) Different types of compounds can be screened, including antibodies, small molecules, etc., or any combination thereof. However, the technology described herein is not limited by the number and/or type of compounds that can be evaluated.

In one embodiment, the effectiveness of a candidate compound can be compared to a reference compound. A reference compound can be any compound with a known effect on a structure. For example, Avastin (Genentech) is a known monoclonal antibody against vascular endothelial growth factor (VEGF) that can be used as a reference to test the effect of a candidate compound on neovasculature growth. Other examples of compounds include, but are not limited to, Sutent and Nexavar.

It should be appreciated that some or all of the development aspects of the technology described herein can be automated as described herein.

It also should be appreciated that any one or more geometrical, structural, and/or distributional parameters described herein may be evaluated by comparison to a reference parameter. In some embodiments, a reference parameter may be an amount or score for that parameter in a normal or healthy subject. In other embodiments, a reference may represent a diseased condition. In some embodiments, a change or amount of any structural parameter that is correlated or associated with a disease or condition as described herein may be a statistically significant change or difference in that parameter in a diseased or test subject relative to a reference subject. In some embodiments, a difference or change in a structural parameter may be an increase or a decrease in a particular parameter (or a combination of parameters). An increase in a parameter may be at least a 5%, 10%, 20%, 30%, 40%, 50%, 60%, 70%, 80%, 90%, 100%, or greater increase in that parameter in a test subject relative to a reference subject. Similarly, a decrease in that parameter may be at least a 1%, 5%, 10%, 20%, 30%, 40%, 50%, 60%, 70%, 80%, 90%, 100%, or greater decrease of a measure of that parameter in a test subject relative to a reference subject. Once an amount of change or difference in a parameter has been correlated or associated with a disease or condition, that level may be used in subsequent methods according to the technology described herein. Accordingly, in some embodiments, a difference of at least at least 1%, 5%, 10%, 20%, 30%, 40%, 50%, 60%, 70%, 80%, 90%, 100%, or more of any given structural parameter (e.g., tortuosity, density, volume, or any other individual structural feature or distribution of structures or structural features as described herein) within a data bin relative to a reference value may be used as a threshold for methods of the technology described herein. It should be appreciated that higher or lower or intermediate values may be used. It also should be appreciated that different parameters may have different threshold or reference levels. Also, different parameters (and/or different levels for each parameter) may be associated with different conditions or diseases. Accordingly, specific disease or condition values or thresholds may be identified for different parameters or combinations thereof. These threshold values may be used for disease detection, diagnosis, monitoring, or for any other therapeutic, clinical, or research application described herein (e.g., in automated methods described herein).

Accordingly, aspects of the technology described herein provide methods and devices for obtaining and/or analyzing data relating to internal tubular structures in casts and/or in human and/or other animal bodies. In some embodiments, methods of the technology described herein involve analyzing one or more parameters (or parameter changes over time) for binned blood vessels that have been categorized based on their size. For example, blood vessels may be binned according to the following non-limiting diameter ranges: about 0-10 microns, about 10-25 microns, about 25-50 microns, about 50-75 microns, about 75-100 microns, about 100-150 microns, about 150-200 microns, about 200-300 microns, about 300-400 microns, about 400-500 microns, about 500-1,000 microns, or any combination thereof. However, any other suitable bin size ranges (including larger, smaller, or intermediate size ranges) may be used. In some embodiments, the number of different bins may be between about 2 and about 10. However, higher numbers of bins also may be used. In some embodiments, only 2 to 5 bins are used (e.g., 2, 3, 4, or 5). In certain embodiments, three blood vessel bin sizes are used: small, medium, and large. In some embodiments, a single bin is chosen having a predetermined size range and no other size ranges are analyzed.

Profiles may be extracted from the distribution of quantitative values for one or more structural features as described herein (including for example, features observed in vascular casts). In some embodiments, volume independent or density independent profiles may be extracted from distributions by comparing ranges within each distribution being analyzed (e.g., a subpopulation within a single range as a percentage of the total population across all ranges, or a ratio of subpopulations within a first and a second range that each represent different subsets the entire range of values).

Aspects of the technology described herein may include the analysis of one or more regions of interest in animal disease models (e.g., in situ and/or in casts of one or more regions of interest). Animal disease models may be, but are not limited to, engineered (e.g., recombinant) animals, transgenic animals, metastatic cancer models, xenograft models, orthotopic transplant models, etc., or any combination thereof. In some embodiments, different animal models may have different known genetic markers (e.g., particular mutations) associated with a disease of interest (e.g., a cancer). Any suitable animal may be used as an animal model, including, but not limited to, a mouse, rat, hamster, guinea pig, pig, dog, cat, rabbit, zebrafish, or other suitable animal. It should be appreciated that whole experimental animals may be analyzed. However, in some embodiments, tissues and/or organs may be analyzed. In some embodiments, models may be based on xenografts (e.g., xenografts of cancer or tumor cells that will form cancer or tumor tissues in a host animal). For example, human cells may be introduced into a non-human host animal. Other uses of xenografts include analyzing responses to certain tissue and/or organ transplantation (e.g., a non-human tissue or organ into a human host). In some embodiments, vascular casts of regions of interest in an animal model may be obtained to thoroughly analyze the vascular structures, and/or changes therein, associated with the condition being modeled. In some embodiments, observations made on casts may be compared (e.g., using appropriate statistical techniques) to in vivo (e.g., in situ) observations to identify one or more common structural characteristics and/or changes that are statistically significant in vivo in association with a disease, condition, or response of interest. These can then be used in subsequent applications as described herein.

According to aspects of the technology described herein, compounds and therapies can be evaluated in the context of an in-vivo model such as an animal disease model. For example, a mouse with cancer or atherosclerosis can be used to evaluate, optimize, and identify useful therapies. Other animal models also can be used. Aspects of the technology described herein may be useful for high-throughput analyses because they can detect small changes in vasculature and can be used to evaluate a therapy in a short time period with minimal manipulation since little or no invasive procedures are required.

Vascular analysis aspects of the technology described herein can be used on an orthotopic model to test, for example, the effectiveness of a drug in a short period of time. For example, the effect of a candidate drug on angiogenesis in an orthotopic mouse tumor model may be quantifiable after about 5 days (e.g., between 1 and 10 days, depending on the model and the drug). In contrast, a subcutaneous cancer animal model requires approximately one month for tumor growth to be analyzed and compared to controls.

An orthotopic model can be used to model different diseases or clinical conditions. Examples include, cancer, tissue regeneration, wound healing (including healing after traumatic injury, healing after surgical intervention, healing of burnt tissue such as skin), tissue or organ transplant therapy, medical device implant therapy, other conditions associated with neovascularization or changes in normal vascular structure, or any combination of two or more of the above. However, the technology described herein is not limited by the type of orthotopic model or the type of disease or clinical condition that is being analyzed.

A single orthotopic disease model animal may be useful for testing more than one candidate drug molecule since the analysis does not involve sacrificing the model animal. Accordingly, once a test with a first candidate is complete, a subsequent candidate can be evaluated in the same model animal. A series of candidates can be tested in a single model animal, with appropriate controls, provided the model retains features of neovascularization that are necessary for the assay.

It should be appreciated that any of the geometrical, structural, and/or distributional parameters described herein may be used as biomarkers. Biomarkers of the technology described herein can be qualified and/or quantified and compared using standard statistical methods. These biomarkers can be compared on individual basis, but also in combination as a signature of vascular morphology and function. Whole signatures can be compared between treated and untreated samples, or samples with physiological and pathological vascular pattern.

It should be appreciated that in some embodiments, one or more of the biomarkers described herein may be used to aid in the diagnosis, prognosis, prediction, or other medical application along with other types of physiological and or biological markers (e.g., physiological measurements, genetic markers, etc., or any combinations thereof).

It should be appreciated that aspects of the technology described herein may be applied to features of vascular geometry (e.g., curvature, tortuosity, distributions of vascular structural features, etc., or any combination thereof) that are obtained from an analysis of vascular casts (e.g., using any suitable image analysis technique described herein or known in the art). In some aspects, vascular casts are analyzed to identify distributions of one or more blood vessel structural features (including, for example, abnormal excess or absence of blood vessels or blood vessel structures) that are associated with a disease or other condition of interest. Structural features identified in casts may be used as biomarkers or references to evaluate in situ vasculature, for example, to detect indicia of a disease or other condition of interest in a subject. Structural characteristics of vascular casts also may be used to evaluate therapeutic treatments, screen candidate compounds, and for other applications as described in more detail herein. In some embodiments, one or more structural parameters are analyzed over time (e.g., using a series of vascular casts obtained at different time points) to monitor and/or identify structural changes that occur during development, disease progression or regression, or in response to therapy. In some embodiments, structural analysis is performed on vascular casts obtained from experimental models (e.g., whole animal models, or organ or tissue models). However, in some embodiments, vascular casts are obtained and analyzed for one or more regions of interest (e.g., diseased regions) in dead animals, including for example dead humans (e.g., human cadavers).

As used herein, a vascular cast refers to a physical structure that is generated to represent blood vessels of an entire vasculature or portion thereof. A cast may be obtained by perfusing a vasculature or a vascular region (e.g., the blood vessels of an organ, for example, of a kidney or liver) with a casting material that solidifies (e.g., polymerizes) to form a stable structure. The surrounding tissue and cells (e.g., including the blood vessel walls) may be removed to reveal the cast. The cast retains the structural features of the original blood vessels. Cast may include structures of blood vessels of different sizes as described herein. Certain casts are more flexible than others, certain casts are more brittle than others. Vascular casts can be used to identify vascular structural features with high resolution and/or to identify correlations between structural features and conditions of interest with high degrees of confidence since the structures of the blood vessels are retained in the casts and other biological structures that could interfere with an analysis are removed. Vascular casts may be obtained using any suitable casting material. In some embodiments, the casting agent may be a polymer. In some embodiments, the casting agent may react with the blood vessel walls. Non-limiting examples of casting agents include, but are not limited to Microfil®, methyl methacrylate, prepolymerized methyl methacrylate (Mercox™), Mercox™ CL-2B, other acrylic resins, silicon, gold nanoparticles, Batson No. 17, polyurethane-based casting agents (e.g., PU4ii), etc., or combinations of two or more thereof.

It should be appreciated that casting agents may be supplemented with contrast agents and/or other detectable agents. Examples of contrast agents include, but are not limited to, $BaSo_4$ and UAc (e.g., mixed into the casting material). In some embodiments, already polymerized casts can be soaked in $OSO_4$ to achieve better contrast using CT imaging. In certain embodiments, any suitable heavy metal can be mixed into the resin to make it more radioopaque.

In some embodiments, a large volume of an animal body (e.g., the entire body) may be perfused with a casting agent composition. In certain embodiments, a small volume of an animal (e.g., a tissue, an organ or a region of either one thereof) may be perfused with a casting agent composition. In some embodiments, a casting agent may be perfused into a tissue or an organ or a region of either one thereof after removal from an animal (e.g., after biopsy or other surgical excision). In some embodiments, a casting agent composition may be perfused into a live animal. It should be appreciated that an animal may be sacrificed after perfusion with a casting agent depending, in part, on the amount and type of casting agent composition that is used and the tissue or organ to which the casting agent composition is targeted. According to aspects of the technology described herein, casting agent(s) may be used to preserve in vivo structures for detailed analysis. In some embodiments, this analysis identifies particular structural or distribution properties that can be subsequently used as markers for in vivo diagnostic, therapeutic, research, and/or other applications in live animals (including humans).

In some aspects, vascular structures may be analyzed in situ in an animal after perfusion with a casting agent composition. In some aspects, a tissue or an organ or a region of either one thereof may be removed from an animal for analysis (e.g., before or after perfusion with a casting agent composition).

Accordingly, aspects of the technology described herein can be used to represent and/or visualize blood vessels with a casting agent or medium.

Data relating to one or more selected structures (e.g., structural patterns obtained from an analysis of a vascular cast) may be obtained and/or analyzed to glean information about a physiological condition of an animal based on the structure (or changes in the structure). For example, patterns identified in casts may be used as biomarkers to screen in situ vasculatures for the presence of one or more similar patterns to or to quantify the extent of the pattern in situ. This information may be used for diagnostic, predictive, prognostic, therapeutic, interventional, research and/or development purposes, as well as for grading and/or staging a disease. In some embodiments, methods of the technology described herein may involve analyzing one or more structural parameters (or one or more structural parameter changes over time) based on binned structure data or information obtained for casts (e.g., vascular casts) or in situ structures (e.g., in vivo blood vessels).

In some embodiments, one or more structures and/or structural changes that are identified using casts may be detected or monitored in vivo to determine whether a predetermined disease, condition, or response is present in vivo.

In some embodiments, structural parameters and/or structural changes observed for vascular casts from experimental animals (or organs or tissues) can be used as references when analyzing vasculature in vivo. For example, structural vasculature parameters and/or changes that are identified in casts using experimental animal models subsequently can be detected or monitored in vivo (e.g., in a human subject) and used to evaluate the development of a disease, a drug response or other biological or disease property associated with the vasculature parameters and/or changes in a subject. In some embodiments, structural characteristics identified in vascular casts may be used to identify one or more patient subpopulations that are (or are predicted to be) more responsive to a particular treatment. For example, responsive subjects may be identified as those having one or more blood vessel characteristics that were associated with responsiveness in animal models and identified by analyzing vascular casts from the responsive animals.

One or more of the characteristics described herein, or combinations of characteristics, or related structural changes over time, may be identified as structural patterns that can be associated with one or more conditions of interest. Once identified, these patterns can be used as biomarkers to identify or monitor the conditions of interest in vivo in a subject, for example, by analyzing the in situ vasculature of the subject (or a portion thereof) and detecting the presence of and/or quantifying the extent of a specific vascular structural pattern.

Accordingly, one or more of the following non-limiting structural characteristics (e.g., combinations of 2, 3, 4, 5, 6, 7, 8, 9, 10 or all of the following structural characteristics) may be evaluated (e.g., quantified) in vascular casts and/or in situ (e.g., in vivo): diameter binned vessel distribution, mean vessel diameter distribution, branching point density, vessel branching distribution, angle of vessel branching distribution, interbranching distances, vessel density, vessel tortuosity, intervessel distances, luminal vessel surface, vessel dilation (changes in vessel diameter over a segment), sinosoidalation (dilation in sinosoids), or permeability (vessel leakiness). Distributions of the quantified characteristics may be prepared and analyzed (e.g., compared). However, it should be appreciated that other structural characteristics, for example, other characteristics described herein also may be analyzed by analyzing and comparing distributions of those characteristics or features.

For example, the quantification of any of the following non-limiting features may be performed and related distributions may be analyzed as described herein: Total Intra-Vascular Volume (TIVV)—e.g., over the entire Tumor Vascular Tree and Region of Interest (ROI), over only the Small Vessels Volume within the Total Volume (or the ROI), over only the Medium Vessels Volume within the Total Volume (or the ROI), or over only Large Vessels Volume within Total Volume (or the ROI); Intra-Vascular Volume Distribution (IVVD)—e.g., broken by Total Volume, Small, Mid & Large Vessels Volumes, color encoded into small, mid, large vessels on a segmented vascular tree (e.g., based on a Poker Chip representation), linked vascular volume values through color encoding of regions within a segmented vascular tree (e.g., on a Poker Chip representation), or detected locations/regions of Max Volume, Mid Volume, Min Volume and link to regions within a segmented vascular tree (e.g., based on a Poker Chip representation); Inter-Vessel Distance (IVD)—e.g., in the form of average/Min/Max values, histograms, values in select locations (for example single locations), color encoded Vessel Tree/ROI(s) with IVD values & IVD Value Clusters; Inter-Branching Distance (IBD)—e.g., in the form of average/Min/Max values, histograms, values in select locations (for example single locations), color encoded Vessel Tree/ROI(s) with IBD values and IBD Value Clusters; Vascular Diameter Variability (VDV) along the length of the vessel—e.g., in the form of histograms for the entire vascular tree or w/in a ROI, with the ability to view such variability for a single vessel or a group of vessels on the whole tree of within select (ROI)s, or color encoded segments within a tree/ROI (e.g., based on a Poker Chip representation) based on VDV values; Vessel Branch Curvature (VBC) and Tortuosity (VBT)—e.g., in the form of histograms of each BC and BT for the entire vascular tree or within select ROI(s), with the ability to view such variability for a single vessel or a group of vessels on the whole tree or within select ROI(s), or color encoded regions within a vascular tree/ROI (e.g., color encoded chips a Poker Chip representation) based on BC or BT values; or any combination of two or more thereof. Distributions of one or more of these characteristics, or combinations of characteristics, or related structural changes over time, may be identified as structural patterns that can be associated with one or more conditions of interest.

Blood vessels may be binned according to about any of the following non-limiting diameter ranges (in microns): 0-10, 10-25, 25-50, 50-75, 75-100, 100-150, 150-200, 200-300, 300-400, 400-500, 500-1,000, or any combination thereof. However, any other suitable bin size ranges (including larger, smaller, or intermediate) may be used. In some embodiments, the number of different bins may be between about 2 and about 10. However, higher numbers of bins also may be used. In some embodiments, only 2 to 5 bins are used (e.g., 2, 3, 4, or 5). For example, three blood vessel bin sizes may be used: small, medium, and large diameters (e.g., small at less than about 35 microns or about 20-35 microns, medium about 35-70 or about 35-100 microns, and large above about 100 microns or about 100-200 microns). However, other vessel size ranges may be used to calculate population percentages or ratios as described herein. In some embodiments, a single bin is chosen with a predetermined size range and no other sizes are analyzed. In some embodiments, a parameter may be evaluated as a percentage of the total population of vessels. For example, the percentage of blood vessels having a particular diameter (e.g., 20-40 microns) as a percentage of the total population of blood vessels may be used. In some embodiments, a parameter may be evaluated as a ratio of two subpopulations within a population of vessels. It should be appreciated that the percentage populations of vessels having different properties may be evaluated by determining the relative lengths of blood vessels having different properties within a region being analyzed. However, other techniques may be used.

Aspects of the technology described herein relate to business methods that may involve the marketing and/or licensing of biomarkers associated with particular biological processes, conditions, and/or diseases. In some embodiments, patterns (e.g., geometric features) of blood vessels (e.g., observed in vivo or in casts) are analyzed to identify or evaluate associations or correlations with certain biological processes, conditions, and/or diseases of interest. Pattern parameters may be identified that can be used as structural biomarkers (e.g., for clinical, diagnostic, therapeutic, and/or research applications as described herein). These biomarkers may be used to reduce the cost and increase the efficiency and sensitivity of medical and research techniques. In one embodiment, one or more biomarkers or methods of using the biomarkers may be marketed to medical or research customers or potential customers. In one embodiment, a fee-based service may be provided to medical or research organizations wherein information relating to a medical image is obtained and analyzed for the presence of one or more biomarkers and the resulting information is returned in exchange for a fee. The amount of the fee may be determined, at least in part, by the type of image information that is provided, the type and degree of analysis that is requested, and the format and timing of the analysis. It should be understood that aspects of the technology described herein may be applicable to image information obtained from one or more of many different scanning modalities (including, but not limited to, micro CT, MDCT, rotational angiography, MRI, PACS). This information may be received from many different sources, including, but not limited to one or more of the following: medical centers, large pharmaceutical companies (e.g., in association with pre-clinical evaluations or during clinical trials), CROs (for both pre-clinical and clinical analyses), medical laboratories and practices (e.g., scanning centers), hospitals, clinics, medical centers, small biotechnology companies (e.g., in association with pre-clinical evaluations or during clinical trials), and bio-medical research organizations. The results of the analysis then may be returned to any one of these organizations. In some embodiments, the analysis results may be returned to the same entity that sent the image information. In other embodiments, the results may be returned to a different entity (e.g., the image information may be received from a scanning laboratory and the analysis may be returned to a physician). One or more steps involved with receiving the information, analyzing the structural features, processing the results and forwarding the results to a recipient may be automated. It also should be appreciated that one or more of these steps may be performed outside the United States of America. Business procedures (e.g., marketing, selling, licensing) may be performed individually or collaboratively.

Aspects of the technology described herein may be described herein in the context of individual analytical steps, particular structural features, etc. However, it should be appreciated that any of the methods and devices described herein also may be incorporated into a business method associated with the use of a biomarker based on one or more blood vessel structural features or patterns (e.g., structural features or changes observed in vascular casts obtained from therapeutic and/or disease models or conditions).

Aspects of the technology described herein may be automated (e.g., using one or more computer-implemented acts described herein). It should be appreciated that one or more pattern parameters (e.g., individual blood vessel structural feature(s), distributions of blood vessels or blood vessel structural features, or combinations thereof) may be analyzed using one or more quantitative and/or qualitative methods (e.g., based on binned data). In some embodiments, one or more parameters may be measured and quantified and the measurements may be analyzed using standard quantitative and/or statistical techniques for evaluation and/or comparison with threshold or reference values as described herein. In certain embodiments, one or more parameters may be evaluated using a predetermined scoring method, for example based on predetermined factors (e.g., for binned data). Geometrical parameters may be represented using vectors. For example, a distribution of blood vessels, blood vessel curvatures, blood vessel tortuosity, or blood vessel directions within a volume of interest may be represented using a plurality of vectors. Separate vectors may be used to represent separate vessels (e.g., vessels for which a connectivity has not been determined during the analysis). However, separate vectors also may be used to represent individual segments or fragments of a single blood vessel or portion of a vascular tree (e.g., for which connectivity has been or may be determined during the analysis). Vasculature pattern parameters may be analyzed using any appropriate technique for separating and/or categorizing numerical values or scores.

In some embodiments, a score may be obtained to relate a pattern parameter to the probability of a physiological condition such as a disease or disease stage. Aspects of the technology described herein can be used for in situ diagnostic, interventional and therapeutic analysis of one or more disease loci associated with aberrant internal structures. As used herein "in situ" means in an animal (e.g., a human) body as opposed to in a biopsy or other tissue sample. Aspects of the technology described herein can be used to research structural changes associated with a disease, for developing and evaluating disease treatments including therapeutic drugs, and for other purposes. Aspects of the technology described herein include automatically analyzing a structural feature or pattern and automatically generating a score based on the analysis.

In some embodiments, aspects of the technology described herein include detecting and/or analyzing selected internal tubular networks in situ in animals and/or in vascular casts. As used herein, an internal tubular network means a network of connected cylindrical internal body structures. Tubular networks include, but are not limited to, cardio-vascular, respiratory, gastro-intestinal, and genito-urinary systems and portions thereof within animal bodies. Accordingly, the cylindrical structures may include branched, straight, curved, and/or twisted cylindrical elements. The cylindrical structures and elements may include not only cylinders, but also may include flattened or otherwise distorted regions. The cross-section of a cylindrical structure or element may be circular, oval, approximately circular, approximately oval, or more irregular in nature. The internal diameter of the cylindrical elements may vary or may be approximately the same over the region of interest. A tubular network such as a circulatory network may be closed off from the environment outside the animal. In contrast, tubular networks such as respiratory and gastro-intestinal networks may be open to the outside environment. In some embodiments, appropriate casting and/or contrast agents (e.g., inhaled agents) may be used to analyze respiratory and/or gastro-intestinal networks.

In one embodiment, aspects of the technology described herein include analyzing a representation of a tubular network (e.g., a mathematical representation of a vascular network). In one embodiment, a representation of a network, or a portion thereof, may be obtained (e.g., from an existing database or a remote site) and analyzed. In another embodiment, a representation of a network, or a portion thereof, may be generated from structural data and then analyzed. According to aspects of the technology described herein, an analysis may include detecting the presence or absence of one or more structural features or patterns, measuring or evaluating the extent of one or more structural features or patterns, or a combination thereof.

In one embodiment, aspects of the technology described herein are useful for selectively detecting and/or analyzing patterns (e.g., structures) of an animal's vasculature to detect or monitor one or more blood vessel patterns (e.g., structures) that may be indicative of a physiological condition of the animal. A structural pattern or feature may be detected and/or analyzed for blood vessels of any size including, but not limited to, arteries, arterioles, veins, venules, and capillaries.

In one embodiment, aspects of the technology described herein are useful for selectively detecting and/or analyzing structural features or patterns of an animal's vasculature to detect or monitor one or more blood vessel structures that are characteristic of disease (e.g., a disease associated with angiogenesis). A blood vessel structure or pattern characteristic of a disease (e.g., a disease associated with angiogenesis) may provide an early diagnostic indication of the presence of the, which can allow for early treatment that can improve a patient's prognosis. In other embodiments, a blood vessel structure or pattern characteristic of a disease (e.g., a disease associated with angiogenesis) can be used as a marker (e.g., a biomarker) for staging and/or grading, to monitor disease progression, evaluate a prescribed therapy, and/or identify and/or validate a drug or treatment regimen for the disease. Diseases associated with abnormal vasculature structures or patterns include, but are not limited to, cancer, cardiovascular, dermatologic (skin), arthritic, musculoskeletal, central nervous system, neurologic, pulmonary, renal, gastrointestinal, gynecologic, genitourinary, inflammatory, infectious, and immunologic diseases.

A cancer may be a solid tumor or a leukemia. When the cancer is a leukemia, methods of the technology described herein may be directed to detecting and/or analyzing vasculature pattern(s) in the bone marrow of an animal (e.g., human).

It also should be appreciated that aspects of the technology described herein may include performing any combination of two or more acts described herein and that certain acts may be omitted in some embodiments. In one embodiment, the presence of one or more structural abnormalities may be identified or detected in a body region without generating and/or analyzing a structural representation of that body region. For example, the presence of a blood vessel abnormality may be detected directly from structure data for a body region without generating a structural representation of the vasculature for that entire body region. In another embodiment, an analysis may involve selectively representing one or more abnormal structures if they are present in a body region without representing normal structures in that body region (e.g., abnormal blood vessel structures may be represented without representing any normal blood vessels, or without representing all the normal blood vessels, without representing most of the normal blood vessels, etc.). In another embodiment, an abnormal vascular structure may be identified or detected without obtaining a detailed representation of the all the blood vessels in a body region. It may be sufficient to detect the presence of or outline of a vascular tree in a body region and perform an analysis that identifies or detects abnormal structures on specific blood vessels or the presence of excessive vascularization (e.g., a clump of neovasculature representing malignancy) without representing all the normal details of the vascular tree or even detecting individual blood vessels in the vascular tree. Accordingly, in some aspects a low resolution data set for a body region may be sufficient to detect or identify certain structural indicia of a disease such as cancer.

Aspects of the technology described herein may include automating one or more acts. For example, an analysis may be automated in order to generate an output automatically. Acts of the technology described herein may be automate using, for example, a computer system.

As should be appreciated from the foregoing, in one embodiment, raw or processed structure data may be obtained at a medical or research center and sent to a computer at a remote site where one or more of the analytical steps described above may be performed (e.g., for a fee). The output from the analysis may be then returned to the medical or research center either in computer readable form to a computer at the medical or research center, in a hard copy, in another tangible form, or in any other suitable form including those described herein.

In another embodiment, one or more software programs that implement one or more functionalities described herein may be provided and installed at a medical or research center (e.g., for a fee). The programs can be provided on disk, downloaded from an internal or remote (e.g., external) site, or loaded in any suitable manner. Reference information that is used in any functionality described herein may be provided along with the software or separately. In one embodiment, reference information (e.g., information relating to normal or abnormal blood vessel structures) may be available on disk, downloaded from an internal or remote (e.g., external) site, or loaded in any suitable manner.

As used herein, "remote" means at a site that is different from the immediate location of the imaging device (e.g., the medical scanner). The remote site can be a central computer or computing facility at a hospital, medical, or research center (e.g., within the network or intranet of the center), or can be outside the hospital, medical, or research center (e.g., outside the network or intranet of the center). The remote site can be in the same state, in a different state, or in a different country from the site of data acquisition by the imaging device.

In some embodiments, multimodal analyses (e.g., using structure data from two or more different types of imaging devices) may be used together. Accordingly, aspects of the present technology described herein may include the ability to process and analyze different types of structure data and either combine the results to generate a combined output, or to generate a separate output is generated for each imaging modality. In some embodiments, an organ, tissue, or animal perfused with a casting agent and/or an imaging agent may be sent to an imaging center for analysis.

In some embodiments, in vivo and/or ex vivo casting methods of the technology described herein can be used to identify one or more vascular patterns (e.g., including one or more structural parameters, structure distributions, combinations thereof) and/or time-dependent changes thereof that can be used as biomarker(s) for a disease or a response to a therapy, or for monitoring patients for indicia of disease or response to therapy, or for other applications where vascular information may be informative. Accordingly, such vascular patterns or changes thereof identified according to methods of the technology described herein can be used for diagnostic, interventional, therapeutic, research, and treatment development and evaluation. Non-limiting examples of some of these embodiments are described below.

EXAMPLES

Example 1

Xenotopic Tumor Models

A tumor model can be generated by inoculating human non-small cell lung tumor cell line (A549 from ATCC, Inc.) subcutaneously in immunodeficient mice (SCID). SCID male mice (6-8 weeks old from Charles River Inc.) are inoculated subcutaneously in the lower back with a suspension of $1 \times 10^6$ human lung tumor cells (A549) in 0.2 ml of PBS. All mice are fed normal chow diet throughout the duration of the experiment. All mice weights are measured throughout the experiment. Tumor size is measured with calipers twice-a-week and tumor volume is calculated using the formula Length$^2 \times$Width$\times 0.52$. All mice are randomized into two treatment groups (approximately 10 mice per group) when the median tumor volume reaches approximately 500 mm$^3$. The treatment groups can be treated according to the following schedule using intraperitoneal (i.p.) administration of either a control composition or an anti-angiogenic compound. For example, different levels of an anti-angiogenic compound can be used and the results compared to a control group that is not treated with an anti-angiogenic compound (e.g., Avastin® available from Genentech, South San Francisco, Calif.). For example:

Group 1: Control group-treated with saline/PBS twice a week.

Group 2: High Avastin®-treated with Avastin® at 5 mg/kg/i.p. twice a week.

Group 3: Low Avastin®-treated with Avastin® at 0.5 mg/kg/i.p. twice a week.

Experiments are terminated 1.5 weeks after initial treatment.

At the end-point, all mice are anesthetized and systemically perfused with a casting agent.

Example 2

Perfusion with Casting Agent

Perfusion with a casting agent, Mercox (available from Ladd Research, Williston, Vt.) can be performed as follows. An initial anticoagulation step for each animal is performed using an i.v. injection of heparin (10,000 U/ml, 0.3 cc/mouse). After 30 minutes, the animals are anesthetized. Each animal's heart is cannulated and the animal perfused with warm physiological saline at physiological pressure (with an open vein draining the organ or with an open vena cava). Perfusion is continued until the organ or animal is clear of blood. Mercox monomer is filtered through a 0.5 µm filter and a casting resin is prepared by mixing 8 ml Mercox, 2 ml methylmethacrylate, and 0.3 ml catalyst. The resin is infused through the same cannula until the onset of polymerization (the resin changes color to brown and emits heat, ~10 min). The organ or animal is carefully immersed in a 60° C. water bath for 2 hours (or overnight in a sealed container). The tissue is removed by incubating in alternating rinses of 5% KOH and distilled water (for example in a 60° C. water bath sealed) followed by thorough rinsing in distilled water. The cast is cleaned in 5% formic acid for 15 minutes and rinsed thoroughly in distilled water and frozen in distilled water. The resulting block of ice is lyophilized (care should be taken not to melt the ice, the ice should melt as it lyophilizes). The resulting cast can be analyzed to identify one or more structural characteristics of interest.

Example 3

Xenotopic Tumor Models Response to Anti-Angiogenic Therapy

Figure 14:
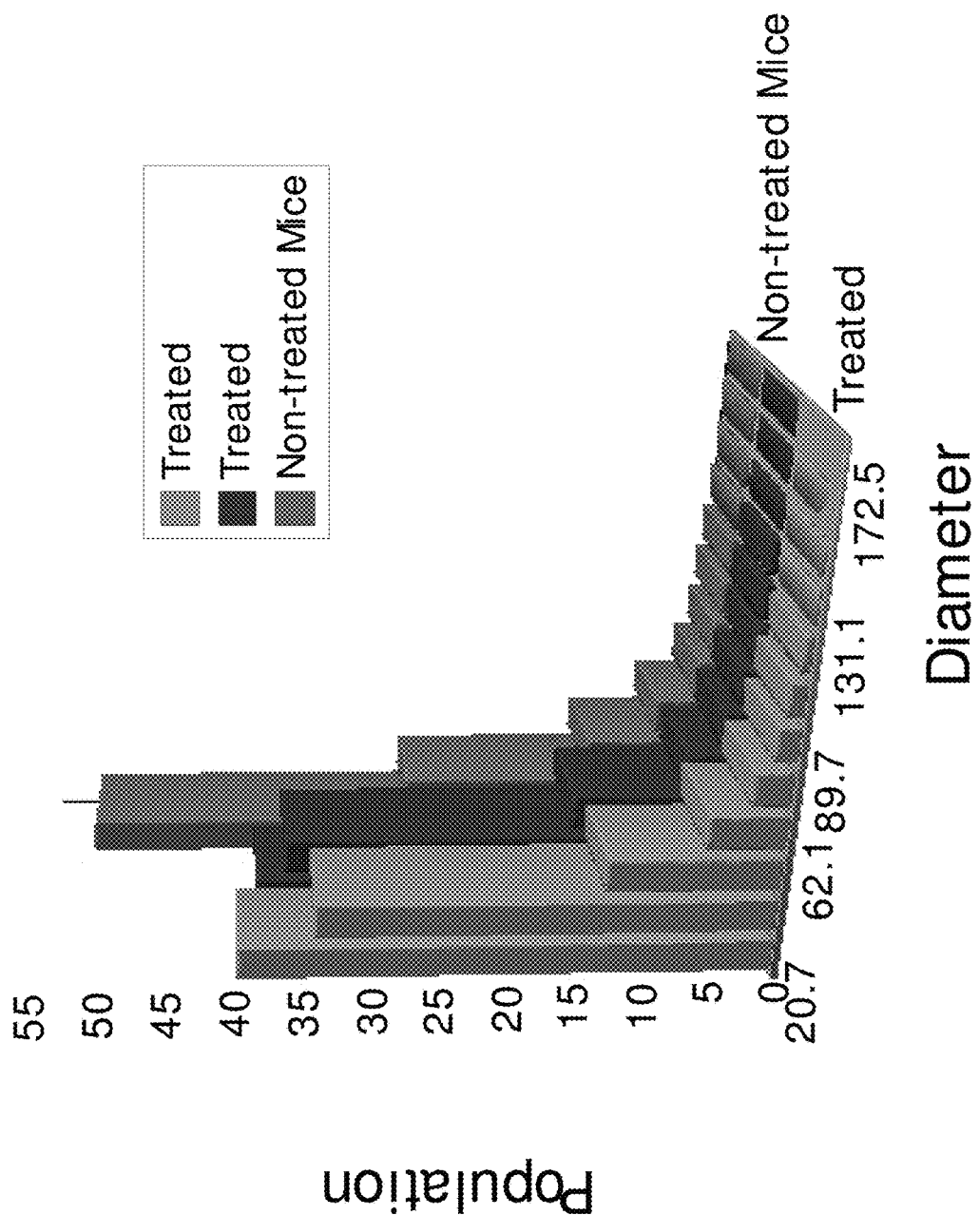
FIG. 14 illustrates blood vessel size distribution in an example of casts of a xenograft tumor model after treatment with Avastin® (an anti-angiogenic agent available from Genentech, South San Francisco, Calif.), in accordance with some embodiments of the technology described herein.
Figure 15:
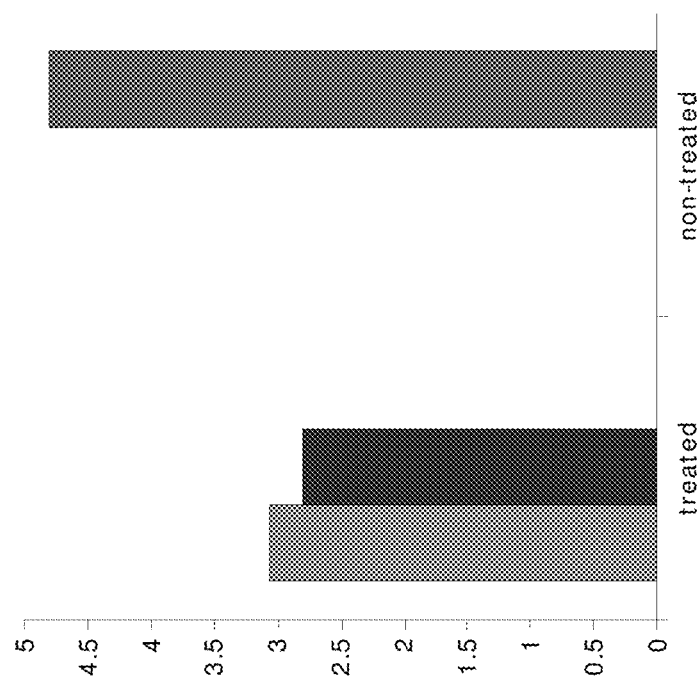
FIG. 15 illustrates the vessel population ratio between small and middle size vessels in an example of casts of a xenograft tumor model after treatment with Avastin®, in accordance with some embodiments of the technology described herein.
Figure 16:
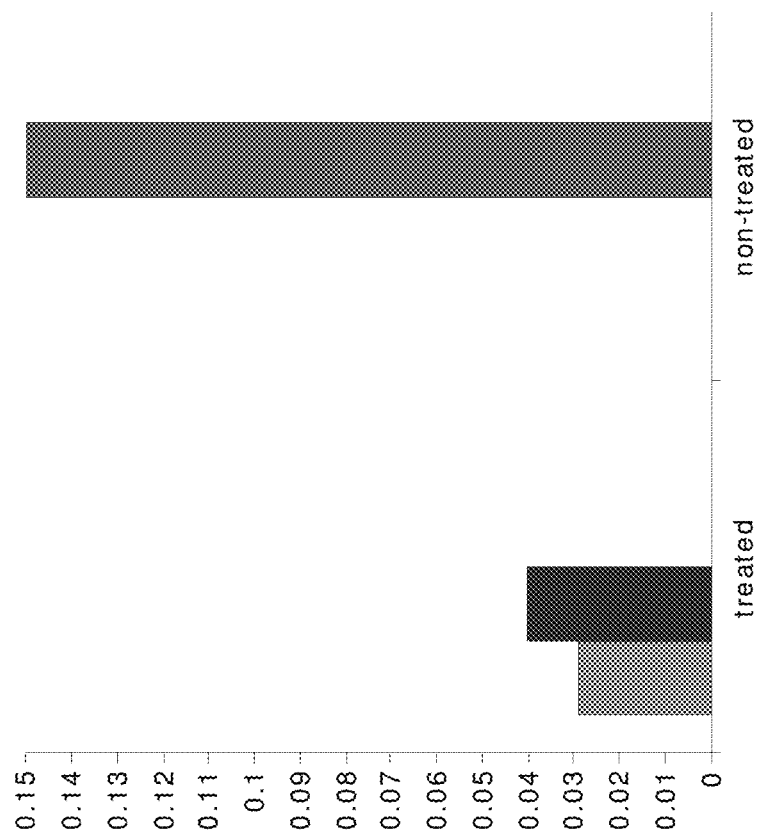
FIG. 16 illustrates the vessel population ratio between large and middle size vessels in an example of casts of a xenograft tumor model after treatment with Avastin®, in accordance with some embodiments of the technology described herein.
Figure 17:
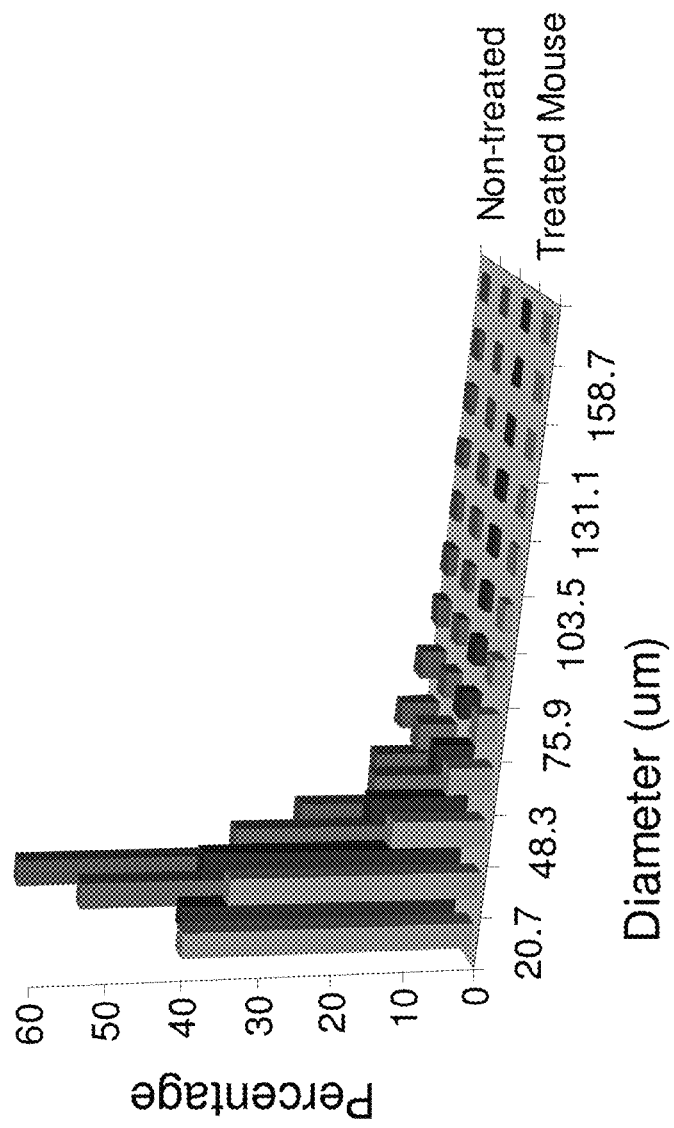
FIG. 17 illustrates the vessel population distribution in an example of casts of a tumor model after treatment with Avastin®, in accordance with some embodiments of the technology described herein.
Figure 18:
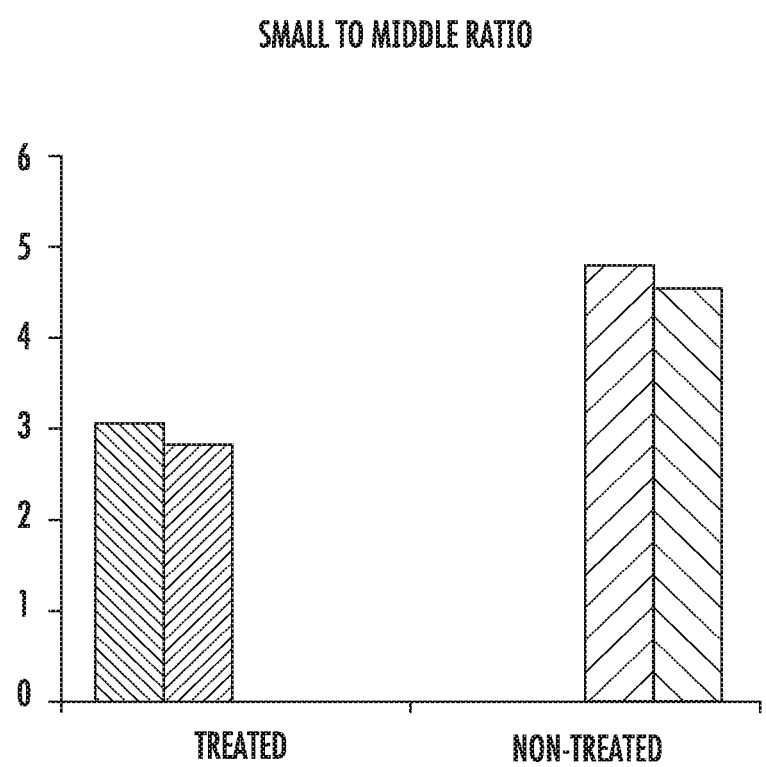
FIG. 18 illustrates the vessel population ratio between small and middle size vessels in an example of casts of a tumor model after treatment with Avastin®, in accordance with some embodiments of the technology described herein.
Figure 19:
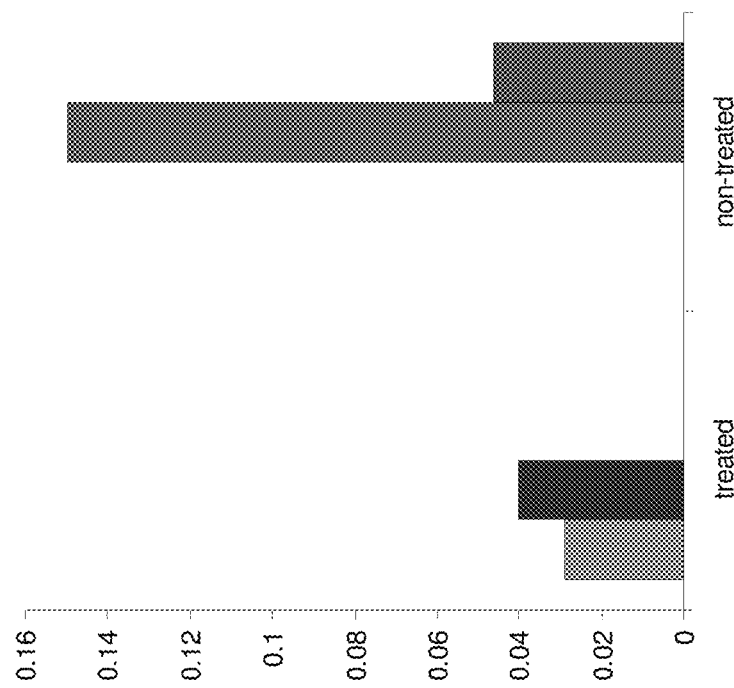
FIG. 19 illustrates the vessel population ratio between large and middle size vessels in an example of casts of a tumor model after treatment with Avastin®, in accordance with some embodiments of the technology described herein.

Xenotopic mouse models obtained as described in Example 1 were treated with either a control solution of saline/PBS or an anti-angiogenic preparation of Avastin® at 0.5 mg/kg/i.p. as described above. At the end-point, vascular casts were prepared as described in Example 2 above and analyzed for two treated mice (both treated with Avastin® at 0.5 mg/kg/i.p.) and one control mouse. The resulting vascular casts were scanned using a micro CT-scanner and the results of the structural analysis are shown in FIGS. 14-17. The analysis was performed by determining the number of blood vessels within bins of different diameter ranges for the xenotopic tumor in the treated and control animals. The bins were each 13.8 µm wide and the smallest bin included blood vessels having a diameter of between 20.7 µm and 34.5 µm. Mean tumor volumes did not differ significantly between the groups at the end of the experiment. However differences in blood vessel diameter distributions were detected as shown in FIGS. 14-17. FIG. 14 shows the resulting vessel population distribution. Treated tumors had 20% less small diameter sized vessels than untreated tumors, and treated tumors had a higher percentage of middle diameter sized vessels than untreated tumors. The blood vessel population distributions were consistent for both treated animals. FIG. 15 shows the vessel population ratio between small (approximately 21-35 µm) and middle (approximately 35-49 µm) size vessels in the tumors of the control and treated animals. The ratio decreased after inhibitor treatment with Avastin®, and this ratio was consistent within the treated group. FIG. 16 shows the vessel population ratio between large (approximately 147-161 µm) and middle (approximately 33-77 µm) size vessels. The ratio decreased after treatment with Avastin®, and this ratio was consistent within the treated group. Additional experimental results are shown in FIGS. 17-19.

The following considerations apply to the specific examples and the entire written specification herein (including the summary, detailed description, and claims). It should be appreciated that casts, like in situ blood vessels, are three-dimensional structures. Accordingly, imaging and analytical techniques described herein provide information about three-dimensional structural characteristics. In some embodiments, techniques are used to generate three-dimensional representations of vascular casts and/or in situ blood vessels. In some embodiments, techniques are used to generate three-dimensional images of vascular casts and/or in situ blood vessels. The three-dimensional representations and/or images can be analyzed as described herein.

However, it should be appreciated that aspects of the technology described herein are not limited to three-dimensional structural characteristics. In some embodiments, aspects of vascular casts and/or in situ blood vessels may be represented and/or imaged in one or two dimensions and an analysis of one or two-dimensional features may be performed and used as described herein. It also should be appreciated that the structural features described herein may be measured or quantified using any appropriate units, including numbers, lengths or distances, angles, percentages, etc., or any combination thereof, further including any of these units as a function of volume or area. Similarly, it should be appreciated that vascular changes over time or in response to treatment may involve an increase or a decrease of one or more of these structural features. For example, an increase in structures associated with angiogenesis may be associated with certain disease progressions. In contrast, a decrease in structures associated with angiogenesis may be associated with disease regression (e.g., in response to treatment).

It also should be appreciated that descriptions herein related to obtaining distributions of quantitative values for vessel parameters within a region of interest are preferably based on methodologies that detect and quantify all or substantially all of the detectable vessels within the region of interest based on the detection technique that is used for that analysis. Different techniques may have different efficiencies. However, profiles and comparisons are preferably based on data from the same or equivalent detection and/or reconstruction techniques. It also should be appreciated that comparisons and/or analyses described herein may involve a statistical analysis using one or more standard statistical techniques to determine whether a change in a structure or pattern or other characteristic described herein (e.g., an increase or decrease over time, or in response to a therapeutic drug), or a difference or similarity between two structures or patterns or other characteristics described herein are statistically significant.

Having thus described several aspects of at least one embodiment of this technology described herein, it is to be appreciated various alterations, modifications, and improvements will readily occur to those skilled in the art. Such alterations, modifications, and improvements are intended to be within the spirit and scope of the technology described herein. Any suitable analytical techniques may be used for perfused tissue and organs according to the methods described herein, including for example, the analytical techniques that are described in PCT US2005/047081 and PCT US2007/026048 the disclosures of which are incorporated herein by reference in their entirety. Accordingly, the foregoing description and embodiments are by way of example only. In the event of conflict between different disclosures, the disclosure of the present application shall control.

It should be appreciated from the foregoing, there are numerous aspects of the technology described herein described herein that can be used independently of one another or in any combination. In particular, any of the herein described operations may be employed in any of numerous combinations and procedures. In addition, aspects of the technology described herein can be used in connection with a variety of types of images or any dimensionality. Moreover, one or more automatic operations can be used in combination with one or more manual operations, as the aspects of the technology described herein are not limited in this respect. Distribution analyses, however obtained, may be used to facilitate the characterization of any of various morphological changes to tissue and/or to assist in assessing the efficacy of treatment using any of the herein described techniques, alone or in combination.

Figure 28:
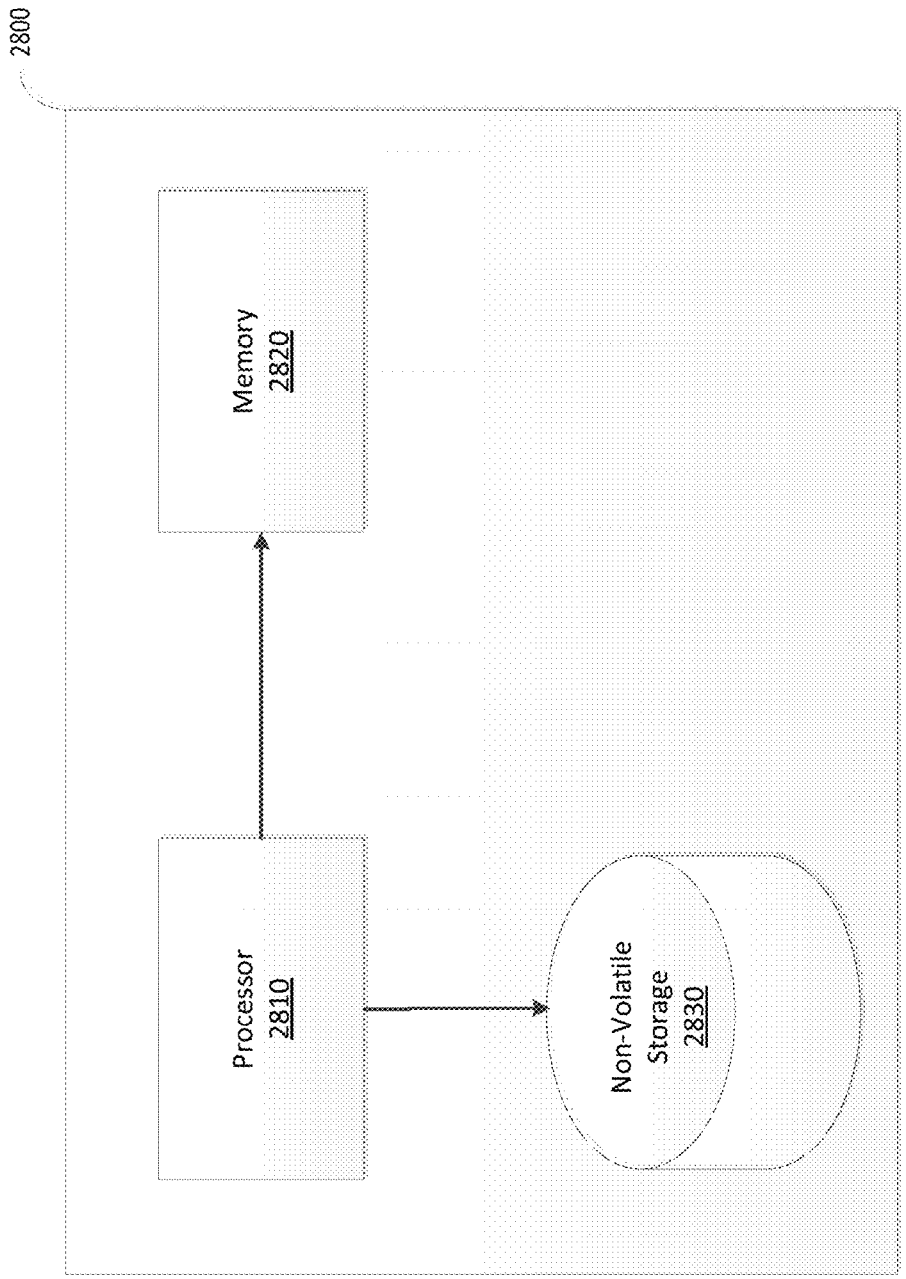
FIG. 28 is a block diagram of an illustrative computer system that may be used in implementing some embodiments.

An illustrative implementation of a computer system 2800 that may be used to implement one or more of the techniques described herein (e.g., any of the processes described herein such as processes 2000, 2100, 2200, 2300, and 2500 related to generating a vessel network at least in part by linking vessel centerline voxels) is shown in FIG. 28. Computer system 2800 may include one or more processors 2810 and one or more non-transitory computer-readable storage media (e.g., memory 2820 and one or more non-volatile storage media 2830). The processor 2810 may control writing data to and reading data from the memory 2820 and the non-volatile storage device 2830 in any suitable manner, as the aspects of the invention described herein are not limited in this respect.

To perform functionality and/or techniques described herein, the processor 2810 may execute one or more instructions stored in one or more computer-readable storage media (e.g., the memory 2820, storage media, etc.), which may serve as non-transitory computer-readable storage media storing instructions for execution by the processor 2810. Computer system 2800 may also include any other processor, controller or control unit needed to route data, perform computations, perform I/O functionality, etc. For example, computer system 2800 may include any number and type of input functionality to receive data and/or may include any number and type of output functionality to provide data, and may include control apparatus to operate any present I/O functionality.

In connection with the techniques described herein, one or more programs configured to perform one or more processes related to generating a vessel network (examples of which have been provided above) and/or any other suitable processes may be stored on one or more computer-readable storage media of computer system 2800. Processor 2810 may execute any one or combination of such programs that are available to the processor by being stored locally on computer system 2800 or accessible over a network. Any other software, programs or instructions described herein may also be stored and executed by computer system 2800. Computer 2800 may be a standalone computer, server, part of a distributed computing system, mobile device, etc., and may be connected to a network and capable of accessing resources over the network and/or communicate with one or more other computers connected to the network.

Implementation of some of the techniques described herein (e.g., linking centerline voxels, identifying branch points, etc.) on a computer system such as computer 2800 is an integral component of practicing these techniques, as aspect of these techniques cannot be realized absent computer implementation The herein-described embodiments of the present technology described herein can be implemented in any of numerous ways. For example, linking of centerline voxels may be implemented using hardware, software or a combination thereof. When implemented in software, the software code can be executed on any suitable processor or collection of processors, whether provided in a single computer or distributed among multiple computers. It should be appreciated that any component or collection of components that perform the functions described herein can be generically considered as one or more controllers that control the herein-discussed functions. The one or more controllers can be implemented in numerous ways, such as with dedicated hardware, or with general purpose hardware (e.g., one or more processors) that is programmed using microcode or software to perform the functions recited herein.

The terms "program" or "software" are used herein in a generic sense to refer to any type of computer code or set of processor-executable instructions that can be employed to program a computer or other processor to implement various aspects of embodiments as discussed above. Additionally, it should be appreciated that according to one aspect, one or more computer programs that when executed perform methods of the disclosure provided herein need not reside on a single computer or processor, but may be distributed in a modular fashion among different computers or processors to implement various aspects of the disclosure provided herein.

Processor-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Also, data structures may be stored in one or more non-transitory computer-readable storage media in any suitable form. For simplicity of illustration, data structures may be shown to have fields that are related through location in the data structure. Such relationships may likewise be achieved by assigning storage for the fields with locations in a non-transitory computer-readable medium that convey relationship between the fields. However, any suitable mechanism may be used to establish relationships among information in fields of a data structure, including through the use of pointers, tags or other mechanisms that establish relationships among data elements.

Also, various inventive concepts may be embodied as one or more processes, of which examples (see e.g., FIGS. 20-23 and 25) have been provided. The acts performed as part of each process may be ordered in any suitable way. Accordingly, embodiments may be constructed in which acts are performed in an order different than illustrated, which may include performing some acts concurrently, even though shown as sequential acts in illustrative embodiments.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

The phraseology and terminology used herein is for the purpose of description and should not be regarded as limiting. The use of "including," "comprising," "having," "containing", "involving", and variations thereof, is meant to encompass the items listed thereafter and additional items.

Having described several embodiments of the techniques described herein in detail, various modifications, and improvements will readily occur to those skilled in the art. Such modifications and improvements are intended to be within the spirit and scope of the disclosure. Accordingly, the foregoing description is by way of example only, and is not intended as limiting. The techniques are limited only as defined by the following claims and the equivalents thereto.

What is claimed is:

1. A method of identifying 3D branch points in a 3D geometry extracted from more than one medical images, comprising:
   extracting information from the more than one medical images to identify a plurality of geometric objects, each having parameter values including at least one value for location and at least one value for direction/orientation;
   identifying a set of the geometric objects that represent a vessel centerline based on the at least one value for location and at least one value for direction/orientation;
   calculating at least one branching score for each of the set of geometric objects;
   identifying a branch point based at least on the at least one branching score, wherein a branch point is defined as a point in a vessel structure where a vessel branches into two or more vessels; and
   updating a linked vessel network based on the identified branch point, wherein the updating comprises linking two or more vessel centerlines at the identified branch point.

2. The method of claim 1, wherein the branching score is determined based on a measure of cylindrical asymmetry associated with each geometric object.

3. The method of claim 2, wherein a plurality of displacement vectors are determined, each displacement vector representing a direction between a branch point candidate and one of the neighboring geometric objects, wherein greater consistency in directions of the displacement vectors is indicative of a branch point.

4. The method of claim 1, further comprising:
   using the at least one branching score to identify a set of branch point candidates; and
   analyzing characteristics of the branch point candidates to refine the set of branch point candidates;
   wherein the branch points are identified from the refined set of branch point candidates.

5. The method of claim 4, wherein the characteristics include the behavior of surrounding geometric objects.

6. The method of claim 5, wherein the surrounding geometric objects are linked together to form a second vessel, and the likelihood that the branch point candidate links to the second vessel is evaluated.

7. The method of claim 4, wherein the set of branch point candidates is refined using a coarse-to-fine approach.

8. The method of claim 4, wherein neighboring geometric objects around the branch point candidate are evaluated.

9. The method of claim 8, wherein a plurality of displacement vectors are determined, each displacement vector representing a direction between the branch point candidate and one of the neighboring geometric objects, wherein smaller distance to the mean displacement vectors is indicative of a branch point.

10. The method of claim 1, further comprising determining a type of junction formed at the branch point.

11. The method of claim 10, wherein the type of junction is selected from a T-type junction, a Y-type junction and a V-type junction.

12. The method of claim 1, further comprising:
    labelling linked centerline locations;
    comparing a proposed branch point candidate with linked labels; and
    updating the linked vessel network to achieve branching structure consistency from multiple directions.

13. The method of claim 12, wherein the label indicates whether the linked centerline location has already been identified as a branch point.

14. The method of claim 1, wherein each of the geometric objects each comprise a cross-section of a vessel, represented as a cylinder defined by a center location, a radius and an orientation, and the vessel centerline comprises a plurality of cylinders linked together.

\* \* \* \* \*